(12) United States Patent
Gunderson et al.

(10) Patent No.: US 8,343,941 B2
(45) Date of Patent: Jan. 1, 2013

(54) COMPOSITIONS AND METHODS FOR GENE SILENCING

(75) Inventors: Samuel Ian Gunderson, Piscataway, NJ (US); Rafal Goraczniak, Hillsborough, NJ (US)

(73) Assignees: Rutgers, The State University of New jersey, New Brunswicj, NJ (US); Silagene, Inc., Hillsborough, NJ (US)

( * ) Notice: Subject to any disclaimer, the term of this patent is extended or adjusted under 35 U.S.C. 154(b) by 0 days.

(21) Appl. No.: 13/082,865

(22) Filed: Apr. 8, 2011

(65) Prior Publication Data
US 2011/0217365 A1    Sep. 8, 2011

Related U.S. Application Data

(63) Continuation-in-part of application No. 12/570,389, filed on Sep. 30, 2009, which is a continuation-in-part of application No. PCT/US2008/058907, filed on Mar. 31, 2008.

(60) Provisional application No. 61/144,087, filed on Jan. 12, 2009, provisional application No. 60/921,032, filed on Mar. 30, 2007.

(51) Int. Cl.
  *C12N 15/11*    (2006.01)
  *A61K 48/00*    (2006.01)

(52) U.S. Cl. .................... 514/44 A; 514/44 R

(58) Field of Classification Search ............... 514/44 A, 514/44 R
See application file for complete search history.

(56) References Cited

U.S. PATENT DOCUMENTS
6,692,910 B2    2/2004    Rowe et al.
2003/0082149 A1    5/2003    Rowe et al.
2003/0143732 A1    7/2003    Fosnaugh et al.
2003/0144231 A1    7/2003    Vengel et al.
2005/0043261 A1    2/2005    Alonso et al.
2005/0182010 A1    8/2005    de Haan et al.

FOREIGN PATENT DOCUMENTS
WO    03/095647    11/2003
WO    2008/093141    8/2008
WO    2009/095517    8/2009

OTHER PUBLICATIONS

Liu, et al., "Analysis of inhibitory action of modified U1 snRNAs on target gene expression: discrimination of two RNA targets differing bp a 1 by mismatch", Nucleic Acids Res. (2002) 30(11):2329-39.

Beckley, et al., "Reduction of target gene expression by a modified U1 snRNA", Mol. Cell Biol. (2001) 21(8):2815-25.

Fortes, et al., "Inhibiting expression of specific genes in mammalian cells with 5' end-mutated U1 small nuclear RNAs targeted to terminal exons of pre-mRNA", Proc. Natl. Acad. Sci. U.S.A. (2003) 100(14):8264-9.

Furth, et al., "Sequences homologous to 5' splice sites are required for the inhibitory activity of papillomavirus late 3' untranslated regions", Mol. Cell Biol. (1994) 14(8):5278-89.

Gunderson, et al., "U1 snRNP inhibits pre-mRNA polyadenylation through a direct interaction between U1 70K and poly(A) polymerase", Mol. Cell (1998) 1(2):255-64.

(Continued)

*Primary Examiner* — Jon E Angell
(74) *Attorney, Agent, or Firm* — Dann, Dorfman Herrell & Skillman; Robert C. Netter, Jr.

(57) ABSTRACT

Compositions and methods for modulating the expression of a protein of interest are provided.

25 Claims, 42 Drawing Sheets

OTHER PUBLICATIONS

Abad, X., et al. "Comparison between RNAu and RNAi." Proceedings of the 2008 Miami Winter Symposium, [Online]. Feb. 2, 2008;19:T9. <http://www.med.miami.edu/mnbws/documents/ABAD.pdf> Retrieved Jul. 7, 2009.

Abad, X., et al. "Requirements for gene silencing mediated by U1 snRNA binding to a target sequence." Nucleic Acids Res. 2008 Apr;36(7):2338-52. Epub Feb. 24, 2008.

Sajic, R., et al. "Use of modified U1 snRNAs to inhibit HIV-1 replication." Nucleic Acids Res. 2007;35(1):247-55. Epub Dec. 8, 2006.

Liu, P., et al. "Modified U1 snRNA suppresses expression of a targeted endogenous RNA by inhibiting polyadenylation of the transcript." Nucleic Acids Res. Mar. 3, 2004;32(4):1512-7.

Wu, C., et al. "Experimental study of inhibition of hepatitis B by dual-target antisense RNA." Zhonghua Yi Xue Za Zhi. May 25, 2001;81(10):605-8. [ABSTRACT].

Hossbach, M., et al. "Gene silencing with siRNA duplexes composed of target-mRNA-complementary and partially palindromic or partially complementary single-stranded siRNAs." RNA Biol. Apr. 2006;3(2):82-9. Epub Apr. 19, 2006.

Kato, K., et al. "Hyperstable U1snRNA complementary to the K-ras transcripts induces cell death in pancreatic cancer cells." Br J Cancer. Oct. 7, 2002;87(8):898-904.

Liu, D., et al. "Stable human immunodeficiency virus type 1 (HIV-1) resistance in transformed CD4+ monocytic cells treated with multitargeting HIV-1 antisense sequences incorporated into U1 snRNA." J Virol. May 1997;71(5):4079-85.

Montgomery, R.A., et al. "Inhibition of fibrillin 1 expression using U1 snRNA as a vehicle for the presentation of antisense targeting sequence." Hum Mol Genet. Apr. 1997;6(4):519-25.

Gorman, L., et al. "Restoration of correct splicing of thalassemic beta-globin pre-mRNA by modified U1 snRNAs." J Biol Chem. Nov. 17, 2000;275(46):35914-9.

Temsamani, J., et al. "Biotinylated antisense methylphosphonate oligodeoxynucleotides. Inhibition of spliceosome assembly and affinity selection of U1 and U2 small nuclear RNPs." J Biol Chem. Jan. 5, 1991;266(1):468-72.

Goraczniak, R., et al. "Gene silencing by synthetic U1 adaptors." Nat Biotechnol. Mar. 2009;27(3):257-63. Epub Feb. 15, 2009.

A
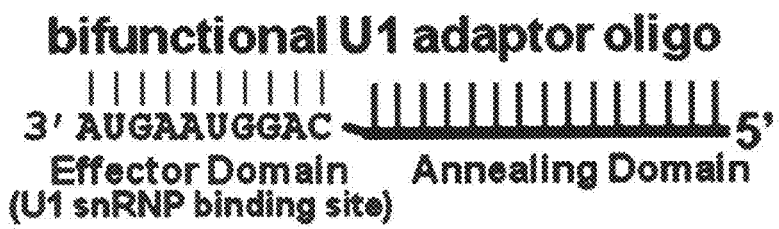
B
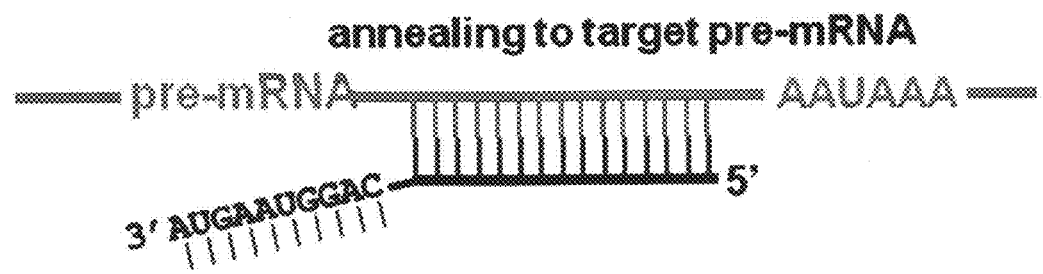
C
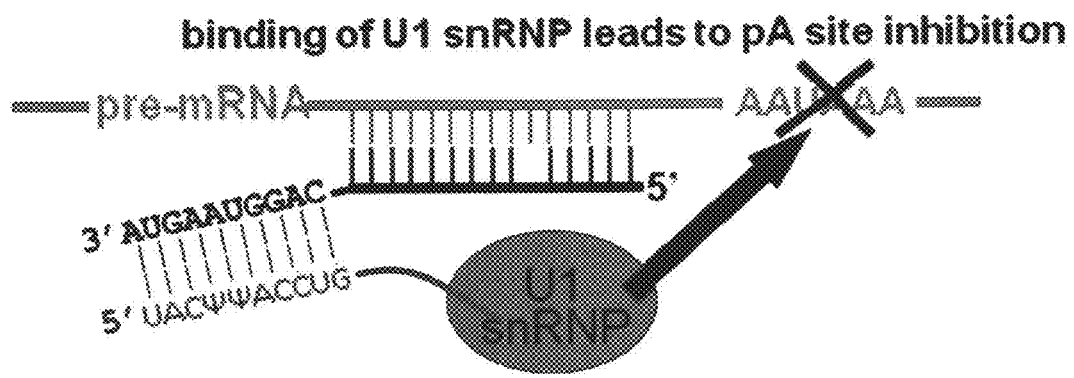
Figure 1

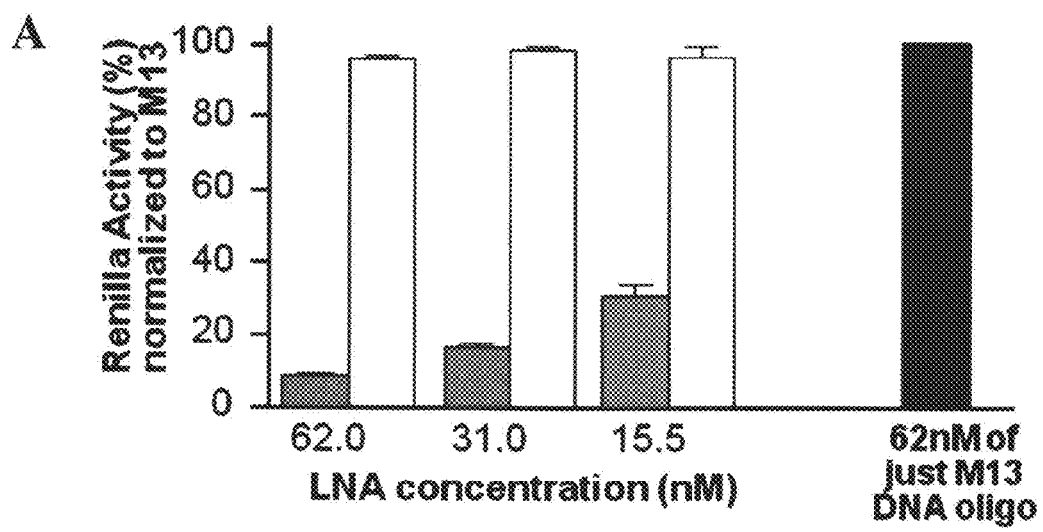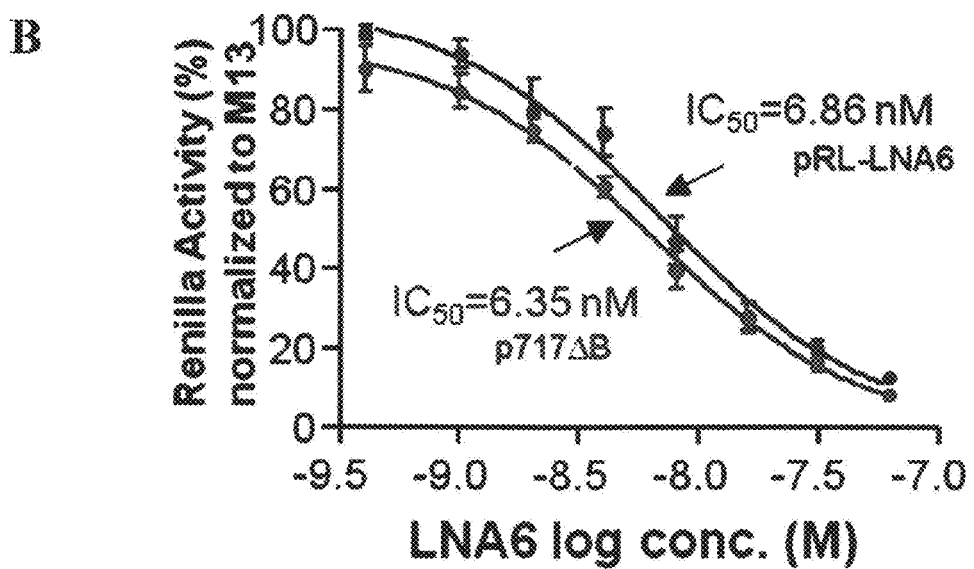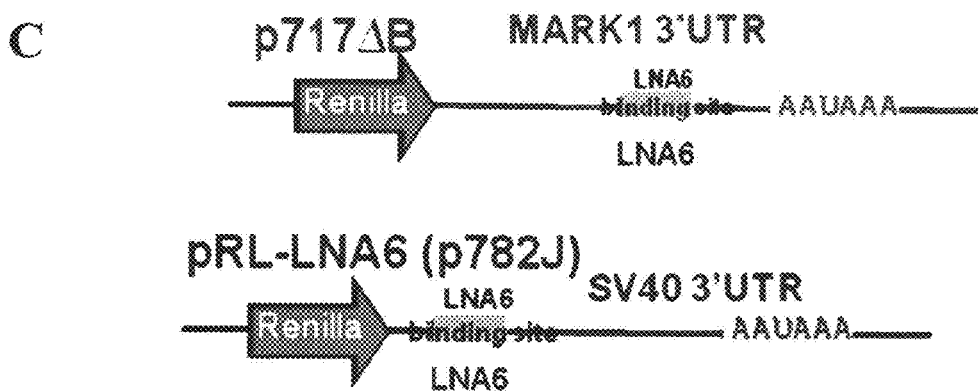
Figure 3

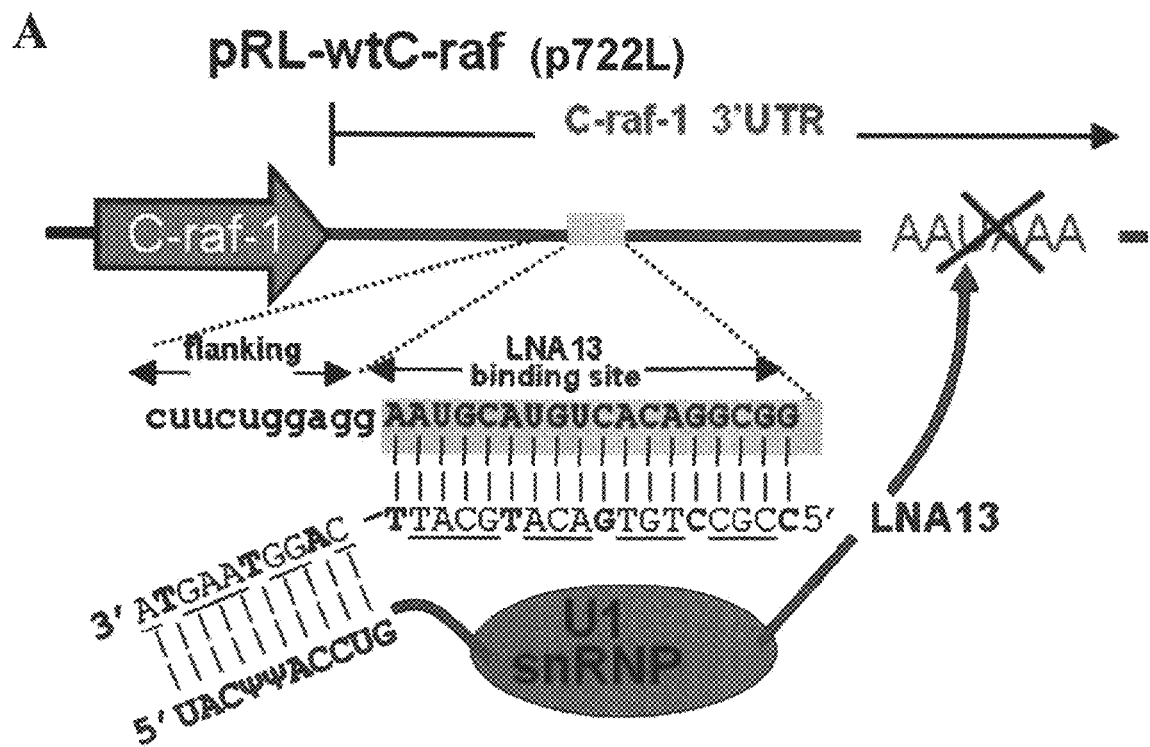
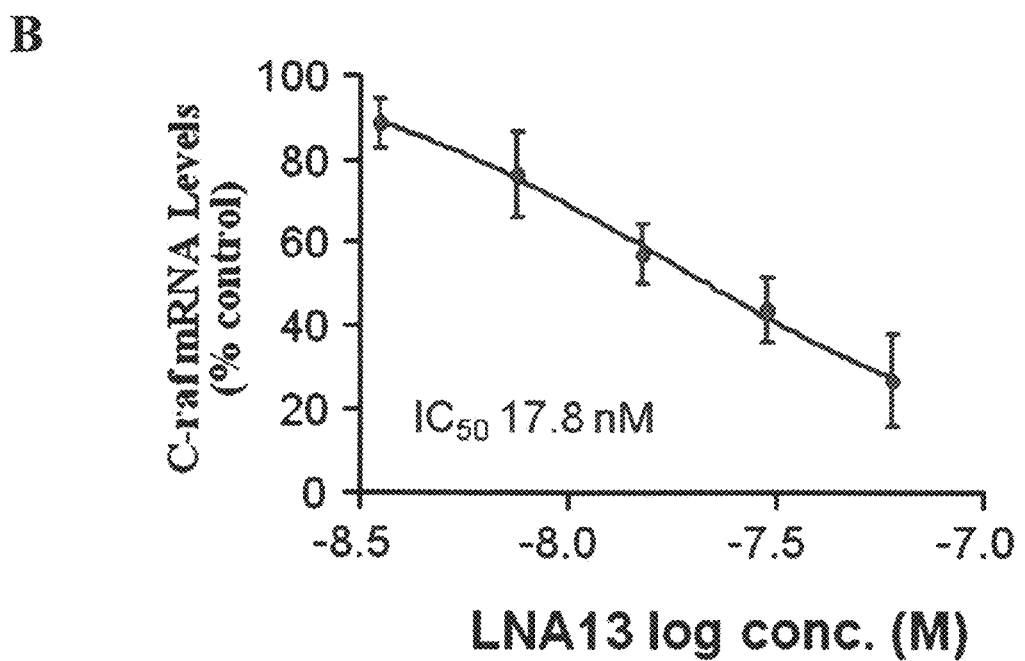
Figure 5

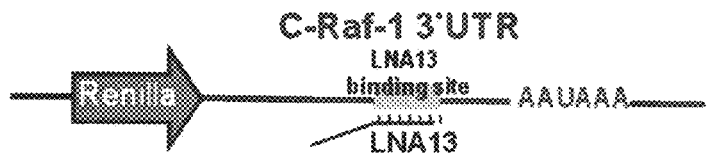
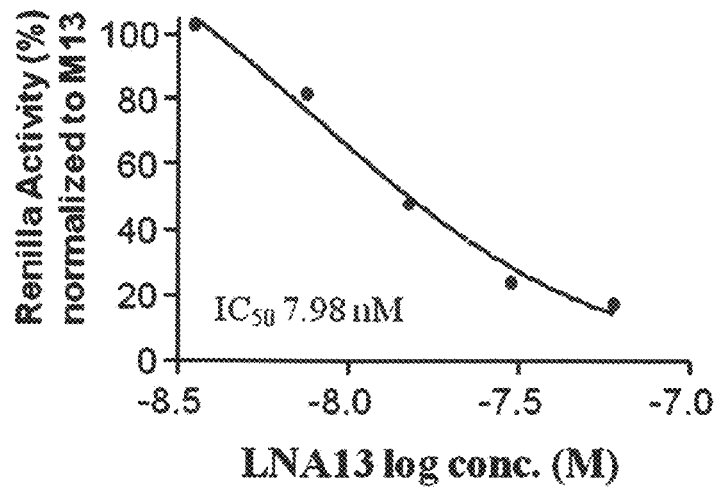
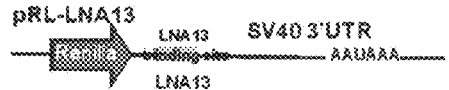
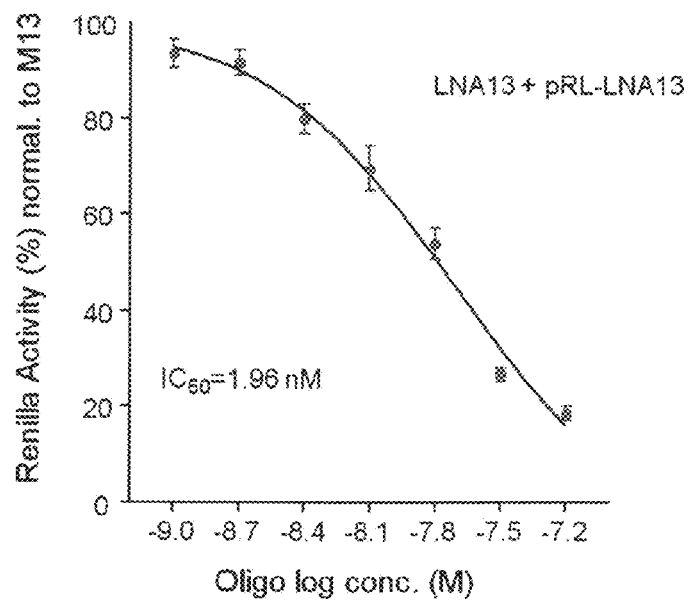
Figure 6

A
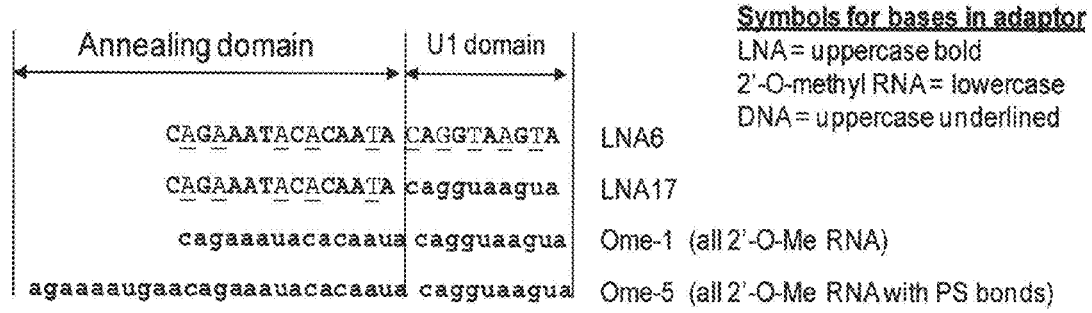
B
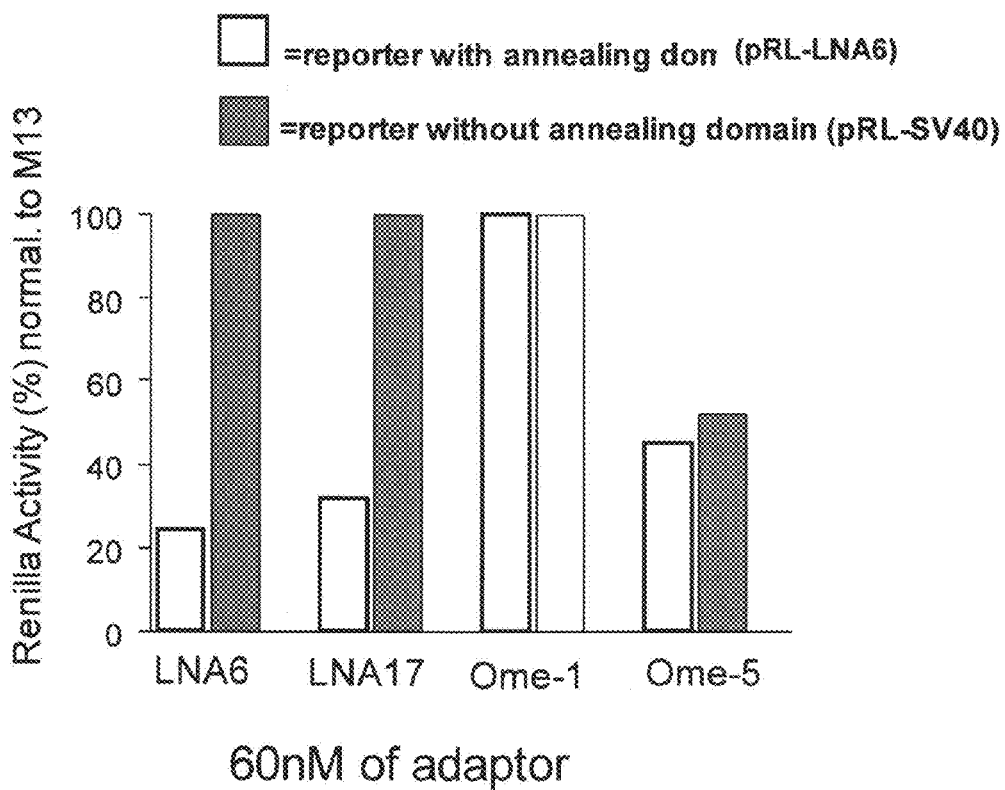
Figure 7

A
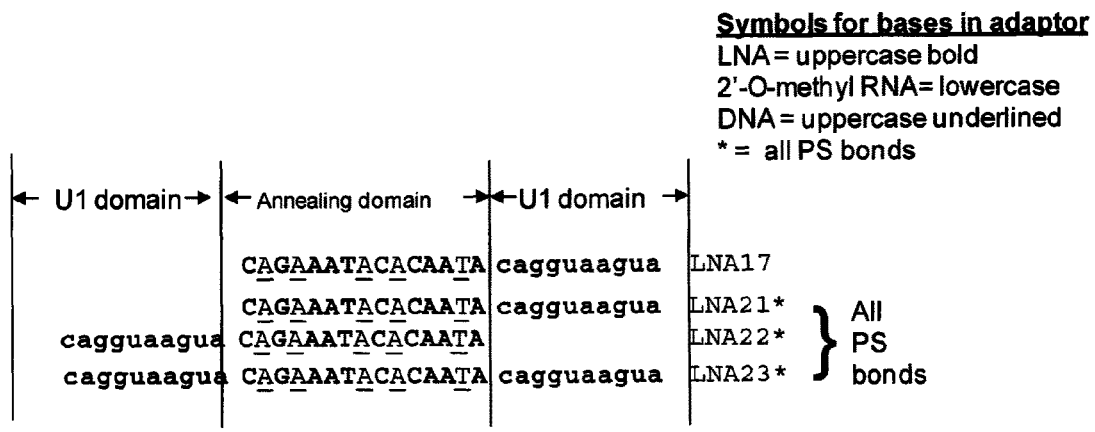
B
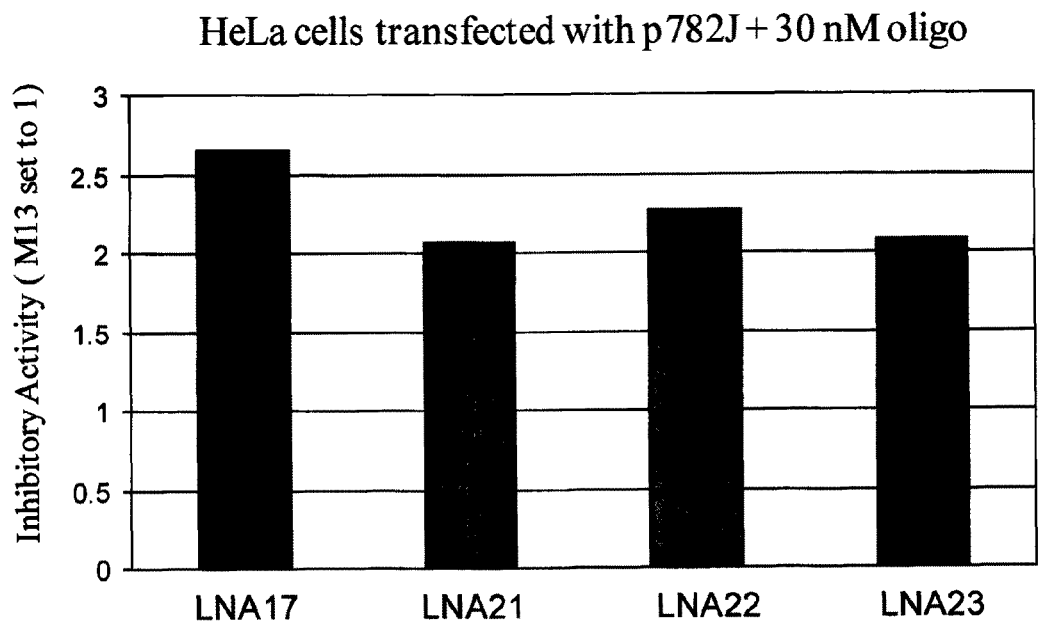
Figure 8

A

| | ←Annealing domain→ | ←U1 domain→ | |
|---|---|---|---|
| Tm=66°C | CAGAAATACACAATA | cagguaagua | LNA17 |
| Tm=77°C | CAGAAATACACAATA | cagguaagua | LNA24/15 |
| Tm=60°C | AAATACACAATA | cagguaagua | LNA24/12 |

Symbols for bases in adaptor
LNA = uppercase bold
2'-O-methyl RNA = lowercase
DNA = uppercase underlined

B

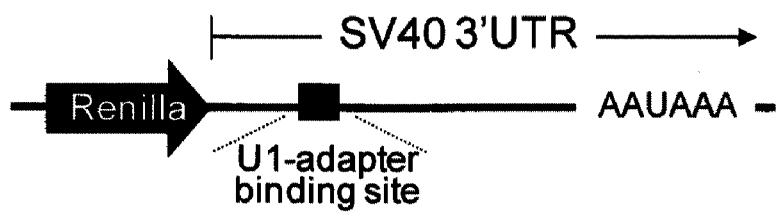
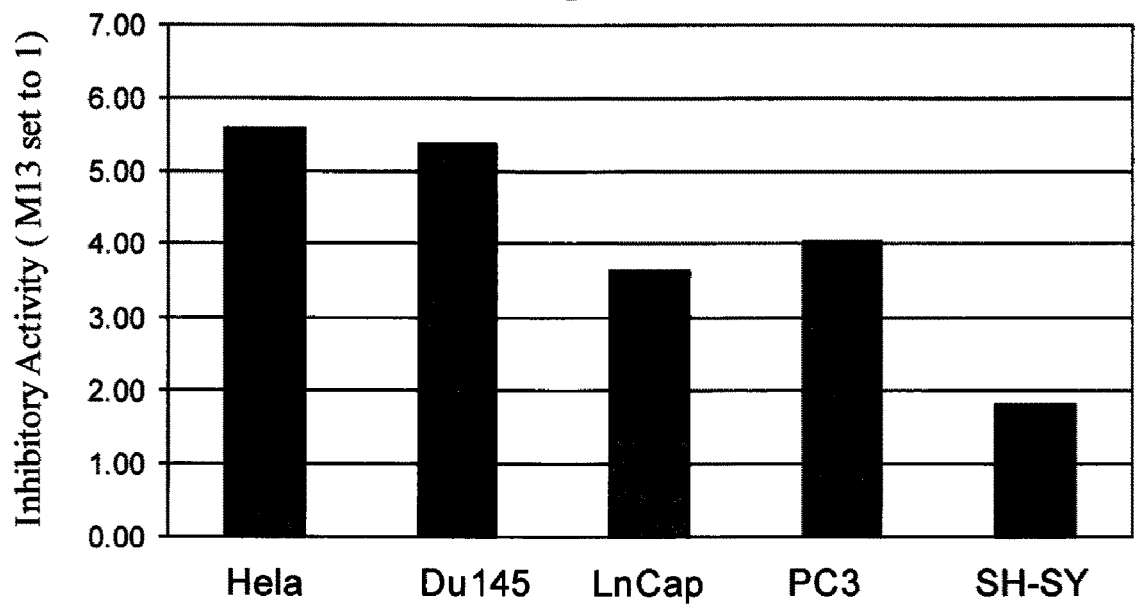
Figure 12

A
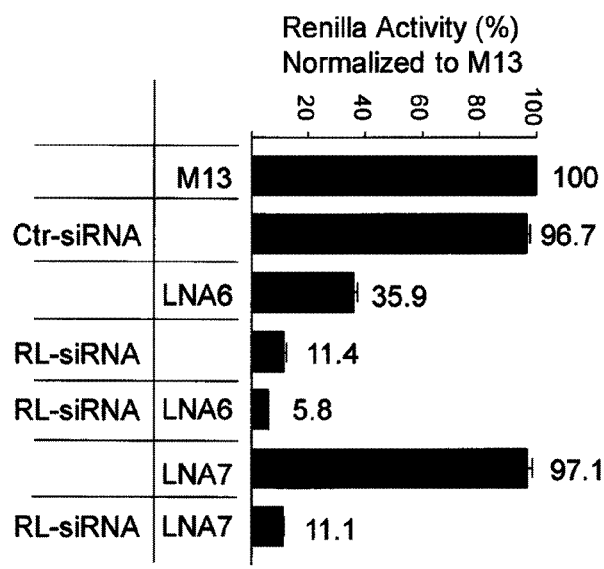
B
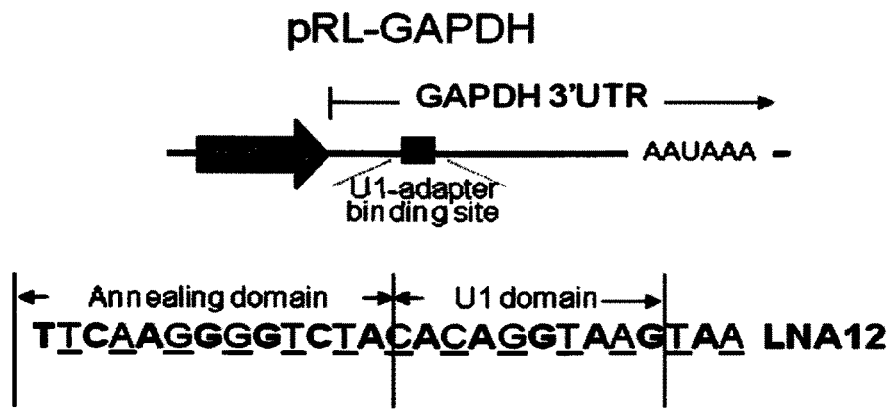
C
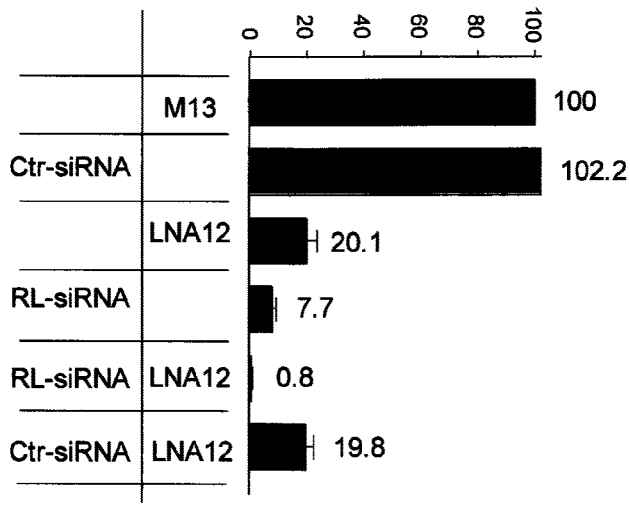
Figure 13

A
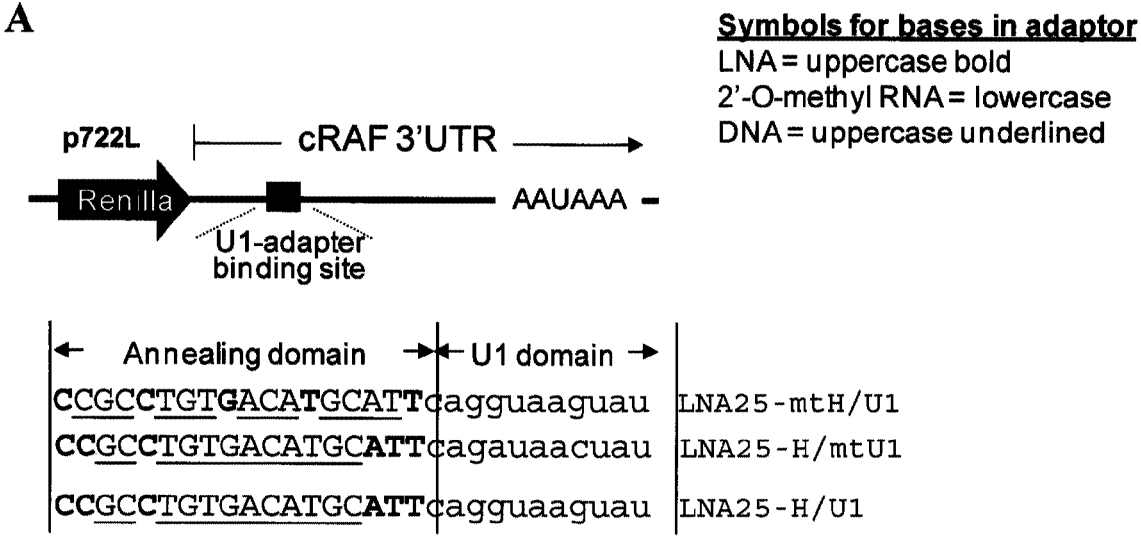
B
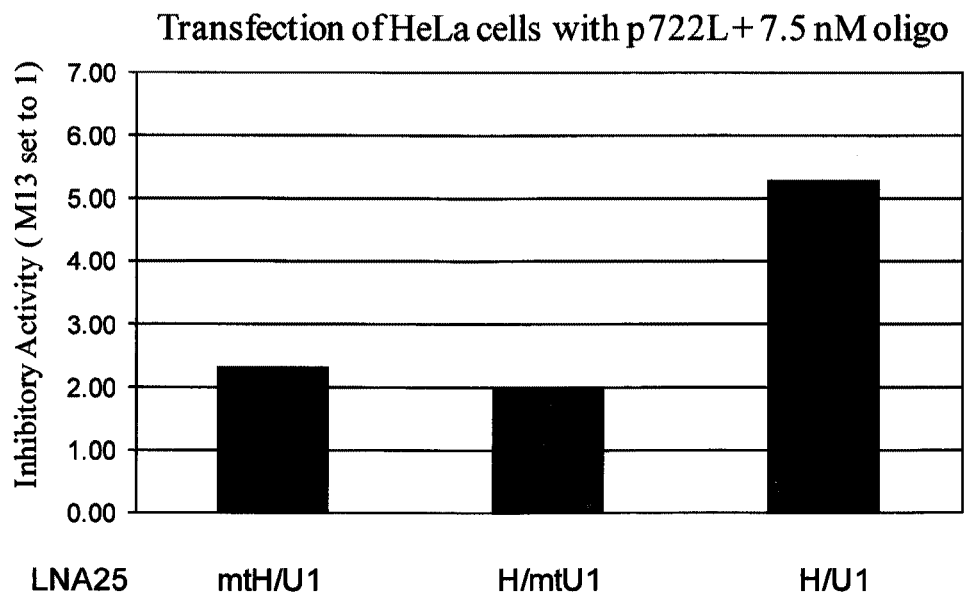
Figure 14

A
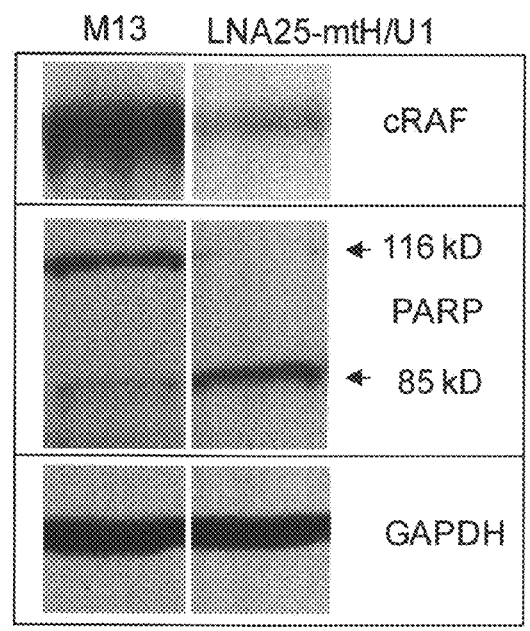
B
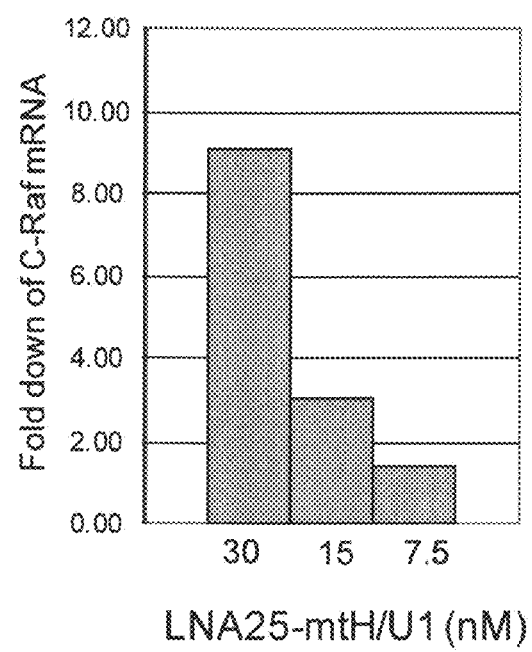
Figure 15

A
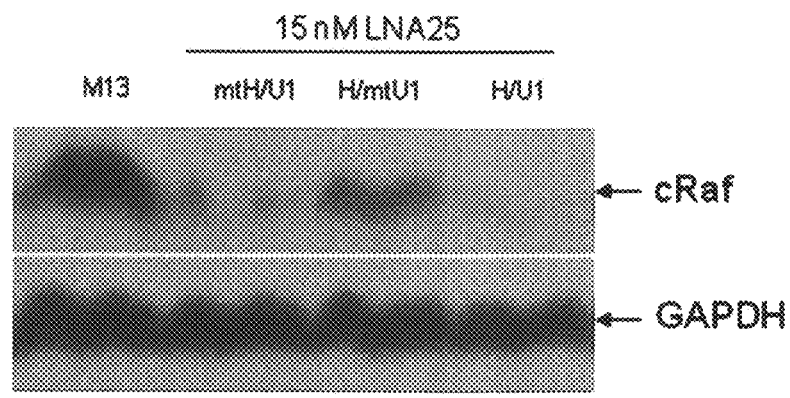
B
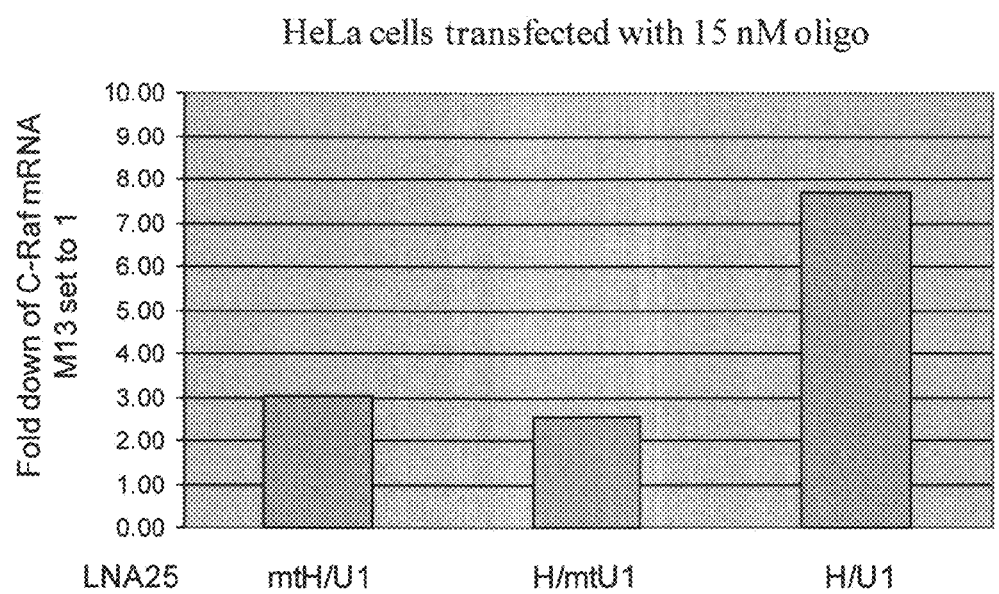
Figure 16

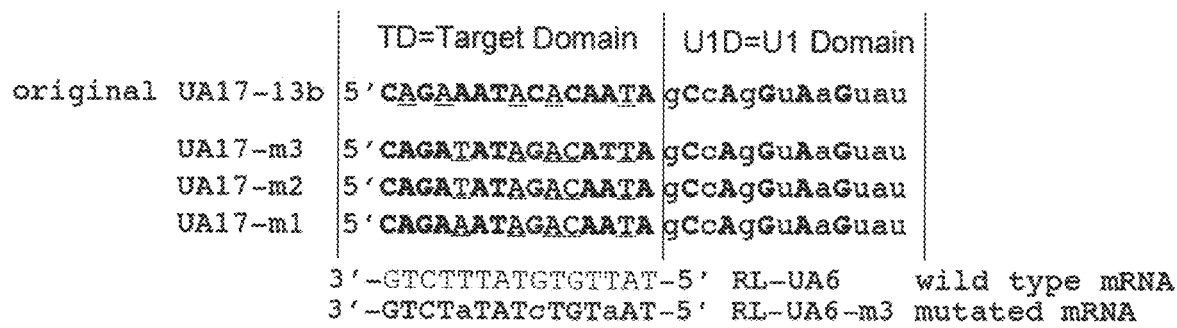
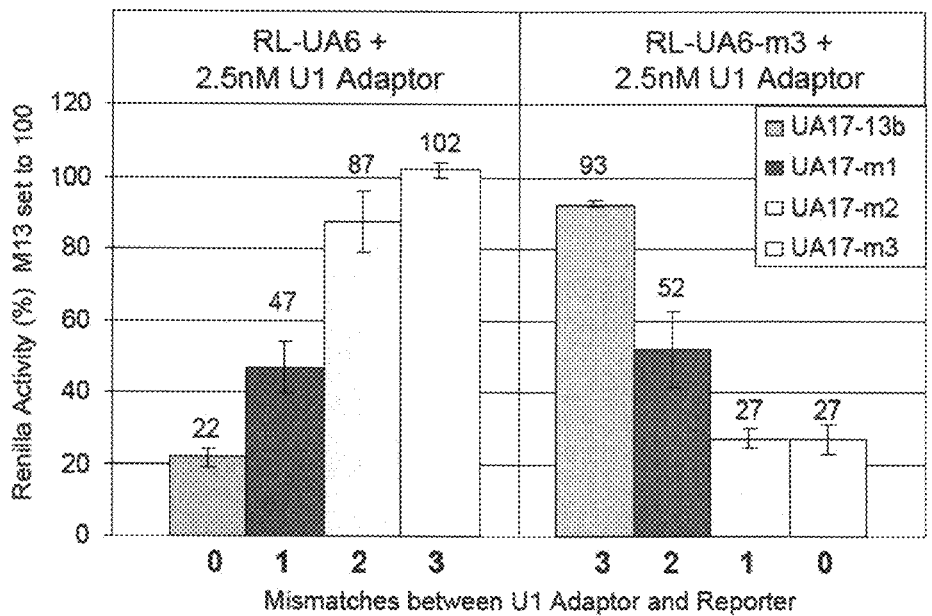
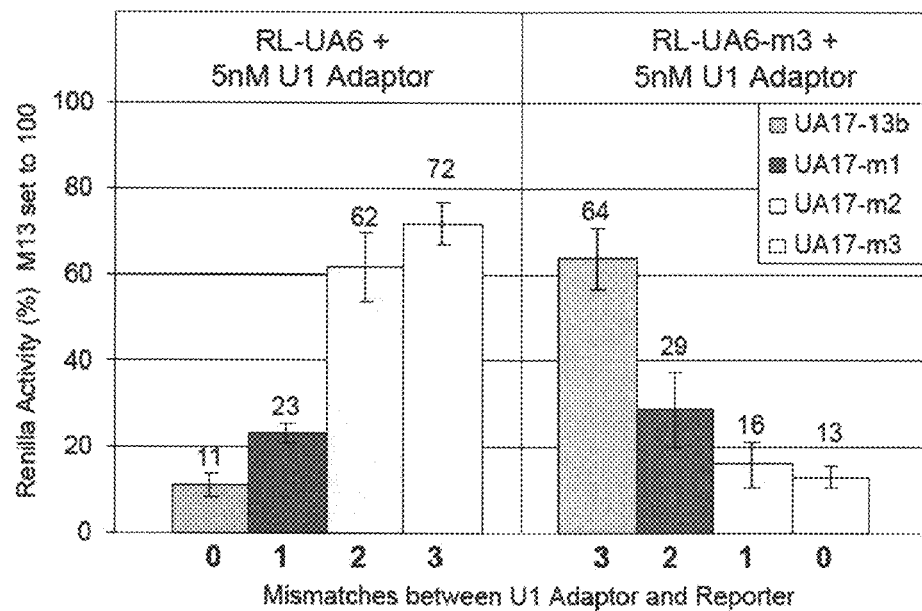
Figure 23

A
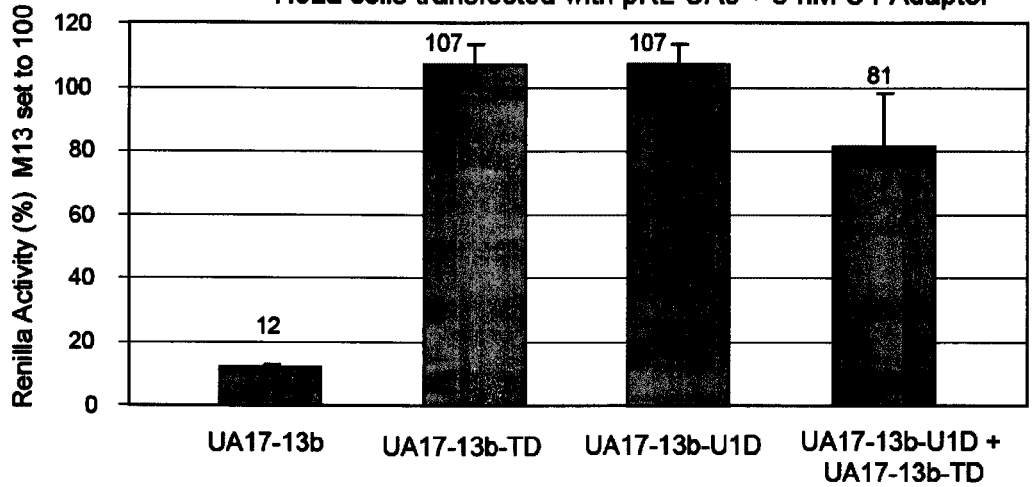
B
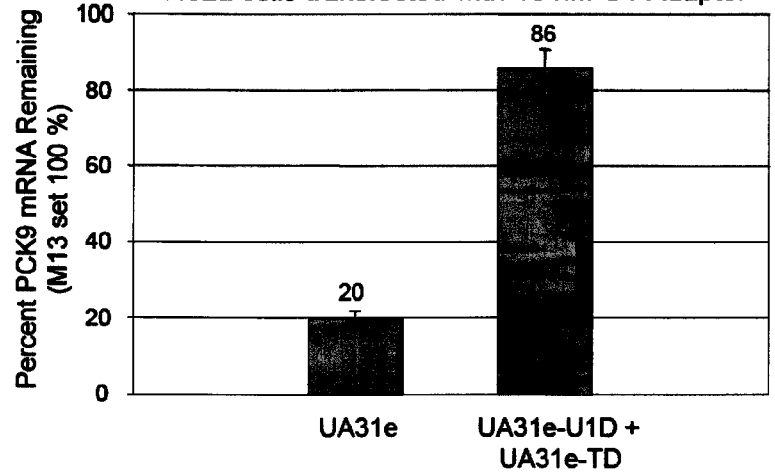
Figure 28 anti-Renilla U1 Adaptors: U1 Domain at 3' end

| | |
|---|---|
| UA6 | CAGAAATACACAATACAGGTAAGTA |
| UA7a | CAGAAATACACAATACAACTCACTA |
| UA7b | CAGAAATACACAATAcagcuaagua |
| UA7c | CAGAAATACACAATAcagcucagua |
| UA-OMe1 | cagaaauacacaauacagguaagua — all 2'OMe |
| UA17-7 | CAGAAATACACAATAcagguaa |
| UA17-8 | CAGAAATACACAATAcagguaag |
| UA17-9 | CAGAAATACACAATAcagguaagu |
| UA17-10 | CAGAAATACACAATAcagguaagua |
| UA17-11 | CAGAAATACACAATAcagguaaguau |
| UA17-12 | CAGAAATACACAATAccagguaaguau |
| UA17-13 | CAGAAATACACAATAgccagguaaguau |
| UA17-13b | CAGAAATACACAATAgCcAgGuAaGuau |
| UA17-14 | CAGAAATACACAATAugccagguaaguau |
| UA17-15 | CAGAAATACACAATAcugccagguaaguau |
| UA17-17 | CAGAAATACACAATAcccugccagguaaguau |
| UA17-19 | CAGAAATACACAATAuccccugccagguaaguau |
| UA17-m3 | CAGATATAGACATTAgCcAgGuAaGuau |
| UA17-m2 | CAGATATAGACAATAgCcAgGuAaGuau |
| UA17-m1 | CAGAAATAGACAATAgCcAgGuAaGuau |
| UA21* | CAGAAATACACAATAcagguaagua |
| UA24-15 | CAGAAATACACAATAcagguaagua |
| UA24-12 | AAATACACAATAcagguaagua |

UA7a, UA7b, UA7c: mutated U1 Domain
UA17-m3, UA17-m2, UA17-m1: mismatch in Target Domain
UA24-15, UA24-12: all LNA Target Domain anti-Renilla U1 Adaptors: U1 Domain at 5' end and both ends

| | |
|---|---|
| UA22* | cagguaaguaCAGAAATACACAATA |
| UA22-11 | cagguaaguauCAGAAATACACAATA |
| UA22-13 | gccagguaaguauCAGAAATACACAATA |
| UA22-15 | cugccagguaaguauCAGAAATACACAATA |
| UA23* | cagguaaguaCAGAAATACACAATAcagguaagua | anti-cRAF1 U1 Adaptors

| | |
|---|---|
| UA25 | CCGCCTGTGACATGCATTcagguaaguau |
| UA25-mt | CCGCCTGTGACATGCATTcagauaacuau — mutated U1 Domain |
| UA27 | TGTCTCCACATCAGGcagguaagua |
| UA28 | AGAGAGTGTTGGAGCcagguaagua |
| UA29 | TATTCCTGGCTTCCTcagguaagua | anti-PCSK9 U1 Adaptors

| | |
|---|---|
| UA31d4 | AGAGGGACAAGTCGGAACCAgccAgGuAagTAu |
| UA31e | CTCGCAGGCCACGGTCACgccAggTaAguAu |

"half" Adaptors

| | |
|---|---|
| UA31e-TD | CTCGCAGGCCACGGTCAC |
| UA31e-U1D | gccAggTaAguAu |
| UA17-13b-TD | CAGAAATACACAATA |
| UA17-13b-U1D | gCcAgGuAaGuau |

| | |
|---|---|
| UA12 | TTCAAGGGGTCTACACAGGTAAGTAA — anti-GAPDH (Fig. S12) |

| | |
|---|---|
| M13 control | GTAAAACGACGGCCAGT |

Figure 34

DsiRNA Sequences

| | | | |
|---|---|---|---|
| PCSK9 | NM_174936 | 5' | CCUAGACACCAGCAUACAGAGUG*AC* |
| | | 3' | GAGGAUCUGUGGUCGUAUGUCUCACUG |
| RAF1 | NM_002880 | 5' | ACCUCACGCCUUCACCUUUAACA*CC* |
| | | 3' | UGUGGAGUGCGGAAGUGGAAAUUGUGG |

RNA=ACGU
DNA=*ACGT*

Figure 35

|  | single or double stranded | cellular compartment | target | enzymatic activity needed | sensitivity to PS backbone modifications* | highest potency IC$_{50}$ | degree of off-target |
|---|---|---|---|---|---|---|---|
| | | Molecular Properties | | | | Functional Properties | |
| siRNA | ds | Cyto | mRNA | Dicer/RISC | Yes | <0.1nM | some |
| ASO | ss | Nucl | pre-mRNA | RNase H | No | 1-10nM | variable |
| U1 Adaptor | ss | Nucl | pre-mRNA | none | No | 1-10nM | N/T |

*PS=phosphorothioate (PS) backbone. siRNAs having a PS backbone alternating with natural nucleotides can maintain activity. ASOs require ≥7 continuous DNA bases in the middle for RNase H. N/T=not tested.

Figure 36

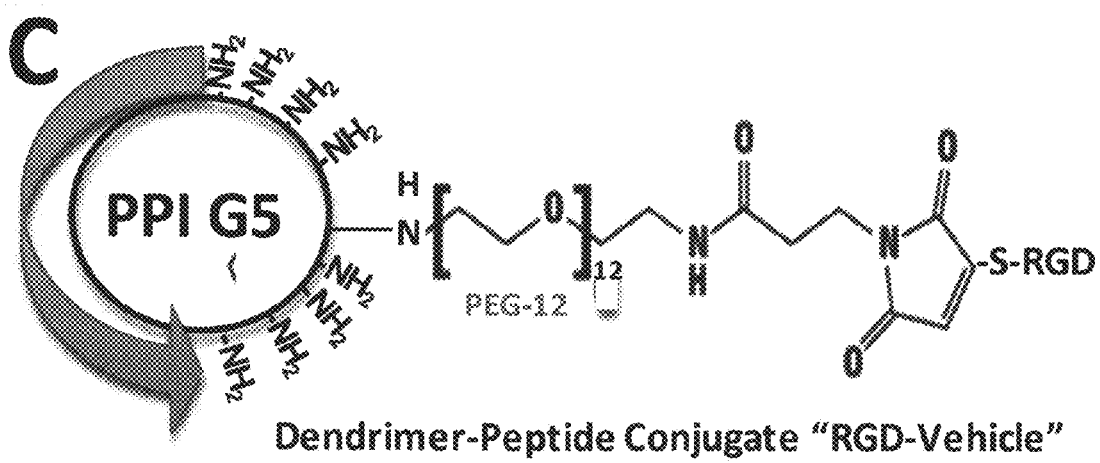
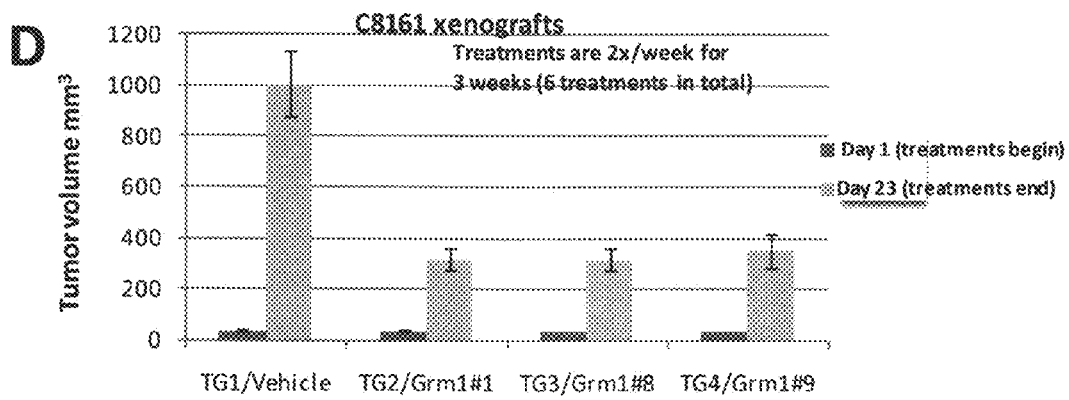
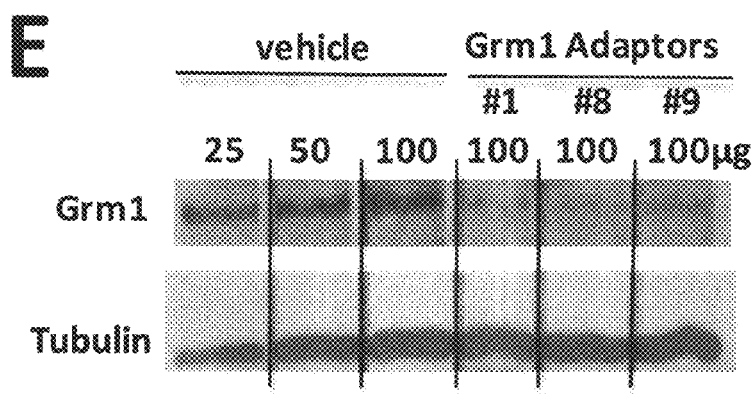
Figure 37

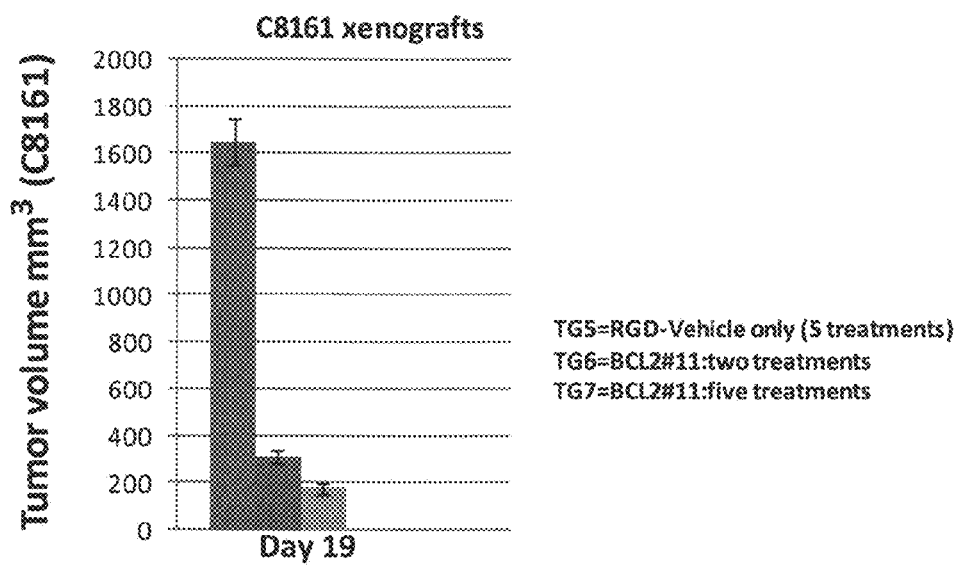
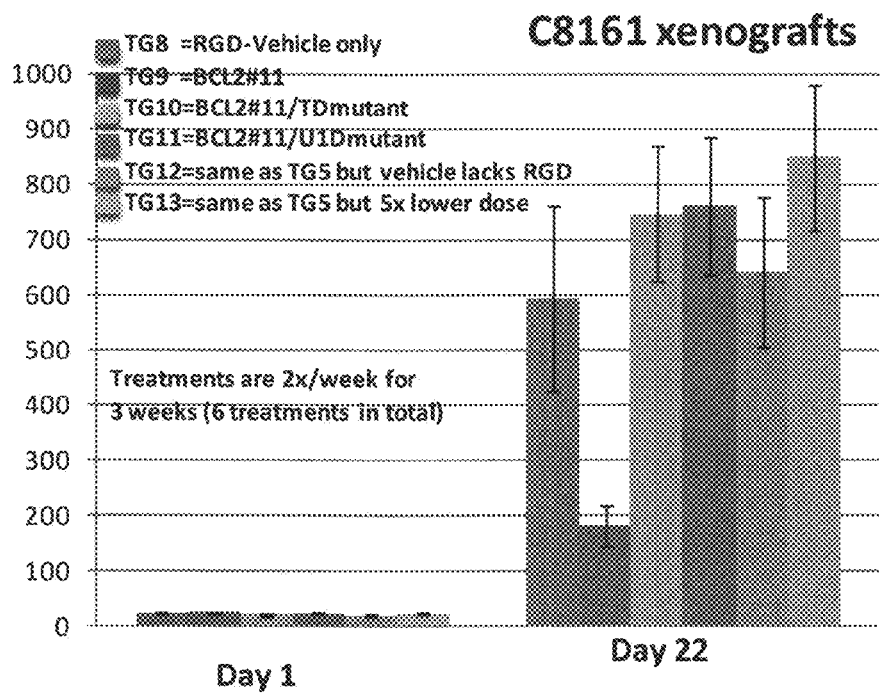
Figure 38

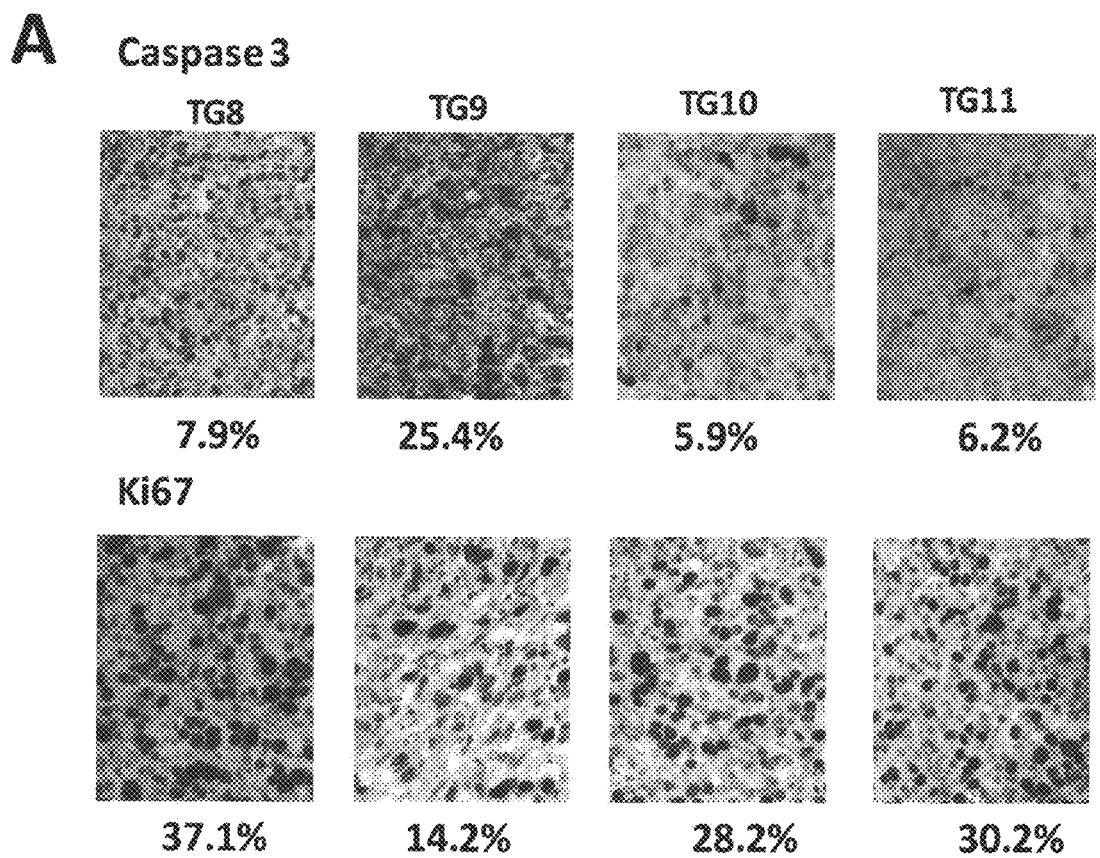
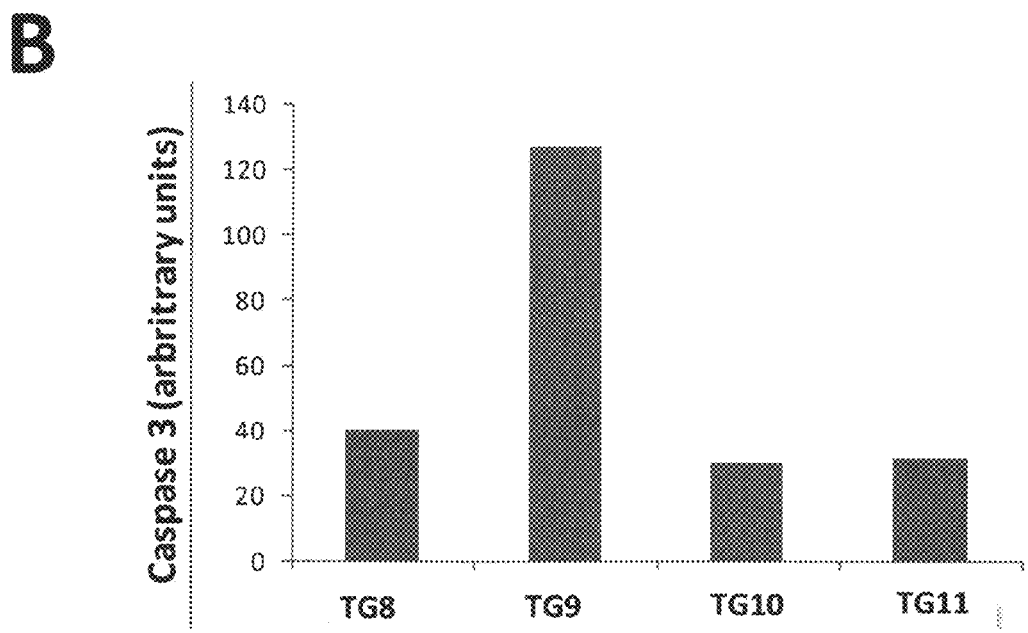
Figure 39

COMPOSITIONS AND METHODS FOR GENE SILENCING

This application is a continuation-in-part of U.S. patent application Ser. No. 12/570,389, filed on Sep. 30, 2009, which claims priority under 35 U.S.C. §119(e) to U.S. Provisional Patent Application No. 61/144,087, filed on Jan. 12, 2009 and is a continuation-in-part of PCT/US2008/058907, filed on Mar. 31, 2008, which claims priority under 35 U.S.C. §119(e) to U.S. Provisional Patent Application No. 60/921,032, filed on Mar. 30, 2007. The foregoing applications are incorporated by reference herein.

Pursuant to 35 U.S.C. §202(c), it is acknowledged that the U.S. Government has certain rights in the invention described herein, which was made in part with funds from the National Institutes of Health, Grant No. R01 GM057286.

FIELD OF THE INVENTION

This invention relates generally to the field of gene silencing. Specifically, the invention provides compositions and methods for regulating the expression of a gene of interest.

BACKGROUND OF THE INVENTION

It has long been appreciated that gene expression can be regulated at the post-transcriptional level, defined to be the steps between transcription initiation and release of the nascent polypeptide from the ribosome. Antisense based approaches encompass a broad variety of techniques, but have in common an oligonucleotide that is designed to base pair with its complementary target mRNA, or more broadly to any RNA, leading to either degradation of the RNA or impaired function (e.g., impaired translation). Classical antisense approaches were designed to interfere with translation of the target mRNA or induce its degradation via Rnase H. Ribozyme-containing antisense molecules also can induce RNA degradation and have the advantage that they can be turned over (i.e., re-used) to cleave more RNA targets. RNAi-based approaches have proven more successful and involve using siRNA to target the mRNA to be degraded (see, e.g., Novina et al. (2004) Nature 430:161-4). However, some mRNAs are only modestly downregulated (2-fold) by RNAi and others are refractory. The 3' end processing (also called polyadenylation, poly(A) tail addition, or cleavage and polyadenylation) of nearly all eukaryotic pre-mRNA comprises two steps: (1) cleavage of the pre-mRNA followed by (2) the synthesis of a poly(A) tail at the 3' end of the upstream cleavage product. 3' end formation is essential to mRNA maturation and, in this sense, is as important as transcription initiation for producing a functional mRNA. 3' end formation also functions to enhance transcription termination, transport of the mRNA from the nucleus, and mRNA translation and stability (Eckner et al. (1991) EMBO J., 10:3513-3522; Sachs et al. (1993) J. Biol. Chem., 268:22955-8). Defects in mRNA 3' end formation can profoundly influence cell growth, development and function (see, e.g., Zhao et al. (1999) Microbiol. Mol. Biol. Rev., 63:405-445; Proudfoot et al. (2002). Cell 108:501-12).

Cleavage and polyadenylation requires two elements. The highly conserved AAUAAA sequence (also called the poly(A) signal or the hexanucleotide sequence) is found 10 to 30 nucleotides upstream of the cleavage site. This hexanucleotide is essential for both cleavage and polyadenylation and any point mutations (with the exception of AUUAAA) result in a large decrease in its activity (Proudfoot et al. (1976) Nature 263:211-4; Sheets et al. (1990) Nucl. Acids Res., 18:5799-805). However, recent bioinformatic studies have suggested that single-base variants or more-rarely double-base variants of AWUAAA (W=A or U) are allowed (Beaudoing et al. (2000) Gen. Res. 10:1001-1010; Tian et al. (2005) Nuc. Acids Res., 33:201-12).

The second element is a less-conserved U- or GU-rich region approximately 30 nucleotides downstream of the cleavage site and thus is called the downstream sequence element (DSE). Point mutations or small deletions do not greatly influence DSE's function. Nevertheless, the proximity of the DSE to the poly(A) site can affect the choice of the cleavage site and the efficiency of cleavage (Zhao et al. (1999). Microbiol. Mol. Biol. Rev., 63:405-445). The cleavage site itself (usually referred to as the pA site or poly(A) site) is selected mainly by the distance between the AAUAAA signal and the DSE (Chen et al. (1995). Nuc. Acids Res., 23:2614-2620). For most genes, cleavage happens after a CA dinucleotide.

In addition to the above signals, auxiliary sequences have also been found to have a positive or negative modulatory activity on 3' end processing.

The cleavage/polyadenylation machinery is composed of multiple protein factors with some having multiple subunits. The endonucleolytic cleavage step involves Cleavage/Polyadenylation Specificity Factor (CPSF) binding to A(A/U)UAAA and Cleavage stimulatory Factor (CstF) binding the DSE. Other required factors include Cleavage Factors 1 and 2 (CF $I_m$ and CF $II_m$), RNA polymerase II (Pol II), Symplekin, and poly(A) polymerase (PAP), although the absolute requirement for PAP is still unclear. Once cleavage has occurred the downstream pre-mRNA fragment is rapidly degraded whereas the upstream fragment undergoes poly(A) tail addition that requires CPSF, PAP, and poly(A)-binding protein II (PAB II).

In principle, having the ability to switch on or off a gene's poly(A) site or sites is a way to directly control expression of that gene. There are natural examples where a gene's expression can be controlled by dialing up or down the poly(A) site. Perhaps the best understood example involves excess U1A protein negatively autoregulating its own synthesis by inhibiting polyadenylation of its own pre-mRNA. Without a poly(A) tail, the mRNA fails to leave the nucleus and is degraded leading to lower levels of U1A mRNA and U1A protein. The mechanism involves 2 molecules of U1A protein binding to a site just upstream of its own pre-mRNA's poly(A) site with the resulting $(U1A)_2$-pre-mRNA complex inhibiting 3'-end processing of the U1A pre-mRNA by inhibiting the polyadenylation activity of PAP (Boelens et al. (1993) Cell 72:881-892; Gunderson et al. (1994) Cell 76:531-541; Gunderson et al. (1997) Genes Dev., 11:761-773). An illustrative example, albeit artificial, of "dialing" is found in Guan et al. (Mol. Cell. Biol. (2003) 23:3163-3172). Guan et al. demonstrate that endogenous U1A protein levels are dialed up or down by dialing up or down the activity of its poly(A) site through a stably-expressed epitope-tagged U1A protein that is under the control of a Tet-regulated promoter. The epitope-tagged U1A protein is not subject to autoregulation because its expression cassette lacks the autoregulatory 3'UTR element.

Another natural example of dialing a poly(A) site involves U1 snRNP binding to a "U1 site" just upstream of the poly(A) site of the bovine papillomavirus type 1 (BPV1) late gene pre-mRNA (Furth et al. (1994) Mol. Cell. Biol., 14: 5278-5289). The term "U1 site", which stands for U1 snRNP binding site, is used so as to distinguish it from U1 snRNP's better known function in 5' splice site (5'ss) binding during pre-mRNA splicing. U1 snRNP consists of 10 proteins in complex with a 164 nucleotide U1 snRNA that base pairs to the BPV1 U1 site via nucleotides 2-11 of U1 snRNA (see, e.g., Will et al. (1997) Curr. Opin. Cell Biol., 9:320-8), notably the same nucleotides 2-11 also basepair to the 5'ss sequence as part of the splicing mechanism. Subsequent to its discovery in BPV1, mechanistic studies demonstrated the U1-70K component of the U1 snRNP directly binds to and inhibits the polyadenylation activity of poly(A) polymerase (Gunderson, et al. (1998) Mol. Cell 1:255-264), the enzyme that adds the poly(A) tail. Additional studies in vivo that eliminated the U1-70K binding site confirmed U1-70K as the effector subunit that inhibits expression (Beckley et al. (2001) Mol. Cell. Biol., 21:2815-25; Sajic et al. (2007) Nuc. Acids Res., 35:247-55).

The U1in gene silencing technologies use 5'-end-mutated U1 snRNA (see, e.g., U.S. Patent Application Publication Nos. 2003/0082149 and 2005/0043261). U1in stands for U1 snRNP inhibition of expression and refers to two recently developed gene silencing technologies that involve expression of a 5'-end-mutated U1 snRNA where nucleotides 2-11 of U1 snRNA are complementary to a 10 nucleotide sequence in the target gene's 3' terminal exon. The 5'-end-mutated U1 snRNA is expressed from a U1 snRNA expression cassette containing promoter elements and a 3' end formation signal from the U1 snRNA gene. The 5'-end-mutated U1 snRNA transcript assembles with the canonical U1 snRNP proteins into a 5'-end-mutated U1 snRNP that then binds to and inhibits polyadenylation of the targeted pre-mRNA. The 3 key features to make U1in silencing work are: (1) the U1 site on the target pre-mRNA and the 5'-end-mutated U1 snRNA must be perfectly complementary across all 10 basepairs, as a single base mismatch is sufficient to lose silencing (Liu et al. (2002) Nuc. Acids Res., 30:2329-39), (2) the U1 site must be in the 3' terminal exon of the target pre-mRNA (Beckley et al. (2001) Mol. Cell. Biol., 21:2815-25; Fortes et al. (2003) Proc. Natl. Acad. Sci., 100:8264-8269), and (3) the U1-70K binding site on the U1 snRNA must be intact. Although U1in has been successfully used in several instances, its development as a widely-used technology has been limited for a variety of reasons.

In view of the foregoing, it is clear that there is still a need for methods of regulating gene expression.

SUMMARY OF THE INVENTION

In accordance with the instant invention, nucleic acid molecules for inhibiting the expression of a gene of interest are provided. In a particular embodiment, the nucleic acid molecules comprise an annealing domain operably linked to at least one effector domain, wherein the annealing domain hybridizes to the pre-mRNA of the gene of interest and wherein the effector domain hybridizes to the U1 snRNA of U1 snRNP.

In accordance with another aspect of the invention, methods are provided for inhibiting the expression of a gene of interest comprising delivering to a cell at least one of the nucleic acid molecules of the instant invention.

In accordance with another aspect of the invention, compositions are provided which comprise at least one of the nucleic acid molecules of the invention and at least one pharmaceutically acceptable carrier.

In still another aspect, vectors encoding the nucleic acid molecules of the instant invention are also provided.

In accordance with another aspect of the instant invention, methods of treating, inhibiting, and/or preventing a cancer in a subject are provided.

BRIEF DESCRIPTIONS OF THE DRAWING

FIG. 1A is a schematic of a U1 adaptor oligonucleotide depicting its 2 domains: an annealing domain to base pair to the target gene's pre-mRNA in the 3' terminal exon and an effector domain that inhibits maturation of the pre-mRNA via binding of endogenous U1 snRNP. The provided sequence of the effector domain is SEQ ID NO: 1. FIG. 1B is a schematic of the U1 adaptor annealing to target pre-mRNA. FIG. 1C is a schematic of the U1 adaptor binding U1 snRNP, which leads to poly(A) site inhibition. Ψ=pseudouridines of the U1 snRNA in the U1 snRNP. The provided sequence of the U1 snRNA in the U1 snRNP is SEQ ID NO: 2.

FIG. 2A provides schematics of (1) p717B, comprising a standard *Renilla* reporter with its 3'UTR and poly(A) signal sequences replaced with those from the human MARK1 gene that has a naturally occurring U1 site (SEQ ID NO: 1), and (2) p717ΔB, which matches p717B except for a 4 nucleotide mutation (lowercase letters in SEQ ID NO: 4) in the U1 site. Relative expression levels of the plasmids upon transient expression in HeLa cells along with a Firefly luciferase control are shown, indicating the wild type U1 site represses expression by 30-fold. FIG. 2B provides a schematic of a U1 adaptor inhibiting *Renilla luciferase* expression. The p717ΔB *Renilla* reporter with a MARK1 3'UTR having a mutated U1 site (SEQ ID NO: 5) was co-transfected with LNA6 (SEQ ID NO: 6), a U1 adaptor designed to inhibit the poly(A) site via binding of endogenous U1 snRNP (SEQ ID NO: 2). The bold font indicates LNA bases to increase annealing. LNA7 (SEQ ID NO: 7) is a control that matches LNA6 except for mutation of the effector domain. The LNA6 and LNA7 binding site is indicated by the shaded box.

FIG. 3A is a graph of the inhibitory activity of LNA6 and LNA7 on the *Renilla* reporter. Grey bars are LNA6, white bars are LNA7, and the black bar is M13. FIG. 3B provides a graph of the inhibitory activity of LNA6 as a function of concentration. Values are normalized to the M13 control oligo. $IC_{50}$=Inhibitory Concentration needed to achieve 50% inhibition. The bottom curve is the inhibition of p717ΔB and the top curve is the inhibition of the SV40 reporter having the 15 nucleotide isolated LNA6 binding site (gray box in FIG. 3C). FIG. 3C provides schematics of p717ΔB and pRL-LNA6.

FIG. 4A provides schematics of pRL-LNA6 and pRL-(LNA6)$_2$. FIG. 4B provides a graph demonstrating the inhibitory activity of LNA6 U1 adaptor on plasmids containing one or two LNA6 binding sites. Values are normalized to the LNA7 control oligo. The top curve is the inhibition of the pRL-LNA6 plasmid and the bottom curve is the inhibition of the pRL-(LNA6)$_2$ plasmid.

FIG. 5A is a schematic of a U1 adaptor (LNA13; SEQ ID NO: 13) designed to target the C-raf-1 pre-mRNA by targeting a 3'UTR sequence. The bold font indicates LNA bases to increase annealing. The U1 snRNP sequence is SEQ ID NO: 2 and the flanking and LNA13 binding site is SEQ ID NO: 12. FIG. 5B is a graph depicting the inhibitory activity of varying concentrations of LNA13 on C-raf-1 mRNA as measured by Q-PCR and normalized to GAPDH.

FIG. 6A provides a schematic of the *Renilla* reporter pRL-wtC-Raf-1 (also called p722L) with a C-raf-1 3'UTR and sequences past the poly(A) site, and a graph depicting the $IC_{50}$ values for LNA13 inhibition of pRL-wtC-Raf-1 expression. FIG. 6B provides a schematic of plasmid pRL-LNA13 which has a single binding site for LNA13, and a graph depicting the inhibition of expression by LNA13 as a function of concentration.

FIG. 7A provides the sequences of LNA6 (SEQ ID NO: 6), LNA17 (SEQ ID NO: 14), Ome-1 (SEQ ID NO: 15), and Ome-5 (SEQ ID NO: 16). FIG. 7B provides a graph of the inhibitory activity of 60 nM of adaptors co-transfected with the pRL-wtC-raf-1 plasmid or the pRL-SV40 control plasmid into HeLa cells.

FIG. 8A provides the sequences of LNA17 (SEQ ID NO: 14), LNA21 (SEQ ID NO: 17), LNA22 (SEQ ID NO: 18), and LNA23 (SEQ ID NO: 19). FIG. 8B provides a graph of the inhibitory activity of adaptor variants of LNA17 having phosphorothioate (PS) bonds and different attachment sites for the U1 domain by co-transfection with pRL-LNA6 (p782J) in HeLa cells.

FIG. 9A provides the sequences of LNA17 (SEQ ID NO: 14), LNA24/15 (SEQ ID NO: 20), and LNA24/12 (SEQ ID NO: 21). FIG. 9B provides a graph depicting the inhibitory activity of LNA17, LNA24/15, and LNA24/12.

FIG. 10 provides a schematic of pRL-wtC-raf-1 and the sequences of LN13 (SEQ ID NO: 13) and LNA25-mtH/U1 (SEQ ID NO: 22). The inhibitory activity of 30 nM of adaptors co-transfected with the pRL-wtC-raf-1 plasmid into HeLa cells is also provided.

FIG. 11A provides a schematic of p782J and the sequences of LNA6 (SEQ ID NO: 6), LNA17-13 (SEQ ID NO: 23), LNA17-12 (SEQ ID NO: 24), LNA17-11 (SEQ ID NO: 25), LNA17-10 (SEQ ID NO: 14), LNA17-9 (SEQ ID NO: 26), LNA17-8 (SEQ ID NO: 27), and LNA17-7 (SEQ ID NO: 28). FIG. 11B provides a graph of the inhibitory activity of 30 nM of adaptors co-transfected with the pRL-LNA6 plasmid into HeLa cells.

FIG. 12 provides a schematic of pRL-LNA6 and a graph depicting the inhibitory activity of LNA17-11 adaptor when transfected into different cells lines. DU145 and PC3 are human cell lines originally derived from more aggressive prostate cancers, whereas LnCap was derived from a less aggressive prostate cancer. SH-SY5Y is a human brain cell line.

FIG. 13A provides a graph depicting the inhibition activity with the combination of co-transfected siRNA and U1 adaptors. FIG. 13B provides a schematic of pRL-GADPH and the sequence of LNA12 (SEQ ID NO: 29). FIG. 13C provides a graph depicting the inhibition activity of the combination of co-transfected siRNA and U1 adaptors.

FIG. 14A provides a schematic of p722L and the sequences of LNA-mtH/U1 (SEQ ID NO: 22), LNA25-H/mtU1 (SEQ ID NO: 30), and LNA25-H/U1 (SEQ ID NO: 31). FIG. 14B provides a graph depicting the inhibitory activity of the combination in one oligonucleotide of U1 Adaptor activity and Rnase H activity (i.e., traditional antisense design).

FIG. 15A provides images of Western blots of 40 µg of total protein extracts from HeLa cells transfected in 6 well plates with 30 nM oligonucleotide. The proteins were separated on 12% SDS-PAGE and probed with mouse cRAF, PARP, and GAPDH antibodies. FIG. 15B provides a graph depicting the Q-PCR with C-raf-1-specific primers with the data normalized to GAPDH mRNA.

FIG. 16A provides Western blots of transfected HeLa cells lysed in SDS buffer and probed with mouse cRAF and GAPDH antibodies. FIG. 16B provides a graph depicting Q-PCR with C-raf-1-specific primers with the data normalized to GAPDH mRNA.

FIGS. 17A-17D demonstrate U1 Adaptor inhibition of Renilla is at the level of reduced mRNA. FIGS. 17A and 17B are images of RPA analysis of 3 µg total RNA from untransfected HeLa cells or co-transfected with pRL-UA6 and 30 nM of each oligonucleotide, either the M13 control, the UA6 Adaptor, the UA7a control Adaptor or the UA17-13 Adaptor, as indicated. After 24 hours, the cells were harvested and split into two portions, one to measure Luciferase and the other to make total RNA used for RPAs with either a Renilla-specific probe (FIG. 17A lanes 1-10) or a GAPDH-specific probe (FIG. 17B lanes 1-9). Note that Lanes 1-8 and 10 of FIG. 17A are the same total RNA samples as lanes 1-8, and 10 in FIG. 17B. Lane 9 is blank so as to separate the stronger signal in lane 10 from lane 8. The lanes marked "Msp Marker" are a $^{32}$P-end-labeled Msp digest of pBR322 with the sizes of the bands indicated. The lane marked "cytoplasmic M13" is total RNA from the cytoplasmic fraction of M13 transfected cells prepared as described (Goraczniak et al. (2008) J. Biol. Chem., 283:2286-96). FIG. 17C is an image of an RPA analysis as in FIG. 17A, but with varying amounts of total RNA as indicated. FIG. 17 G is a graph of the quantitation of RPA protected bands and a comparison with the corresponding Renilla Luciferase activities. Both the RPA and Luciferase values were normalized to M13 that was set to 100%.

FIG. 18 is an image of the detection by EMSA of the UA6 Adaptor tethering U1 snRNP to the target RNA. A $^{32}$P-uniformly labeled RNA (~300 nt), called UA6 RNA, was made by T7 RNA Polymerase in vitro run off transcription from a PCR template amplified from pRL-UA6 containing the UA6 binding site. $^{32}$P-UA6 RNA (1 pmol) was mixed either with highly purified HeLa cell U1 snRNP, a U1 Adaptor, or both and the resulting complexes resolved by 6% native PAGE in 1×TBE containing 5% glycerol. The purification of U1 snRNP and its use in EMSA was previously described (Abad et al. (2008) Nucleic Acids Res., 36:2338-52; Gunderson et al. (1998) Molecular Cell, 1:255-264).

FIG. 19 provides a graph which shows the affect of increasing the length of the U1 Domain. The UA17 Adaptor series has the same Target Domain as the UA6 Adaptor and has a U1 Domain made of 100% 2'OMe RNA. Length of the U1 Domain varies from 7 nts (UA17-7 Adaptor) to 19 nts (UA17-19 Adaptor). LNA nucleotides are bold uppercase, DNA nucleotides are underlined uppercase, and 2'OMe RNA nucleotides are lowercase. 15 nM of each U1 Adaptor was co-transfected with pRL-UA6 into HeLa cells and inhibitory activities calculated. The UA7b and UA7c Adaptors are negative controls bearing a single (7b) or double (7c) mutation in the U1 Domain. The sequences provided are SEQ ID NO: 6, SEQ ID NO: 34, SEQ ID NO: 35, SEQ ID NO: 36, SEQ ID NO: 37, SEQ ID NO: 23, SEQ ID NO: 24, SEQ ID NO: 25, SEQ ID NO: 14, SEQ ID NO: 26, SEQ ID NO: 27, SEQ ID NO: 28, SEQ ID NO: 38, and SEQ ID NO: 39, from top to bottom.

FIG. 20 demonstrates the activity of various UA17 Adaptors correlates with their affinity to U1 snRNP. Shown is an EMSA-based competition assay for U1 snRNP binding between various unlabeled UA17 Adaptors and the $^{32}$P-U1D-RNA having an 11 nt U1 Domain (5'CAGGUAAGUAU3'; SEQ ID NO: 32). 0.75 pmoles of purified HeLa cell U1 snRNP was mixed with 0, 1 or 3 pmoles of various unlabeled UA17 Adaptors (the competitor) and incubated for 20 minutes at 30° C. Next 0.5 pmoles of $^{32}$P-labeled U1D-RNA was added and incubated for 10 min at 30° C. and then the complexes resolved by native PAGE. Lane 1 contains no U1 snRNP and no competitor whereas lane 2 contains no unlabeled UA17 competitor Adaptor. The U1 snRNP:$^{32}$P-U1D-RNA complex in lane 2 was set to 100% as the reference. The numbers in the center of the autoradiogram are values relative to the lane 2 reference. The panel on the left is a lighter exposure of lanes 1-4 so as to visualize that the UA17-7 competitor Adaptor had no detectable effect on the amount of complex formation. The competition assay was repeated 3× with similar results.

FIG. 21 provides a graph demonstrating the affect of placing the U1 Domain at the 5' end of the Adaptor. The UA22 Adaptor series matches UA17 except the relative position of the U1 and Target Domains are reversed so that the U1 Domain is positioned at the 5' end. Transfections and analysis are as in FIG. 19. The graph summarizes the results of testing the UA22 series side-by-side with the corresponding UA17 series. The sequences provided are SEQ ID NO: 40, SEQ ID NO: 41, and SEQ ID NO: 42, from top to bottom.

FIG. 22 provides a graph demonstrating the affect of substituting LNA nucleotides into the U1 Domain. The inhibitory activity of UA17-13 (SEQ ID NO: 23), the most active U1 Adaptor from FIG. 19, was compared with a matching Adaptor UA17-13b (SEQ ID NO: 43), which has five LNA nucleotides in the U1 Domain.

FIG. 23 demonstrates the specificity assessed by a mutation/compensatory mutation analysis. Three U1 Adaptors, UA17-m1 (SEQ ID NO: 46), UA17-m2 (SEQ ID NO: 45), and UA17-m3 (SEQ ID NO: 44), are shown that match UA17-13b (SEQ ID NO: 43) except they have 1, 2 or 3 nt mismatches (in lighter font) to the target sequence in the pRL-UA6 "wild type" reporter (SEQ ID NO: 47). These three U1 Adaptors also have a slightly altered configuration of LNA-DNA nucleotides when compared to UA17-13b which was necessary to avoid high self annealing scores that could potentially reduce activity. The activity of each of these four U1 Adaptors was determined by transfection into HeLa cells with either the pRL-UA6 reporter or the pRL-UA6-m3 reporter (SEQ ID NO: 48), the latter restoring perfect complementarity to the UA17-m3 Adaptor. Two concentrations of U1 Adaptors were used (2.5 nM in the upper panel and 5 nM in the lower panel) and the results are from 3 independent experiments.

FIGS. 24A and 24B demonstrate that U1 Adaptors have no effect on splicing of a reporter gene. FIG. 24A depicts pcDNA3.1+, a standard mammalian expression vector, which was modified by inserting a ~3000 bp segment of the human Fibronectin (FN) gene (spanning exons III7b to III8a that includes ~2300 nt intron). The 3'UTR and polyA site sequences are derived from the bovine growth hormone gene. pFN-1for has a 15 nt UA6 binding site inserted in the forward orientation about ~300 nts into the intron while pFN-1αv has the UA6 binding site inserted at the same position but in the reverse orientation. pFN-2for and pFN-2rev are like pFN-1for and pFN-1rev, respectively, but the binding site was inserted ~270 nt upstream of the 3'ss boundary. pFN-3for and pFN-3rev are like pFN-1for and pFN-1rev, respectively, but the binding site was inserted in the terminal exon. pFN-4for and pFN-4rev are like pFN-1for and pFN-1rev, respectively, but the binding site was inserted in the first exon. For FIG. 24B, each of the pFN plasmids was transfected into HeLa cells either with 5 nM UA17-13b Adaptor (the most active U1 Adaptor targeting the UA6 binding site) or 5 nM M13 control oligonucleotide and after 24 hours the cells were harvested and analyzed by RT-PCR. The T7 and BGH primers were specific to the reporter as no band was detected in the untransfected control cells (lanes 11 and 22). Also shown is the RT-PCR amplification of the endogenous Arf1 gene so as to control for the quality of the RNA sample and the RT-PCR.

FIGS. 25A-25C demonstrate the inhibition of the endogenous RAF1 gene. FIG. 25A shows the design of the UA25 Adaptor (SEQ ID NO: 22) that targets the human RAF1 gene. UA25-mt (SEQ ID NO: 49) is a control Adaptor that matches UA25 except for a 2 nt mutation in the U1 Domain. Symbols are as in FIG. 19. FIG. 25 is an image of a Western blot with an anti-RAF1 antibody demonstrating the UA25 Adaptor specifically silenced RAF1 protein in a dose dependent manner when transfected into HeLa cells. The same blot was striped and reprobed with anti-GAPDH antibody to control for equal loading. The same set of transfected cells was split into two with one part being analyzed by Western blotting and the other by qPCR. FIG. 25 C is a graph of a qPCR analysis demonstrating that RAF1 silencing by the UA25 Adaptor occurs at the mRNA level. qPCR was performed and levels of RAF1 mRNA were normalized to the internal standard GAPDH mRNA. Results in FIGS. 25B and 25C are from 3 independent transfections.

FIGS. 26A and 26B demonstrate the inhibition of RAF1 with three different anti-RAF1 U1 Adaptors. FIG. 26A shows the design of three anti-RAF1 U1 Adaptors. FIG. 26B shows a Western blot of total cell lysates (25 μg/lane) from cells transfected with 30 nM of the anti-RAF1 U1 Adaptors using M13 oligonucleotide as a control. The sequences provided are SEQ ID NO: 50, SEQ ID NO: 51, and SEQ ID NO: 52, from top to bottom.

FIGS. 27A and 27B demonstrate the inhibition of the endogenous PCSK9 gene and enhanced inhibition with multiple Adaptors. FIG. 27A shows the sequences of two anti-PCSK9 U1 Adaptors. FIG. 27B is a graph showing the anti-PCSK9 U1 Adaptors were transfected alone or together into HeLa cells. After 24 hours total RNA was harvested and analyzed by qPCR to measure silencing of PCSK9. Results are from 3 independent transfections. The sequences provided are SEQ ID NO: 53 and SEQ ID NO: 54, from top to bottom.

FIGS. 28A and 28B demonstrate that the separation of the U1 and Target Domains inactivates U1 Adaptors. Based on the UA17-13b (SEQ ID NO: 43) design (targeting *Renilla Luciferase*), two "half" Adaptors were synthesized: UA17-13b-TD (SEQ ID NO: 55) has only the Target Domain (TD) and UA17-13b-U1D (SEQ ID NO: 56) has only the U1 Domain (U1D) (FIG. 28A). Co-transfection of 5 nM of each half Adaptor alone or together gave no significant inhibition of the pRL-UA6 reporter as compared to the M13 control (FIG. 28A). In contrast, transfection of the UA17-13b Adaptor gave an 88% level of inhibition of *Renilla* in agreement with what was obtained previously. Based on the UA31e (SEQ ID NO: 54) design (targeting endogenous PCSK9), two "half" Adaptors were synthesized where UA31e-TD (SEQ ID NO: 57) has only the Target Domain (TD) and Ua31e-U1D (SEQ ID NO: 58) has only the U1 Domain (U1D) (FIG. 28B). Co-transfection of 5 nM of each half Adaptor alone or together gave no significant reduction of endogenous PCSK9 mRNA as compared to the M13 control (FIG. 28B). In contrast, transfection of the UA31e Adaptor gave an 80% level of inhibition in agreement with results shown previously.

FIGS. 29A and 29B demonstrate the co-transfection of U1 Adaptors and a siRNA results in enhanced silencing. FIG. 29A is a graph demonstrating the co-transfection of the UA17-13b Adaptor and an anti-Renilla siRNA (RL-siRNA) with the reporter construct pRL-UA6 into HeLa cells gives enhanced silencing as compared to transfection of either the U1 Adaptor or the siRNA alone. pRL-UA6rev is a control plasmid where the U6 binding site is in the reverse orientation and so should not be inhibited by the UA17-13b Adaptor if inhibition occurs at the mRNA level. FIG. 29B is a graph showing that the co-transfection of the anti-RAF1 UA25 Adaptor with an anti-RAF1 Dicer-substrate siRNA (DsiRNA) gives enhanced silencing of the endogenous RAF1 gene as compared to transfection of either the U1 Adaptor or the siRNA alone. Western blotting to detect RAF1 confirmed enhanced inhibition is also seen at the protein level. Results in FIGS. 29A and 29B are from 3 independent transfections.

FIGS. 30A and 30B demonstrate that the co-transfection of U1 Adaptors and siRNAs gives enhanced silencing. FIG. 30A shows the design of an anti-GAPDH UA12 Adaptor (SEQ ID NO: 29) and a *Renilla* reporter called pRLGAPDH having its 3'UTR and polyA signal sequences derived from those of the human GAPDH gene. Transfection analysis of UA12's inhibitory activity on pRL-GAPDH expression gave an $IC_{50}$ of 1.8 nM (FIG. 30A). Co-transfection of the UA12 Adaptor and an anti-Renilla siRNA (RL-siRNA) with pRLGAPDH into HeLa cells gives enhanced silencing as compared to transfection of the U1 Adaptor or the siRNA alone (FIG. 30B). The control siRNA (Ctr-siRNA) had no effect.

FIGS. 31A and 31B demonstrate that the co-transfection of U1 Adaptors and a siRNA gives enhanced silencing of the endogenous PCSK9 gene. FIG. 31A shows the design of two anti-PCSK9 U1 Adaptors. Co-transfection of the two anti-PCSK9 U1 Adaptors and an anti-PCSK9 siRNA into HeLa cells for 24 hours gives enhanced silencing as compared to transfection of the U1 Adaptors or the siRNA alone (FIG. 30B). The sequences provided are SEQ ID NO: 53 and SEQ ID NO: 54, from top to bottom.

FIGS. 32A and 32B depict global expression analysis comparing U1 Adaptors to siRNAs. The total RNAs from the M13, DsiRNA and U1 Adaptor transfections were analyzed by microarray with the Affymetrix human U133A chip and the R2:R1 and R3:R1 ratios calculated for all the genes (FIG. 32A). The fold-reduction in PCSK9 levels obtained by microarray is compared to the values obtained by qRT-PCR. FIG. 32B provides a comparison plot of the genes that showed ≧2-fold change for the R2:R1 ratio (anti-PCSK9 DsiRNA) and the R3:R1 ratio (anti-PCSK9 U1 Adaptors). The line represents the ≧2-fold affected genes from the U1 Adaptor transfection that are sorted from the largest increase to the largest decrease. The other lines represent the corresponding genes but from the DsiRNA transfection. If both the U1 Adaptor and siRNA methods were perfectly specific then the lines would perfectly overlap.

FIG. 33 demonstrates that U1 Adaptors have no apparent effect on alternative splicing pattern of certain genes. The panels show four RT-PCRs that detect alternative splicing of 4 endogenous genes (Cdc25B, Cdc25C, Grb2 and Fibronectin). For all panels, lanes 1-3 are the same RNAs shown that were transfected with 5 nM M13 (lane 1) or 5 nM each of UA31d4 and UA31e (lane 2) or 5 nM anti-PCSK9 siRNA (lane 3). Uniform RT-PCR bands for the Arf1 housekeeping gene were observed for these samples demonstrating the RNA samples and the RT-PCR were of similar quality.

FIG. 34 provides a list of the U1 Adaptor sequences used in this work. The U1 Adaptor names, sequences and the target mRNA are indicated. The U1 Domain is in lighter font, the Target Domain in black. U1 Adaptors from the same series were aligned according to their Target Domains. The asterisk indicates a matching Adaptor has been tested that has a 100% phosphorothioate backbone. All Adaptors were manufactured by IDT (Coralville, Iowa) and purified by HPLC prior to use. The sequences provided are SEQ ID NO: 6, SEQ ID NO: 7, SEQ ID NO: 38, SEQ ID NO: 39, SEQ ID NO: 15, SEQ ID NO: 28, SEQ ID NO: 27, SEQ ID NO: 26, SEQ ID NO: 14, SEQ ID NO: 25, SEQ ID NO: 24, SEQ ID NO: 23, SEQ ID NO: 43, SEQ ID NO: 37, SEQ ID NO: 36, SEQ ID NO: 35, SEQ ID NO: 34, SEQ ID NO: 44, SEQ ID NO: 45, SEQ ID NO: 46, SEQ ID NO: 17, SEQ ID NO: 20, SEQ ID NO: 21, SEQ ID NO: 59, SEQ ID NO: 40, SEQ ID NO: 41, SEQ ID NO: 42, SEQ ID NO: 60, SEQ ID NO: 22, SEQ ID NO: 49, SEQ ID NO: 50, SEQ ID NO: 51, SEQ ID NO: 52, SEQ ID NO: 53, SEQ ID NO: 54, SEQ ID NO: 57, SEQ ID NO: 58, SEQ ID NO: 55, SEQ ID NO: 56, SEQ ID NO: 29, and SEQ ID NO: 61, from top to bottom.

FIG. 35 provides a list of the siRNA sequences used herein. The DsiRNA sequences and their target mRNAs are indicated and were manufactured by IDT (Coralville, Iowa). The anti-Renilla siRNA and Ctr-siRNA were purchased from ABI/Ambion. The sequences provided are SEQ ID NO: 62, SEQ ID NO: 63, SEQ ID NO: 64, and SEQ ID NO: 65, from top to bottom.

FIG. 36 provides a comparison of U1 Adaptor with siRNA and ASO Methods.

FIG. 37A provides sequences of the anti-Grm1 Adaptors (top to bottom: SEQ ID NOs: 77-79). All 33 nts are 2'O-methyl RNA. The underlined nucleotides indicate these positions have PS bonds as explained in the text. The position number indicates in nucleotides where the U1 Adaptor is targeting in the terminal exon of the human Grm1 gene. The terminal exon corresponds to nucleotides 3131-6854 of GenBank Accession No. NM_000838, for example 852 means 852 nts into the terminal exon and would be nt 3982 of GenBank Accession No. NM_000838. FIG. 37B provides a Western blot of transfected C8161 cultured cells probed with an anti-GRM1 antibody (SDIX, Newark, Del.) or a tubulin antibody as a loading control. GAPDH was also probed and shows equal loading. 1 million cells were loaded per lane. Transfections were 60 hours. The Western blot was repeated three independent times with similar results. The transfection was also repeated 3 independent times with similar results. FIG. 37C provides a schematic of the predicted structure of the RGD-Vehicle. FIG. 37D provides a graph of tumor suppression observed in mouse C8161 xenografts. FIG. 37E provides a Western blot of protein lysates from tumors from the FIG. 37D mice. Probing is as in FIG. 37B.

FIG. 38A provides sequences of the anti-BCL2#11 Adaptors and control U1 Adaptors (top to bottom: SEQ ID NOs: 80-82). All 33 nts are 2'O-methyl RNA. The BCL2#11 target site begins 5 nts into the terminal exon of the human BCL2 gene GenBank Accession No. NM_000633 (terminal exon spans 1078-6492). FIG. 38B provides a graph of the tumor suppression observed in mouse C8161 xenografts. FIG. 38C provides a graph of tumor suppression observed in mouse C8161 xenografts.

FIG. 39A provides a representative example of immunohistochemistry of tumor samples from the FIG. 38C mice. The upper row of panels is immunostained for caspase-3, an indicator of apoptosis, while the lower row is immunostained for Ki67, an indicator of proliferation. The percentage values indicate the percent of cells that stained positive. FIG. 39B provides a graphic representation of the number of caspase-3-positive cells as determined by immunostaining. 10 fields were counted with the number of positive cells per field indicated.

DETAILED DESCRIPTION OF THE INVENTION

Figure 2:
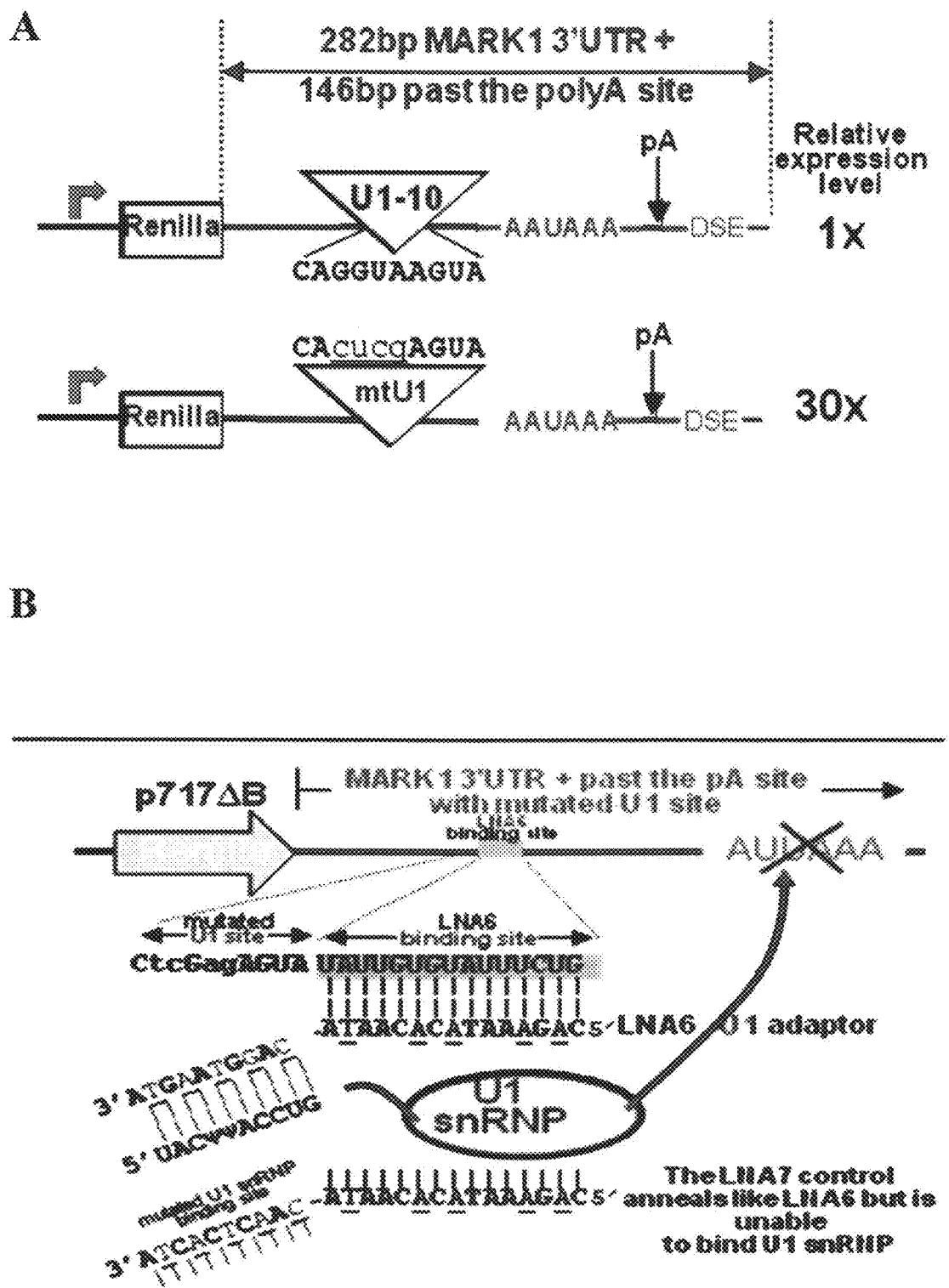

Provided herein are methods and compositions for the modulation of the expression of a gene of interest. The methods comprise the use of the U1 adaptor molecule (see, generally, FIG. 1). In its simplest form, the U1 adaptor molecule is an oligonucleotide with two domains: (1) an annealing domain designed to base pair to the target gene's pre-mRNA (e.g., in the terminal exon) and (2) an effector domain (also referred to as the U1 domain) that inhibits 3'-end formation of the target pre-mRNA via binding endogenous U1 snRNP. Without being bound by theory, the U1 adaptor tethers endogenous U1 snRNP to a gene-specific pre-mRNA and the resulting complex blocks proper 3' end formation. Notably, U1 snRNP is highly abundant (1 million/mammalian cell nucleus) and in stoichiometric excess compared to other spliceosome components. Therefore, there should be no deleterious effects of titrating out endogenous U1 snRNP.

Preferably, the overall U1 adaptor molecule is resistant to nucleases and is able to enter cells either alone or in complex with delivery reagents (e.g., lipid-based transfection reagents). The U1 adaptor oligo should also be capable of entering the nucleus to bind to pre-mRNA. This property has already been established in those antisense approaches that utilize the Rnase H pathway where the oligo enters the nucleus and binds to pre-mRNA. Additionally, it has been showed that antisense oligos can bind to nuclear pre-mRNA and sterically block access of splicing factors leading to altered splicing patterns (Ittig et al. (2004) Nuc. Acids Res., 32:346-53).

The annealing domain of the U1 adaptor molecule is preferably designed to have high affinity and specificity to the target site on the target pre-mRNA (e.g., to the exclusion of other pre-mRNAs). In a preferred embodiment, a balance should be achieved between having the annealing domain too short, as this will jeopardize affinity, or too long, as this will promote "off-target" effects or alter other cellular pathways. Furthermore, the annealing domain should not interfere with the function of the effector domain (for example, by base pairing and hairpin formation). The U1 adaptor annealing domain does not have an absolute requirement on length. However, the annealing domain will typically be from about 10 to about 50 nucleotides in length, more typically from about 10 to about 30 nucleotides or about 10 to about 20 nucleotides. In a particular embodiment, the annealing domain is at least about 13 or 15 nucleotides in length. The annealing domain may be at least 75%, at least 80%, at least 85%, at least 90%, at least 95%, at least 97%, or, more preferably, 100% complementary to the gene of interest. In one embodiment, the annealing domain hybridizes with a target site within the 3' terminal exon, which includes the terminal coding region and the 3'UTR and polyadenylation signal sequences (e.g., through the polyadenylation site). In another embodiment, the target sequence is within about 500 basepair, about 250 basepair, about 100 basepair, or about 50 bp of the poly(A) signal sequence.

In a particular embodiment, the U1 adaptor may comprise at least one nucleotide analog. The nucleotide analogs may be used to increase annealing affinity, specificity, bioavailability in the cell and organism, cellular and/or nuclear transport, stability, and/or resistance to degradation. For example, it has been well-established that inclusion of Locked Nucleic Acid (LNA) bases within an oligonucleotide increases the affinity and specificity of annealing of the oligonucleotide to its target site (Kauppinen et al. (2005) Drug Discov. Today Tech., 2:287-290; Orum et al. (2004) Letters Peptide Sci., 10:325-334). Unlike RNAi and RNase H-based silencing technologies, U1 adaptor inhibition does not involve enzymatic activity. As such, there is significantly greater flexibility in the permissible nucleotide analogs that can be employed in the U1 adaptor analogs when compared with oligos for RNAi and RNase H-based silencing technologies.

Nucleotide analogs include, without limitation, nucleotides with phosphate modifications comprising one or more phosphorothioate, phosphorodithioate, phosphodiester, methyl phosphonate, phosphoramidate, methylphosphonate, phosphotriester, phosphoroaridate, morpholino, amidate carbamate, carboxymethyl, acetamidate, polyamide, sulfonate, sulfonamide, sulfamate, formacetal, thioformacetal, and/or alkylsilyl substitutions (see, e.g., Hunziker and Leumann (1995) Nucleic Acid Analogues: Synthesis and Properties, in Modern Synthetic Methods, VCH, 331-417; Mesmaeker et al. (1994) Novel Backbone Replacements for Oligonucleotides, in Carbohydrate Modifications in Antisense Research, ACS, 24-39); nucleotides with modified sugars (see, e.g., U.S. Patent Application Publication No. 2005/0118605) and sugar modifications such as 2'-O-methyl (2'-O-methylnucleotides) and 2'-O-methyloxyethoxy; and nucleotide mimetics such as, without limitation, peptide nucleic acids (PNA), morpholino nucleic acids, cyclohexenyl nucleic acids, anhydrohexitol nucleic acids, glycol nucleic acid, threose nucleic acid, and locked nucleic acids (LNA) (see, e.g., U.S. Patent Application Publication No. 2005/0118605). See also U.S. Pat. Nos. 5,886,165; 6,140,482; 5,693,773; 5,856,462; 5,973, 136; 5,929,226; 6,194,598; 6,172,209; 6,175,004; 6,166,197; 6,166,188; 6,160,152; 6,160,109; 6,153,737; 6,147,200; 6,146,829; 6,127,533; and 6,124,445.

In a particular embodiment, the U1 domain of the U1 adaptor binds with high affinity to U1 snRNP. The U1 domain may hybridize with U1 snRNA (particularly the 5'-end and more specifically nucleotides 2-11) under moderate stringency conditions, preferably under high stringency conditions, and more preferably under very high stringency conditions. In another embodiment, the U1 domain is perfectly complementary to nucleotides 2-11 of endogenous U1 snRNA. Therefore, the U1 domain may comprise the sequence 5'-CAGGUAAGUA-3' (SEQ ID NO: 1). In another embodiment, the U1 domain is at least 70%, at least 75%, at least 80%, at least 85%, and more preferably at least 90%, at least 95%, or at least 97% homologous to SEQ ID NO: 1. The U1 domain may comprise additional nucleotides 5' or 3' to SEQ ID NO: 1. For example, the U1 domain may comprise at least 1, 2, 3, 4, 5, or up to 10 or 20 nucleotides 5' or 3' to SEQ ID NO: 1. Indeed, as demonstrated hereinbelow, increasing the length of the U1 domain to include basepairing into stem 1 and/or basepairing to position 1 of U1 snRNA improves the U1 adaptor's affinity to U1 snRNP. The effector domain may be from about 8 nucleotides to about 30 nucleotides, from about 10 nucleotides to about 20 nucleotides, or from about 10 to about 15 nucleotides in length. For example, the effector domain may be 8, 9, 10, 11, 12, 13, 14, 15, 16, 17, 18, 19, or 20 nucleotides in length.

The insertion of point mutations into the U1 domain, i.e., diverging from the consensus sequence SEQ ID NO: 1, can moderate silencing. Indeed, altering the consensus sequence will produce U1 domains of different strength and affinity for the U1 snRNA, thereby leading to different levels of silencing. Therefore, once an annealing domain has been determined for a gene of interest, different U1 domains of different strength can be attached to the annealing domain to effect different levels of silencing of the gene of interest. For example gAGGUAAGUA (SEQ ID NO: 3) would bind more weakly to U1 snRNP than SEQ ID NO: 1 and, therefore, would produce a lower level of silencing. As discussed above, nucleotide analogues can be included in the U1 domain to increase the affinity to endogenous U1 snRNP. The addition of nucleotide analogs may not be considered a point mutation if the nucleotide analog binds the same nucleotide as the replaced nucleotide.

Notably, care should be taken so as to not design a U1 adaptor wherein the effector domain has significant affinity for the target site of the mRNA or the sites immediately flanking the target site. In other words, the target site should be selected so as to minimize the base pairing potential of the effector domain with the target pre-mRNA, especially the portion flanking upstream of the annealing site.

To increase the silencing ability of the U1 adaptors, the U1 adaptor should also be designed to have low self annealing so as to prevent the formation of hairpins within a single U1 adaptor and/or the formation of homodimers or homopolymers between two or more U1 adaptors.

The annealing and effector domains of the U1 adaptor may be linked such that the effector domain is at the 5' end and/or 3' end of the annealing domain. Further, the annealing and effector domains may be operably linked via a linker domain. The linker domain may comprise 1, 2, 3, 4, 5, 6, 7, 8, 9, 10, up to 15, up to 20, or up to 25 nucleotides.

In another embodiment of the instant invention, more than one U1 adaptor directed to a gene of interest may be used to modulate expression. As shown hereinbelow, multiple U1 adaptors targeting (annealing) to different sequences in the same pre-mRNA should give enhanced inhibition (as has already been shown in FIG. 9). Compositions of the instant invention may comprise more than one U1 adaptor directed to a particular gene of interest.

In still another embodiment, the U1 adaptor can be combined with other methods of modulating the expression of a gene of interest. For example, a U1 adaptor can be used in coordination with antisense approaches such as, RNase H-based methods, RNAi, and morpholino-based methods to give enhanced inhibition. Inasmuch as U1 adaptors utilize a different mechanism than antisense approaches, the combined use will result in an increased inhibition of gene expression compared to the use of a single inhibitory agent alone. Indeed, U1 adaptors may target the biosynthetic step in the nucleus whereas RNAi and certain antisense approaches generally target cytoplasmic stability or translatability of a pre-existing pool of mRNA.

The U1 adaptors of the instant invention may be administered to a cell or organism via an expression vector. For example, a U1 adaptor can be expressed from a vector such as a plasmid or a virus. Expression of such short RNAs from a plasmid or virus has become routine and can be easily adapted to express a U1 adaptor.

In another aspect of the instant invention, the effector domain of the U1 adaptor can be replaced with the binding site for any one of a number of nuclear factors that regulate gene expression. For example, the binding site for polypyrimidine tract binding protein (PTB) is short and PTB is known to inhibit poly(A) sites. Thus, replacing the effector domain with a high affinity PTB binding site would also silence expression of the target gene.

There are U1 snRNA genes that vary in sequence from the canonical U1 snRNA described hereinabove. Collectively, these U1 snRNA genes can be called the U1 variant genes. Some U1 variant genes are described in GenBank Accession Nos. L78810, AC025268, AC025264 and AL592207 and in Kyriakopoulou et al. (RNA (2006) 12:1603-11), which identified close to 200 potential U1 snRNA-like genes in the human genome. Since some of these these U1 variants have a 5' end sequence different than canonical U1 snRNA, one plausible function is to recognize alternative splice signals during pre-mRNA splicing. Accordingly, the U1 domain of the U1 adaptors of the instant invention may be designed to hybridize with the 5' end of the U1 variant snRNA in the same way as the U1 domain was designed to hybridize with the canonical U1 snRNA as described herein. The U1 adaptors which hybridize to the U1 variants may then be used to modulate the expression of a gene of interest.

There are many advantages of the U1 adaptor technology to other existing silencing technologies. Certain of these advantages are as follows. First, the U1 adaptor separates into two independent domains: (1) the annealing (i.e., targeting) activity and (2) the inhibitory activity, thereby allowing one to optimize annealing without affecting the inhibitory activity or vice versa. Second, as compared to other technologies, usage of two adaptors to target the same gene gives additive even synergistic inhibition. Third, the U1 adaptor has a novel inhibitory mechanism. Therefore, it should be compatible when used in combination with other methods. Fourth, the U1 adaptor inhibits the biosynthesis of mRNA by inhibiting the critical, nearly-universal, pre-mRNA maturation step of poly (A) tail addition (also called 3' end processing).

Although U1in has been successfully used in certain circumstances, its development as a widely-used technology has been limited for a variety of reasons. Certain of these reasons are described as follows.

First, for U1in, there is a possibility that off-target silencing will occur because a 10 nucleotide sequence, even if it is restricted to the terminal exon, may not be long enough to be unique in the human transcriptome or in most vertebrate transcriptomes. The U1 adaptor annealing domain does not have restrictions in length or nucleotide composition (e.g., nucleotide analogues may be used) and so a length of 15 nucleotides, such as was used for LNA6 described hereinbelow, is sufficient for uniqueness in a typical mammalian transcriptome.

Second, for U1in, inhibition is readily negated if the pre-mRNA target sequence is "buried" within intramolecular RNA secondary structure. Indeed, if just half of the 10 nucleotide target (i.e., 5 nucleotides) is base paired, then that is sufficient to block binding of the 5'-end-mutated U1 snRNP as well as endogenous U1 snRNP (Fortes et al. (2003) Proc. Natl. Acad. Sci., 100:8264-8269; Abad et al. (2008) Nucleic Acids Res. (2008) 36: 2338-2352). This important problem of target accessibility is not easily solved and is due in large part to the well-recognized difficulty algorithms have in accurately predicting short mRNA secondary structures. The U1 adaptor effector domain is not masked by RNA structure because it is designed to not base pair with the target pre-mRNA.

Third, for U1in, the 5'-end-mutated U1 snRNA is too long to synthesize as an oligonucleotide and attempts to shorten it while maintaining activity have failed. Thus, 5'-end-mutated U1 snRNA can only be expressed from DNA (e.g., from a plasmid or viral delivery system) that has a suitable U1 snRNA expression cassette. The U1 adaptor is an oligonucleotide that does not have a length restriction and typically is in the range of 20-30 nucleotides in length.

Fourth, for U1in, inhibition by transient transfection of a 5'-end-mutated U1 snRNA plasmid is often inefficient because U1 snRNA maturation takes up to 18 hours, thereby resulting in a significant delay or "lag time" in accumulation of the inhibitory complex, leading to a delay in inhibition of the target gene. The U1 adaptor does not have such a lag time.

Fifth, for U1in, an additional potential concern is that "off-target" effects could arise from basepairing of a 5'-end-mutated U1 snRNP to an internal exon or intron that then alters the splicing pattern or affects other steps in the life of that gene's mRNA. This is exacerbated by the fact that the 10 nucleotide targeting sequence for U1in is so short. This concern is mitigated for the U1 adaptor because it has a much longer targeting sequence that can also be readily altered.

Sixth, the expression levels of the 5' end mutated U1 snRNA (the inhibitory molecule for U1in) are significantly lower than the level of endogenous U1 snRNA (1 million molecules/nucleus) which is the corresponding inhibitory molecule for the U1 adaptor technology. Thus, inhibitory levels of the U1 adaptor should be higher.

Definitions

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" may refer to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989):

$$Tm=81.5° C.+16.6 \text{ Log } [Na+]+0.41(\% G+C)-0.63(\% \text{ formamide})-600/\#bp \text{ in duplex}$$

As an illustration of the above formula, using [Na+]=[0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the oligonucleotide with its target, the hybridization is usually carried out at salt and temperature conditions that are 20-25° C. below the calculated Tm of the hybrid. Wash conditions should be as stringent as possible for the degree of identity of the probe for the target. In general, wash conditions are selected to be approximately 12-20° C. below the Tm of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1× SSC and 0.5% SDS at 65° C. for 15 minutes.

The term "primer" as used herein refers to a DNA oligonucleotide, either single stranded or double stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non complementary nucleotide sequence may be attached to the 5' end of an otherwise complementary primer. Alternatively, non complementary bases may be interspersed within the oligonucleotide primer sequence, provided that the primer sequence has sufficient complementarity with the sequence of the desired template strand to functionally provide a template primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The terms "percent similarity", "percent identity" and "percent homology", when referring to a particular sequence, are used as set forth in the University of Wisconsin GCG software program.

A "replicon" is any genetic element, for example, a plasmid, cosmid, bacmid, phage or virus, which is capable of replication largely under its own control. A replicon may be either RNA or DNA and may be single or double stranded.

A "vector" is a genetic element, such as a plasmid, cosmid, bacmid, phage or virus, to which another genetic sequence or element (either DNA or RNA) may be attached. The vector may be a replicon so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a nucleic acid or a polypeptide coding sequence in a host cell or organism. An "expression vector" is a vector which facilitates the expression of a nucleic acid or a polypeptide coding sequence in a host cell or organism.

The term "oligonucleotide," as used herein, refers to nucleic acid sequences, primers, and probes of the present invention, and is defined as a nucleic acid molecule comprised of two or more ribo or deoxyribonucleotides, preferably more than three. The exact size of the oligonucleotide will depend on various factors and on the particular application and use of the oligonucleotide.

The phrase "small, interfering RNA (siRNA)" refers to a short (typically less than 30 nucleotides long, more typically between about 21 to about 25 nucleotides in length) double stranded RNA molecule. Typically, the siRNA modulates the expression of a gene to which the siRNA is targeted. The term "short hairpin RNA" or "shRNA" refers to an siRNA precursor that is a single RNA molecule folded into a hairpin structure comprising an siRNA and a single stranded loop portion of at least one, typically 1-10, nucleotide.

The term "RNA interference" or "RNAi" refers generally to a sequence-specific or selective process by which a target molecule (e.g., a target gene, protein or RNA) is downregulated via a double-stranded RNA. The double-stranded RNA structures that typically drive RNAi activity are siRNAs, shRNAs, microRNAs, and other double-stranded structures that can be processed to yield a small RNA species that inhibits expression of a target transcript by RNA interference.

The term "antisense" refers to an oligonucleotide having a sequence that hybridizes to a target sequence in an RNA by Watson-Crick base pairing, to form an RNA:oligonucleotide heteroduplex with the target sequence, typically with an mRNA. The antisense oligonucleotide may have exact sequence complementarity to the target sequence or near complementarity. These antisense oligonucleotides may block or inhibit translation of the mRNA, and/or modify the processing of an mRNA to produce a splice variant of the mRNA. Antisense oligonucleotides are typically between about 5 to about 100 nucleotides in length, more typically, between about 7 and about 50 nucleotides in length, and even more typically between about 10 nucleotides and about 30 nucleotides in length.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

The term "gene" refers to a nucleic acid comprising an open reading frame encoding a polypeptide, including both exon and (optionally) intron sequences. The nucleic acid may also optionally include non coding sequences such as promoter or enhancer sequences. The term "intron" refers to a DNA sequence present in a given gene that is not translated into protein and is generally found between exons.

The phrase "operably linked", as used herein, may refer to a nucleic acid sequence placed into a functional relationship with another nucleic acid sequence. Examples of nucleic acid sequences that may be operably linked include, without limitation, promoters, transcription terminators, enhancers or activators and heterologous genes which when transcribed and, if appropriate to, translated will produce a functional product such as a protein, ribozyme or RNA molecule.

"Pharmaceutically acceptable" indicates approval by a regulatory agency of the Federal government or a state government. "Pharmaceutically acceptable" agents may be listed in the U.S. Pharmacopeia or other generally recognized pharmacopeia for use in animals, and more particularly in humans.

A "carrier" refers to, for example, a diluent, preservative, solubilizer, emulsifier, adjuvant, excipient, auxiliary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions may be employed as carriers. Suitable pharmaceutical carriers are described, for example, in "Remington's Pharmaceutical Sciences" by E. W. Martin.

Chemotherapeutic agents are compounds that exhibit anti-cancer activity and/or are detrimental to a cell (e.g., a toxin). Suitable chemotherapeutic agents include, but are not limited to: toxins (e.g., saporin, ricin, abrin, ethidium bromide, diptheria toxin, and Pseudomonas exotoxin); taxanes; alkylating agents (e.g., temozolomide, nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes (e.g., cisplatin, carboplatin, tetraplatin, ormaplatin, thioplatin, satraplatin, nedaplatin, oxaliplatin, heptaplatin, iproplatin, transplatin, and lobaplatin); bioreductive alkylators such as mitomycin, procarbazine, dacarbazine and altretamine); DNA strand-breakage agents (e.g., bleomycin); topoisomerase II inhibitors (e.g., amsacrine, menogaril, amonafide, dactinomycin, daunorubicin, N,N-dibenzyl daunomycin, ellipticine, daunomycin, pyrazoloacridine, idarubicin, mitoxantrone, m-AMSA, bisantrene, doxorubicin (adriamycin), deoxydoxorubicin, etoposide (VP-16), etoposide phosphate, oxanthrazole, rubidazone, epirubicin, bleomycin, and teniposide); DNA minor groove binding agents (e.g., plicamydin); antimetabolites (e.g., folate antagonists such as methotrexate and trimetrexate); pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); anthracyclines; and tubulin interactive agents (e.g., vincristine, vinblastine, and paclitaxel (Taxol®).

Radiation therapy refers to the use of high-energy radiation from x-rays, gamma rays, neutrons, protons and other sources to target cancer cells. Radiation may be administered externally or it may be administered using radioactive material given internally. Chemoradiation therapy combines chemotherapy and radiation therapy.

As used herein, "oncogene" refers to a gene that when it has higher than normal activity (e.g., over-expressed), induces abnormal tissue growth due to effects on the biology of a cell, for example on the cell cycle or cell death process. The term "oncogene" encompasses an overexpressed version of a normal gene in animal cells (the proto-oncogene) that can release the cell from normal restraints on growth (either alone or in concert with other changes), thereby converting a cell into a tumor cell. Examples of human oncogenes include, without limitation: myc, myb, mdm2, PKA-I (protein kinase A type I), Abl, Bcl1, the anti-apoptotic B-cell lymphoma-2 (Bcl-2) family of proteins (Bcl-2, Bcl-XL, Bcl-w, Mcl-1, Bfl1/A-1, and Bcl-B (see, e.g., Kang et al. (Clin. Cancer Res. (2009) 15:1126-32)), Bcl6, Ras, c-Raf kinase, CDC25 phosphatases, cyclins, cyclin dependent kinases (cdks), telomerase, PDGF/sis, erbA, erb-B, ets, fes (fps), fgr, fms, fos, jun, mos, src, proliferating cell nuclear antigen (PCNA), transforming growth factor-beta (TGF-beta), transcription factors nuclear factor kappaB (NF-κB), E2F, HER-2/neu, TGF-alpha, EGFR, TGF-beta, IGFIR, P12, MDM2, c-myb, c-myc, BRCA, Bcl-2, VEGF, MDR, ferritin, transferrin receptor, IRE, HSP27, hst, int1, int2, jun, hit, B-lym, mas, met, mil (raf), mos, neu (ErbB2), ral (mil), Ha-ras, Ki-ras, N-ras, rel, ros, sis, ski, trk, yes and metallothionein genes.

With respect to antibodies, the term "immunologically specific" refers to antibodies that bind to one or more epitopes of a protein or compound of interest, but which do not substantially recognize and bind other molecules in a sample containing a mixed population of antigenic biological molecules.

The term "treat" refers to the ability of the compound to relieve, alleviate, and/or slow the progression of the patient's disease (e.g., cancer). In other words, the term "treat" refers to inhibiting and/or reversing the progression of a disease, such as cancer. The term "treat" includes the inhibition, suppression, and/or regression of a tumor.

Compositions and Methods

Compositions of the instant invention comprise at least one U1 adaptor of the instant invention and at least one pharmaceutically acceptable carrier. The compositions may further comprise at least one other agent which inhibits the expression of the gene of interest. For example, the composition may further comprise at least one siRNA or antisense oligonucleotide directed against the gene of interest.

The U1 adaptors of the present invention may be administered alone, as naked polynucleotides, to cells or an organism, including animals and humans. The U1 adaptor may be administered with an agent which enhances its uptake by cells. In a particular embodiment, the U1 adaptor may be contained within a liposome, nanoparticle, or polymeric composition (see, e.g., U.S. Pat. Nos. 4,897,355; 4,394,448; 4,235,871; 4,231,877; 4,224,179; 4,753,788; 4,673,567; 4,247,411; 4,814,270; 5,567,434; 5,552,157; 5,565,213; 5,738,868; 5,795,587; 5,922,859; and 6,077,663, Behr (1994) Bioconjugate Chem. 5:382-389, and Lewis et al. (1996) PNAS 93:3176-3181).

In another embodiment, the U1 adaptor may be delivered to a cell or animal, including humans, in an expression vector such as a plasmid or viral vector. Expression vectors for the expression of RNA molecules preferably employ a strong promoter which may be constitutive or regulated. Such promoters are well known in the art and include, but are not limited to, RNA polymerase II promoters, the T7 RNA polymerase promoter, and the RNA polymerase III promoters U6 and H1 (see, e.g., Myslinski et al. (2001) Nucl. Acids Res., 29:2502-09). Viral-mediated delivery includes the use of vectors based on, without limitation, retroviruses, adenoviruses, adeno-associated viruses, vaccinia virus, lentiviruses, polioviruses, and herpesviruses.

The pharmaceutical compositions of the present invention can be administered by any suitable route, for example, by injection (e.g., intravenously and intramuscularly), by oral, pulmonary, nasal, rectal, or other modes of administration. The compositions can be administered for the treatment of a disease which can be treated through the downregulation of a gene(s). The compositions may be used in vitro, in vivo, and/or ex vivo.

The compositions, U1 adaptors, and/or vectors of the instant invention may also be comprised in a kit.

The instant invention also encompasses methods of treating, inhibiting (slowing or reducing), and/or preventing a disease or disorder (e.g., cancer) in a subject. In a particular embodiment, the methods comprise the administration of a therapeutically effective amount of at least one composition of the instant invention to a subject (e.g., an animal or human) in need thereof. In a particular embodiment, the composition comprises at least one U1 adaptor of the instant invention and at least one pharmaceutically acceptable carrier. In a particular embodiment, the U1 adaptor is directed to a gene whose over-activity or over-expression is associated with (e.g., the cause of) the disease or disorder, including viral, fungal, or bacterial infections (see, e.g., European Patent Application EP2239329 for targets). For example, U1 adaptors directed against PCSK9 can be used to treat, inhibit, and/or prevent hypercholesterolemia (Frank-Kamenetsky et al. (2008) Proc. Natl. Acad. Sci., 105:11915-20). U1 adaptors directed against Fas (CD95), PTP-1B (protein tyrosine phosphatase 1B), or T cell protein tyrosine phosphatase (TCPTP) can be used to treat, inhibit, and/or prevent diabetes (e.g., type-I or type-II) (Jeong et al. (2010) J. Control Release 143:88-94; Xu et al. (2005) Biochem. Biophys. Res. Commun., 329:538-43; Xu et al. (2007) Cell Biol. Intl., 31:88-91). U1 adaptors directed against TNFα can be used to treat, inhibit, and/or prevent inflammatory diseases (e.g., arthritis) (see also, e.g., targets in Ponnappa, B. C. (2009) Curr. Opin. Investig. Drugs, 10:418-24). U1 adaptors directed against α-synuclein can be used to treat, inhibit, and/or prevent Parkinson's disease (e.g., Lewis et al. (2008) Mol. Neurodegener., 3:19). U1 adaptors directed against amyloid precursor protein (APP) or β-secretase can be used to treat, inhibit, and/or prevent neurological disease such as Alzheimer's disease (e.g., Singer et al. (2005) Nat. Neurosci., 8:1343-1349; Miller et al. (2004) Nucleic Acids Res., 32:661-8).

In a particular embodiment, the U1 adaptor is directed to a cancer gene (e.g., a gene implicated in the cancer to be treated), particularly an oncogene. For example, the cancer may be characterized by over-expression of the cancer gene to be targeted (e.g., an oncogene).

The instant methods may further comprise the administration of at least one other agent which inhibits the expression of the target cancer gene. For example, the method may further comprise the administration of at least one siRNA or antisense oligonucleotide directed against the cancer gene. The methods may also comprise the administration at least one other chemotherapeutic agent or therapy (e.g., radiation). The above agents may be administered in separate compositions (e.g., with at least one pharmaceutically acceptable carrier) or in the same composition. The agents may be administered simultaneously or consecutively.

The U1 adaptor of the composition can be targeted to any cancer gene whose expression is to be inhibited in order to treat, inhibit, and/or prevent the cancer. Examples of cancer genes to be targeted are provided hereinabove and in European Patent Application EP2239329 (see, e.g., 89-97), Futreal et al. (Nature Rev. (2004) 4:177-183 (see, e.g., Supplementary Information S1), Hanahan et al. (Cell (2000) 100: 57-70), and Cui et al. (Molecular Systems Biology (2007) 3:152). Examples of cancer genes to be targeted include, without limitation (examples of types of cancer, without limitation, to be treated in parentheses): BCL2 (melanoma, lung, prostate cancers or Non-Hodgkin lymphoma), GRM1 (melanoma), PDGF beta (testicular and lung cancers), Erb-B (breast cancer), Src (colon cancer), CRK (colon and lung cancers), GRB2 (squamous cell carcinoma), RAS (pancreatic, colon and lung cancers, and leukemia), MEKK (squamous cell carcinoma, melanoma or leukemia), JNK (pancreatic or breast cancers), RAF (lung cancer or leukemia), Erk1/2 (lung cancer), PCNA (p21) (lung cancer), MYB (colon cancer or chronic myelogenous leukemia), c-MYC (Burkitt's lymphoma or neuroblastoma), JUN (ovarian, prostate or breast cancers), FOS (skin or prostate cancers), Cyclin D (esophageal and colon cancers), VEGF (esophageal and colon cancers), EGFR (breast cancer), Cyclin A (lung and cervical cancers), Cyclin E (lung and breast cancers), WNT-1 (basal cell carcinoma), beta-catenin (adenocarcinoma or hepatocellular carcinoma), c-MET (hepatocellular carcinoma), PKC (breast cancer), NFKB (breast cancer), STATS (prostate cancer), survivin (cervical or pancreatic cancers), Her2/Neu (breast cancer), topoisomerase (ovarian and colon cancers), topoisomerase II alpha (breast and colon cancers), p73 (colorectal adenocarcinoma), p21 (WAF1/CIP1) (liver cancer), p27 (KIP1) (liver cancer), PPM1D (breast cancer), RAS (breast cancer), caveolin I (esophageal squamous cell carcinoma), MIB I (male breast carcinoma), MTAI (ovarian carcinoma), M68 (adenocarcinomas of the esophagus, stomach, colon, and rectum), mutant p53 (gall bladder, pancreatic and lung cancers), mutant DN-p63 (squamous cell carcinoma), mutant pRb (oral squamous cell carcinoma), mutant APC1 (colon cancer), mutant BRCA1 (breast and ovarian cancers), mutant PTEN (hamartomas, gliomas, and prostate and endometrial cancers), MLL fusions (acute leukemias), BCR/ABL fusion (acute and chronic leukemias), TEL/AML1 fusion (childhood acute leukemia), EWS/FLI1 fusion (Ewing Sarcoma), TLS/FUS 1 fusion (Myxoid liposarcoma), PAX3/FKHR fusion (Myxoid liposarcoma), and AML1/ETO fusion (acute leukemia).

Cancers that may be treated using the present invention include, but are not limited to: cancers of the prostate, colorectum, pancreas, cervix, stomach, colon, endometrium, brain, liver, bladder, ovary, gall bladder, testis, head, neck, skin (including melanoma and basal carcinoma), mesothelial lining, white blood cell (including lymphoma and leukemia), esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma.

As stated hereinabove, the U1 adaptors of the present invention may be administered alone (as naked polynucleotides) or may be administered with an agent which enhances its uptake by cells. In a particular embodiment, the U1 adaptor may be contained within a delivery vehicle such as a micelle, liposome, nanoparticle, or polymeric composition. In a particular embodiment, the U1 adaptor is complexed with (e.g., contained within or encapsulated by) a dendrimer, particularly cationic dendrimers such as poly(amido amine) (PAMAM) dendrimers and polypropyleneimine (PPI) dendrimers (e.g., generation 3, 4, or 5).

In a particular embodiment, the U1 adaptors are targeted to cancer cells. In a particular embodiment, the U1 adaptor is covalently linked (e.g., directly or via a linker) to at least one targeting moiety. In a preferred embodiment, a complex comprising the U1 adaptor (e.g., a dendrimer, micelle, liposome, nanoparticle, or polymeric composition) is covalently linked (e.g., directly or via a linker) to at least one targeting moiety.

Generally, the linker is a chemical moiety comprising a covalent bond or a chain of atoms that covalently attaches the targeting moiety to the U1 adaptor complex. The linker can be linked to any synthetically feasible position of the targeting moiety and the U1 adaptor complex (vehicle). In a particular embodiment, the linker connects the targeting moiety and the U1 adaptor complex via an amine group and/or sulfhydryl group. In a particular embodiment the linker is attached at a position which avoids blocking the targeting moiety. Exemplary linkers may comprise at least one optionally substituted; saturated or unsaturated; linear, branched or cyclic alkyl group or an optionally substituted aryl group. The linker may also be a polypeptide (e.g., from about 1 to about 20 amino acids, particularly about 1 to about 10 or 1 to about 5). The linker may be biodegradable (cleavable (e.g., comprises a disulfide bond)) under physiological environments or conditions. In a particular embodiment, the linker is polyethylene glycol (PEG). In a particular embodiment, the linker is a SPDP (N-Succinimidyl 3-(2-pyridyldithio)-propionate) linker such as LC-SPDP (Succinimidyl 6-(3-[2-pyridyldithio]-propionamido)hexanoate). The linker may also be non-degradable (non-cleavable) and may be a covalent bond or any other chemical structure which cannot be substantially cleaved or cleaved at all under physiological environments or conditions.

Targeting moieties of the instant invention preferentially bind to cancer cells or the relevant tissue or organ. In a particular embodiment, the targeting moiety specifically binds to a marker specifically (only) expressed on cancer cells or a marker up-regulated on cancer cells compared to normal cells. The targeting moiety may specifically bind to a cancer-specific antigen (e.g., CEA (carcinoembryonic antigen) (colon, breast, lung); PSA (prostate specific antigen) (prostate cancer); CA-125 (ovarian cancer); CA 15-3 (breast cancer); CA 19-9 (breast cancer); HER2/neu (breast cancer); α-feto protein (testicular cancer, hepatic cancer); β-HCG (human chorionic gonadotropin) (testicular cancer, choriocarcinoma); MUC-1 (breast cancer); Estrogen receptor (breast cancer, uterine cancer); Progesterone receptor (breast cancer, uterine cancer); and EGFr (epidermal growth factor receptor) (bladder cancer)). In a particular embodiment, the targeting moiety is an antibody or antibody fragment immunologically specific for a surface protein on cancer cells or a surface protein expressed at higher levels (or greater density) on cancer cells than normal cells, tissues, or organs. In a particular embodiment, the targeting moiety is a ligand or binding fragment thereof for a cell surface receptor on cancer cells. In a particular embodiment, the targeting moiety specifically binds to alpha-5 beta-3 integrin cell surface receptor. In a particular embodiment, the targeting moiety is an RGD peptide or RGD mimic (see, e.g., European Patent Application EP2239329).

The U1 adaptors (including the vehicles comprising the same) described herein will generally be administered to a patient as a pharmaceutical preparation. The terms "patient" and "subject", as used herein, include humans and animals. These U1 adaptors may be employed therapeutically, under the guidance of a physician.

The compositions comprising the U1 adaptors of the instant invention may be conveniently formulated for administration with any pharmaceutically acceptable carrier(s). For example, the U1 adaptors may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the U1 adaptors in the chosen medium may be varied and the medium may be chosen based on the desired route of administration of the pharmaceutical preparation. Except insofar as any conventional media or agent is incompatible with the U1 adaptors to be administered, its use in the pharmaceutical preparation is contemplated.

The dose and dosage regimen of U1 adaptors according to the invention that are suitable for administration to a particular patient may be determined by a physician considering the patient's age, sex, weight, general medical condition, and the specific condition for which the U1 adaptors is being administered and the severity thereof. The physician may also take into account the route of administration, the pharmaceutical carrier, and the U1 adaptors' biological activity.

Selection of a suitable pharmaceutical preparation will also depend upon the mode of administration chosen. For example, the U1 adaptors of the invention may be administered by direct injection to a desired site (e.g., tumor). In this instance, a pharmaceutical preparation comprises the U1 adaptors dispersed in a medium that is compatible with the site of injection. U1 adaptors of the instant invention may be administered by any method. For example, the U1 adaptors of the instant invention can be administered, without limitation parenterally, subcutaneously, orally, topically, pulmonarily, rectally, vaginally, intravenously, intraperitoneally, intrathecally, intracerebrally, epidurally, intramuscularly, intradermally, or intracarotidly. In a particular embodiment, the method of administration is by direct injection (e.g., into the tumor or into the area immediately surrounding the tumor). Pharmaceutical preparations for injection are known in the art. If injection is selected as a method for administering the U1 adaptors, steps must be taken to ensure that sufficient amounts of the molecules or cells reach their target cells to exert a biological effect.

Pharmaceutical compositions containing a U1 adaptor of the present invention as the active ingredient in intimate admixture with a pharmaceutically acceptable carrier can be prepared according to conventional pharmaceutical compounding techniques. The carrier may take a wide variety of forms depending on the form of preparation desired for administration, e.g., intravenous, oral, direct injection, intracranial, and intravitreal.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of U1 adaptors may be determined by evaluating the toxicity of the molecules or cells in animal models. Various concentrations of U1 adaptors in pharmaceutical preparations may be administered to mice, and the minimal and maximal dosages may be determined based on the beneficial results and side effects observed as a result of the treatment. Appropriate dosage unit may also be determined by assessing the efficacy of the U1 adaptors treatment in combination with other standard drugs. The dosage units of U1 adaptors may be determined individually or in combination with each treatment according to the effect detected.

The pharmaceutical preparation comprising the U1 adaptors may be administered at appropriate intervals, for example, at least twice a day or more until the pathological symptoms are reduced or alleviated, after which the dosage may be reduced to a maintenance level. The appropriate interval in a particular case would normally depend on the condition of the patient.

The following examples describe illustrative methods of practicing the instant invention and are not intended to limit the scope of the invention in any way.

Example I

The following methods were used in the Examples II-VIII.

Cultured cells (typically HeLa cells) were grown in media as recommended by ATCC and seeded the day before transfection such that they would be approximately 50% confluent on the day of transfection. For 24-well-plates, mix #1 and #2 were incubated 15 minutes at room temperature and then gently mixed together and incubated another 20 minutes at room temperature. Mix #1 was made by adding oligos (adaptors, siRNAs, and M13) and reporter plasmids to 50 µl OPTI-MEM® media (Invitrogen catalog 51985; Carlsbad, Calif.). Mix #2 was made by adding 1.8 µl LIPOFECTAMINE™-2000 (Invitrogen) to 50 µl OPTIMEM® media. The media on the cells in the 24 well dish was removed and 400 µl of fresh complete media was added. Then all of the Mix 1+2 solution (approximately 110 µl) was added to the cells. For 12-well and 6-well plate transfections, the values listed above were scaled up 2-fold and 4-fold, respectively. For luciferase assays, the cells were harvested after 24 hours or 48 hours and luciferase measured using the Promega dual luciferase kit (Madison, Wis.) and a Turner BioSystems Luminometer (Sunnyvale, Calif.). For inhibition of endogenous genes, the cells were harvested after 24 or up to 48 hours and either lysed in SDS buffer for Western blotting or total RNA made using a Qiagen RNeasy kit (Valencia, Calif.).

Enhanced chemiluminescence (ECL) Western blotting was done as previously described (Gunderson et al. (1997) Genes and Dev., 11:761-773; Gunderson et al. (1998) Mol. Cell 1:255-264). Anti-GAPDH antibody (1:10000 dilution; Chemicon; Temecula, Calif.), a 1:1000 dilution anti-C-raf-1 antibody (R1912 from BD Biosciences; San Jose, Calif.) and a 1:1000 dilution for the anti-PARP antibody (Ab-2 from Oncogene; La Jolla, Calif.) were used. The secondary antimouse and anti-rabbit antibodies were used at a 1:5000 dilution and were obtained from Amersham (Piscataway, N.J.) as was the chemiluminescent reagent. The membrane used was Immobilon-P from Millipore (Bedford, Mass.) and was treated as per manufacturer's instructions.

RNA from transfected cells was isolated using the Rneasy kit from Qiagen. Complimentary DNA was synthesized using 1 µg of RNA, random hexamers, and Moloney Murine Leukemia Virus (MMLV) reverse transcriptase as suggested by the manufacturer (Promega). 50 ng of cDNA was analyzed on real-time PCR using a ROTOR-GENE™ 3000 real time rotary analyzer (Corbett Research; Cambridgeshire, United Kingdom) and QuantiTech SYBR Green PCR kit (Qiagen). Amplification of glyceraldehyde-3-phosphate dehydrogenase (GAPDH) was used as an endogenous control to standardize the amount of sample added to the reaction. The comparative cycle threshold (CT) method was used to analyze the data by generating relative values of the amount of target cDNA. To obtain relative values, the following arithmetic formula was used: $2^{-\Delta\Delta CT}$, where $\Delta CT$=difference between the threshold cycles of the target (c-Raf) and an endogenous reference (GAPDH), and $-\Delta\Delta CT$=difference between $\Delta CT$ of the target sample and a control (cells treated with M13 oligo).

Example II

To facilitate testing of the U1 adaptor, the dual luciferase reporter system from Promega was employed where Firefly luciferase was used as a co-transfected control and *Renilla luciferase* was targeted for inhibition by the U1 adaptor. Plasmid p717B (FIG. 2A) was constructed by taking a Promega *Renilla luciferase* plasmid (pRL-SV40) and replacing its 3'UTR and poly(A) signal sequences with sequences from the human Microtubule Affinity Regulating Kinase (MARK1) 3'UTR and poly(A) signal region including 146 basepairs past the poly(A) site. The human MARK1 3'UTR has a naturally occurring wild type (wt) 10 nucleotide U1 site that is also found in other MARK1 homologs in other vertebrates. The MARK1 wt U1 site in p717B is functional for inhibiting expression. Furthermore, the introduction of a 4 nucleotide mutation in the wt U1 site, thereby producing plasmid p717ΔB, resulted in an approximate 30-fold increase in *Renilla* expression (see FIG. 2A). p717ΔB was tested as it would allow for the comparison of "trans-inhibition" mediated by a U1 adaptor:U1 snRNP complex with the "cis-inhibition" mediated by the MARK1 wt U1 site:U1 snRNP complex.

To target p717ΔB for inhibition, a U1 adaptor (FIG. 2B) called LNA6 that contains a mixture of Locked Nucleic Acid (LNA) nucleotides and phosphoramidate modified bases was used. In theory, any inhibitory activity seen with LNA6 could be due to a combination of two or more activities, namely: (1) the binding of U1 snRNP and (2) traditional antisense effects from its annealing domain, thereby having nothing to do with the effector domain. To distinguish between these activities and facilitate interpretation of the results, a control U1 adaptor called LNA7 was used that matches LNA6 except it is unable to bind endogenous U1 snRNP because of a mutation in the effector domain. Any inhibitory activity seen with LNA7 would arise solely from the action of its annealing domain (antisense activity). Therefore, any observed inhibitory activity with LNA6 that was greater than that observed with LNA7 could be attributed to the binding of U1 snRNP to the effector domain. In other words, comparison of the inhibitory activity of LNA6 with LNA7 would indicate how much inhibition is due to endogenous U1 snRNP binding the effector domain versus inhibition arising solely from traditional antisense effects (e.g., inhibition of translation) that are due to the annealing activity of the annealing domain.

LNA6 was co-transfected with p717ΔB and the control Firefly reporter into HeLa cells and after 24 hours the cells were harvested and luciferase activity measured as per the manufacturer's protocol. Parallel experiments were done where LNA7 was used in place of LNA6. To keep the amount of transfected oligonucleotide constant, an unrelated primer oligonucleotide (the M13 DNA oligonucleotide) was added, where necessary, so that the final amount of total oligonucleotide was held constant at 62 nM. As seen in FIG. 3A, LNA6 gives a dose dependent inhibitory activity and this activity is far higher than that of LNA7. Indeed, testing of higher concentrations of LNA7 (>62 nM) indicated its inhibitory activity is approximately the same as that of the M13 DNA oligonucleotide. Therefore, it is evident that nearly all of the inhibitory activity of LNA6 is due to the action of the effector domain rather than antisense effects just from the annealing domain.

In FIG. 3B, the inhibitory activity of LNA6 is plotted as a function of its concentration and this allows for the calculation of $IC_{50}$ values, i.e., the concentration of oligo needed to achieve 50% inhibition of expression. The $IC_{50}$ value for LNA6 is 6.35 nM. The $IC_{50}$ values were calculated from 3 independent transfections that were plotted as a function of the U1 adaptor concentration (in this case LNA6) and fitted with a sigmoidal dose-response function using GrapPad Prism software.

Given that the MARK1 3'UTR contains a natural U1 site it was possible that MARK1 sequences flanking the LNA6 binding site contribute to LNA6's inhibitory activity. To test this, the LNA6 binding site was analyzed in isolation by inserting its binding site into pRL-SV40, which has its 3'UTR and poly(A) signal sequences derived from SV40, which is unrelated to MARK1. This plasmid is called pRL-LNA6 (FIG. 3C). The co-transfection experiments and analysis above were repeated where pRL-LNA6 was substituted for p717ΔB. It was determined that the $IC_{50}$ value is 6.86 nM which is statistically similar to that seen for the p717ΔB plasmid (FIG. 3B). This demonstrates that the LNA6 binding site is necessary and sufficient to confer LNA6's inhibitory activity to the reporter plasmid.

In additional examples, the time of transfection was varied from 24 to 48 hours and the amount of transfected plasmid was also varied. Similar results to those presented above were obtained.

For each targeting site, it may be desirable to optimize the U1 adaptor design in terms of the number and position of LNA bases so as to give optimal inhibition while minimizing off target effects.

Figure 4:
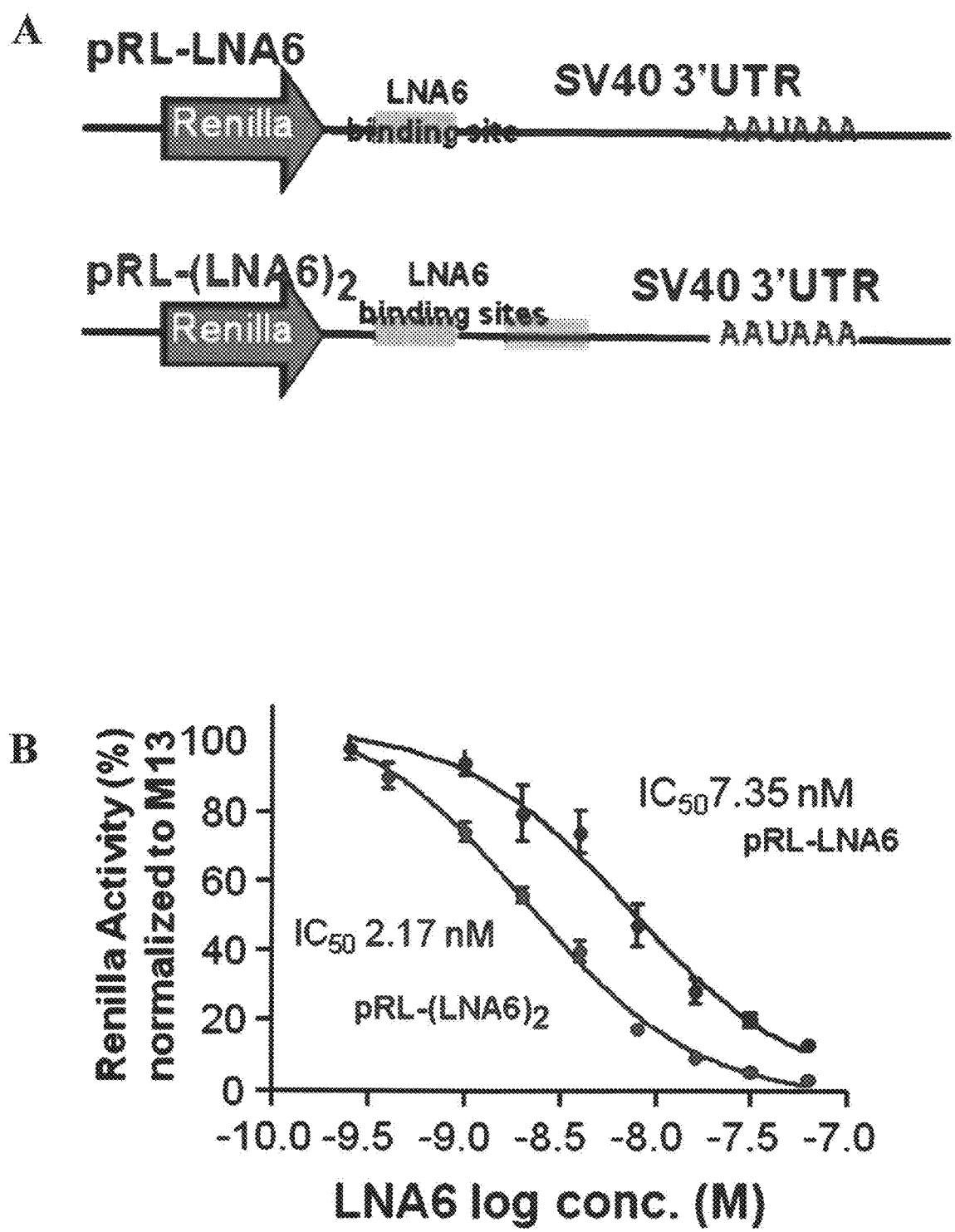

It has previously been demonstrated that two U1 snRNP binding sites gave synergistic enhanced inhibition when inserted into the 3' terminal exon of a reporter gene (Fortes et al. (2003) Proc. Natl. Acad. Sci., 100:8264-8269). It has also been shown that two 5'-end-mutated U1 snRNAs gave synergistic inhibition when targeting a single endogenous gene (Fortes et al. (2003) Proc. Natl. Acad. Sci., 100:8264-8269). To demonstrate whether U1 adaptors would behave in the same way, a second LNA6 binding site was inserted into the pRL-LNA6 plasmid to make the pRL-(LNA6)$_2$ plasmid (FIG. 4A). The analysis described hereinabove was repeated and the results indicate multiple U1 adaptors give enhanced inhibition (FIG. 4B). Notably, such increases in inhibition are rarely seen when targeting one mRNA with two siRNAs (Elbashir et al. (2001) Nature 411:494-8 Novina et al. (2004) Nature 430:161-4).

Example III

The human C-raf-1 gene was selected to test the U1 adaptor on an endogenous gene. It is well known that the accessibility of the target sequence is often a rate-limiting step in antisense- and siRNA-based approaches. This may also be true for U1 adaptors given their annealing domains have to target pre-mRNA. Given that antisense-based approaches also target nuclear pre-mRNA (although for Rnase H-mediated degradation and not poly(A) site inhibition), it was reasoned that a successful antisense oligonucleotide would imply the target pre-mRNA is available for annealing and could be targeted with a U1 adaptor at the same or a nearby sequence. Monia et al. (Nat Med. (1996) 2:668-75) screened ~34 antisense oligonucleotides to determine which would be best at inhibiting expression of the C-raf-1 kinase gene. Of the 34, only 2 good inhibitors were found. Both antisense oligonucleotides were in the terminal exon and are, therefore, candidates for targeting with a U1 adaptor.

C-raf-1 is a member of the raf family of genes that are downstream effectors of ras protein function as part of the MAP kinase signaling pathway (GenBank Accession No. NM_002880). Mutations in raf genes transform cells in vitro and are associated with certain tumors. High expression of C-raf-1 mRNA and protein is also found in certain tumors.

As diagrammed in FIG. 5A, a sequence in the 3'UTR of the endogenous human C-raf-1 gene was targeted with LNA13. Notably, the U1 domain composition is different between LNA6 and LNA13 in that the positions of the LNAs were changed. This was done in part to avoid intramolecular basepairing (e.g., hairpin formation) and intermolecular basepairing (e.g., oligomerization) interactions of the LNA13 adaptor as predicted by computational methods using freely available algorithms such as those from IDT Corporation (Iowa) or Exiqon (Denmark).

HeLa cells are known to express C-raf-1 mRNA and quantitative PCR (Q-PCR) conditions were established to measure mRNA levels of C-raf-1, GAPDH, and Actin. Transfection conditions were as described above with the M13 oligonucleotide being used to bring the final concentration of total oligonucleotide to 62 nM. After 24 hours cells were harvested and used to make total RNA. Q-PCR conditions were: 95° melt, 55° anneal, and 72° extend for 15 seconds. The primers used were: C-raf-1 forward primer=5'-TGTTTCCAGGAT-GCCTGTT-3' (SEQ ID NO: 8), C-raf-1 reverse primer=5'-GGACATTAGGTGTGGATGTCG-3' (SEQ ID NO: 9), GAPDH forward primer=5'-AGCCACATCGCTCAGA-CAC-3' (SEQ ID NO: 10), and GAPDH reverse primer=5'-GCCCAATACGACCAAATCC-3' (SEQ ID NO: 11).

Q-PCR was performed using a ROTOR-GENE™ 3000 machine (Corbett Life Sciences) with SYBR Green I detection. The data were analyzed with the comparative CT method (Pfaffl, M. W. (2001) Nuc. Acid Res., 29:2002-2007) that was adapted to quantitate C-raf-1 mRNA relative to GAPDH mRNA. Results are plotted in FIG. 5B and an $IC_{50}$ of 17.8 nM was observed, a value that compares favorably with that of the best antisense oligonucleotide (out of 34 tested) called "ISIS 5132" in Monia et al. (Nat Med. (1996) 2:668-75) that had an $IC_{50}$=50 nM. Notably, LNA13 cannot act through the Rnase H cleavage pathway because it contains a sufficient number of modified nucleotides so that Rnase H activity is inhibited (Kurreck et al. (2002) Nuc. Acids Res., 30:1911-8). Thus LNA13's $IC_{50}$ value of 17.8 nM does not arise from the Rnase H cleavage pathway.

The C-raf-1 3'UTR and sequences past the poly(A) site were subcloned into a *Renilla* reporter to make the pRL-wtC-raf-1 plasmid. This allowed for the direct comparison of the $IC_{50}$ values with other *Renilla* reporter plasmids as discussed hereinabove. As shown in FIG. 6A, co-transfection of pRL-wtC-raf-1 with LNA13 gave an $IC_{50}$ value of 7.98 nM which is similar to the $IC_{50}$ value seen with the endogenous C-raf-1 gene. Some differences may be expected as the pRL-wtC-raf-1 plasmid produces a chimeric mRNA that may behave differently than the endogenous gene.

To determine the intrinsic inhibitory activity of LNA13, a single LNA13 binding site was inserted into pRL-SV40 and inhibition was tested as described above. An $IC_{50}$ value of ~2 nM was determined. Thus, the inhibitory activity of a single U1 adaptor, in this case LNA13, varies when tested against its endogenous target gene, a reporter plasmid with the natural 3'UTR of the target gene (FIG. 6A), and a reporter plasmid with the isolated binding site (FIG. 6B). Without being bound by theory, the differences in activity may be due to accessibility. Accessibility factors includes (1) folding of the pre-mRNA sequence, (2) binding of trans-acting factors, and (3) the rate of 3' end processing of the pre-mRNA.

Example IV

The U1 domain contributes to U1 adaptor activity by its affinity to U1 snRNA and more broadly to the U1 snRNP complex. Although the U1 domain sequence is fixed (unless variant U1 snRNAs are targeted), the U1 domain sequence can be lengthened and its composition can be changed. To this end, replacing the LNA-DNA mixmer design with 100% 2'-O-methyl resulted in only a small decrease in activity (FIG. 7). Notably, 2'-O-methyl nucleotides are easier to use during synthesis and have a lower cost as compared to LNA-DNA mixmers. Additionally, having a uniform U1 domain composition simplifies adaptor design as the focus is then on optimizing the annealing domain. Having 100% 2'-O-methyl also reduces self annealing problems as compared to having an LNA-DNA mixmer design or other mixmer combinations. The mixmer annealing domain of LNA6 was also replaced with a matching sequence comprising 100% 2'-O-methyl. However, the adaptor comprising only 2'O-methyl showed reduced activity. Extension of the annealing domain (Ome-5 U1 adaptor) failed to restore activity indicating that the presence of only 2'O-methyl in the annealing domain could not simply be compensated for by a longer annealing domain.

The U1 adaptor design has the advantage that inhibition does not require enzymatic activity. Thus, a variety of modified bases may be incorporated into its design. Phosphorothioate (PS) bonds are typically incorporated into antisense molecules to improve their stability when delivered into cells. To test whether PS bonds would affect activity, the activity of two matched adaptors LNA17 and LNA21 that differ only in that LNA21 has PS bonds were compared. As can be seen in FIG. 8, these two matched adaptors had similar activities, thereby indicating that PS bonds did not effect activity.

To test whether the U1 domain can be moved to the other end of the U1 adaptor, a set of matching adaptors where the U1 domain was placed at either the 5' or 3' of the annealing domain was synthesized. The activity of these two adaptors was found to be comparable, thereby indicating U1 snRNP access to the U1 domain does not depend on its position relative to the annealing domain. A U1 adaptor comprising two U1 domains on both sides (i.e., a multivalent adaptor) was also synthesized. However, no significant change in activity was found as compared to the monovalent adaptors. This suggests that U1 snRNP binding is not the limiting factor for inhibitory activity in vivo. Linker bases were also inserted between the annealing and U1 domains. Notably, no loss or improvement in U1 adaptor activity was found.

Example V

Figure 9:
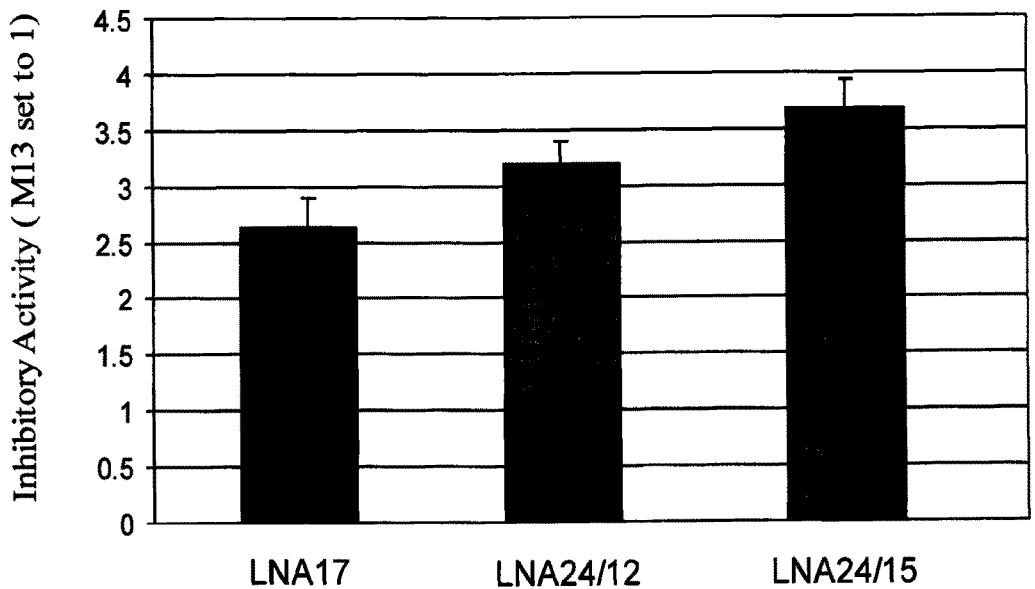

A series of adaptors were synthesized and tested where the U1 domain was held constant and the length and composition of the annealing domain were varied. As seen in FIG. 9, shortening the annealing domain can lead to a reduction in adaptor activity. Furthermore, reducing the basepairing potential by substituting DNA bases for LNAs can also reduce activity.

Figure 10:
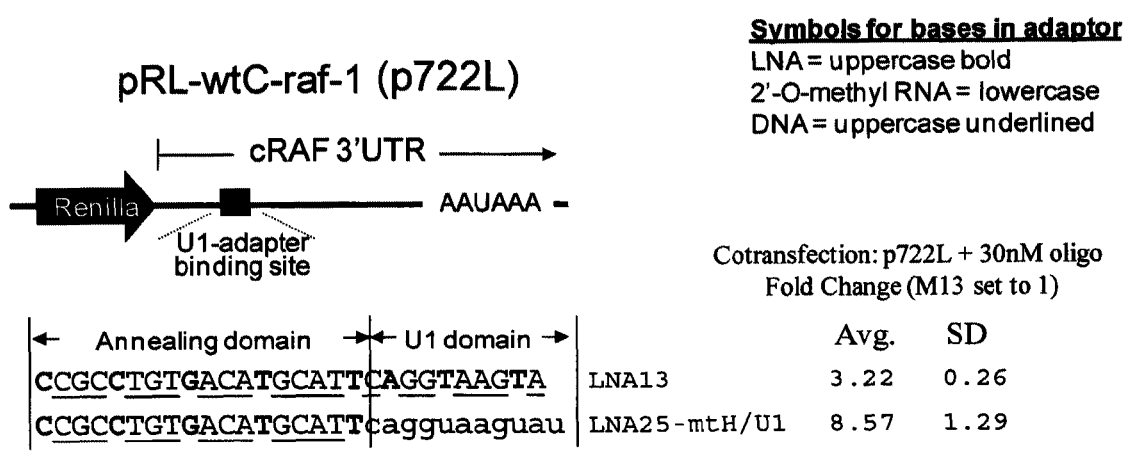
Figure 11:
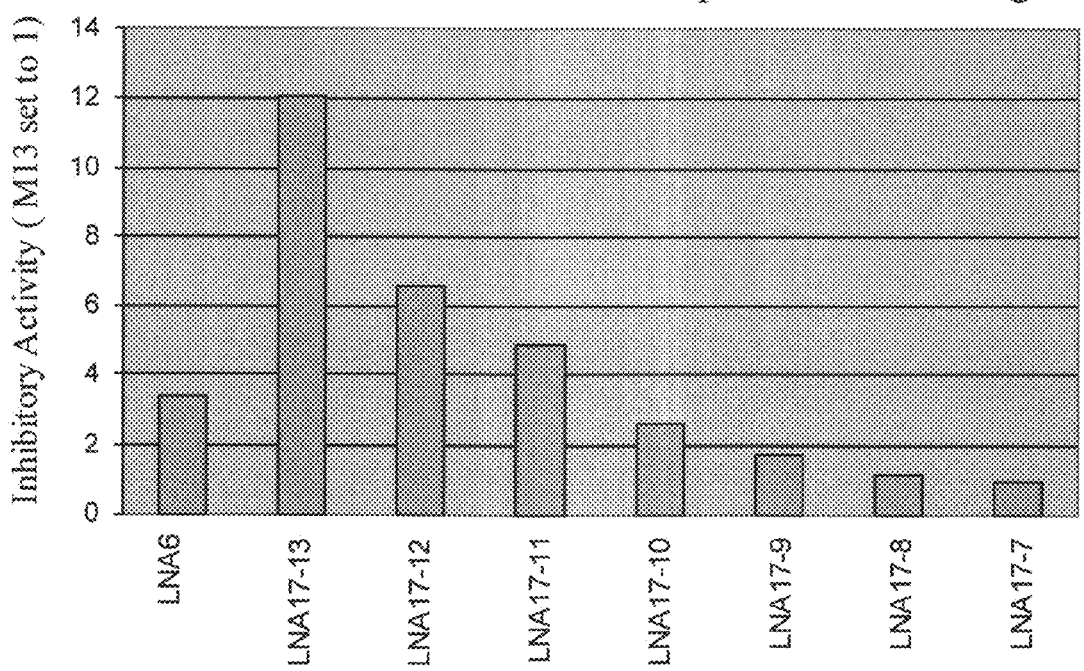

The U1 domain length of the U1 adaptors described hereinabove has been limited to 10 nucleotides, mostly because its natural consensus binding site (i.e., the 5'ss) is 9 to 10 nucleotides long. The 5'-most nucleotide of U1 snRNA is an A and is not thought to play a role in 5'ss binding. However, the effect of this nucleotide on U1 adaptor activity was tested. Matching adaptors that differ only by 1 nucleotide in the U1 domain were compared. As shown in FIG. 10, the 1 nucleotide-extended U1 domain gives a significant increase in inhibitory activity Based on the above results with the additional nucleotide, a matched series of adaptors (the LNA17 series) that incrementally vary the U1 domain length from 7 to 13 nucleotides was tested. U1 adaptor activity was found to steadily increase from no activity (7 nucleotide U1 domain) to high activity (13 nucleotide U1 domain). Given the adaptors in FIGS. 9 and 10 have different annealing domains, it can be concluded that improvement by longer U1 domains does not depend on the annealing domain. Based on the known structure of U1 snRNA, the higher activity may be because the 12th and 13th nucleotides of the U1 domain insert themselves into stem 1A of U1 snRNA. Stem 1A is highly conserved in U1 snRNAs from yeast to humans, suggesting they are functionally important. Further extensions of the U1 domain will eventually disrupt U1 snRNP conformation, such as disrupting binding of U1-70K to stem loop 1. Thus, further extensions of the adaptors will eventually lead to inactive U1 adaptor activity because of disruption of U1 snRNP inhibitory activity.

Example VI

The U1 adaptors were tested in a variety of cell types. It has been previously shown that U1in-based gene silencing is active in a broad variety of vertebrate cell lines and primary cells (Fortes et al. (2003) Proc. Natl. Acad. Sci., 100: 8264-8269). To test U1 adaptors, the LNA17-11 adaptor was transfected into the cell lines shown in FIG. 12. U1 adaptor activity was found in all cases, though there was some variance in the amount of inhibition.

Example VII

As discussed hereinabove, U1 adaptors and siRNA utilize distinct mechanisms that occur in different compartments of the cell (nucleus versus cytoplasm). To determine whether their combined usage to silence a single gene would give enhanced inhibition, the pRL-LNA6 *Renilla* reporter plasmid was targeted with 1 nM anti-*Renilla* siRNA (RL-siRNA) from Ambion/ABI (catalog 4630; Austin, Tex.) and 30 nM LNA6 adaptor. Control siRNA (Ctr-siRNA) from Ambion/ABI (catalog 4611G) and the LNA7 control adaptor were used as controls. As shown in FIG. 13A, the co-transfection of RL-siRNA with LNA6 gave markedly enhanced inhibition of *Renilla* expression when compared to use of the control oligos.

To rule out that these results depend on the type of adaptor and reporter, an anti-GAPDH U1 adaptor (LNA12) was used in place of LNA6 and the reporter plasmid having an annealing site for LNA12 because it contains the 3'UTR of the human GAPDH mRNA (FIG. 13B). More specifically, pRL-GAPDH is a *Renilla* reporter with the 3'UTR and poly(A) signal sequences derived from the human GAPDH mRNA (GenBank Accession No. NM_002046) plus 200 basepairs past the GAPDH poly(A) signal. The LNA12 adaptor is targeting 1231-1245, using Gen Bank Accession No. NM_002046 coordinates.

As shown in FIG. 13C, enhanced activity was observed when 15 nM LNA12 and 1 nM RL-siRNA were used together. Although the siRNAs used in these experiments are more active in silencing than the U1 adaptors, it should be noted that the siRNAs were optimized over the course of years to produce such highly active siRNAs to GAPDH and to *Renilla* reporter plasmids.

In view of the above data, the combination of U1 adaptors with more traditional antisense-based methods that employ RNase H activity were tested. In this experiment, the pRL-wtC-raf reporter plasmid was targeted. The LNA25-H/U1 oligo combines into one molecule both adaptor and Rnase H activities by designing the annealing domain to have an uninterrupted stretch of at least seven DNA bases (in this case 10 bases) as seen for LNA25-H/U1. Such a "7 nt DNA design" was shown by Grünweller et al. (Nuc. Acids Res. (2003) 31:3185-93) to be sufficient for Rnase H activity, although longer stretches are more active. LNA25-mtH/U1 matches LNA25-H/U1 but has the stretch of DNAs interrupted and so should not have Rnase H activity. In like manner, LNA25-H/mtU1 matches LNA25-H/U1 but has a 2 nucleotide mutation in the U1 domain (FIG. 14A). This design is such that LNA25-H/mtU1 has only Rnase H activity, LNA25-mtH/U1 has only U1 adaptor activity, and LNA25-H/U1 will have both activities. As can be seen in FIG. 14B, the LNA25-H/U1 has higher activity indicating both silencing methods can give enhanced activity when used together. Notably, DNA stretches that are longer than 10 nucleotides can be used, however the potential for self annealing of oligos with longer DNA stretches needs to be considered.

Example VIII

To determine whether the LNA25 series of oligonucleotides can inhibit expression of the endogenous C-raf-1 gene, HeLa cells were transfected with LNA25-mtH/U1 and Western blotting combined with Q-PCR was performed. The results in FIG. 15 show specific silencing of C-raf-1 both at the protein and mRNA levels. It has been reported that silencing of C-raf-1 leads to induction of cleavage of the PARP protein as part of induction of apoptosis (Lau et al. (1998) Oncogene 16:1899-902). Re-probing the Western blot in FIG. 15A with anti-PARP antibody demonstrated that the U1 adaptors induce PARP cleavage indicative of C-raf-1 silencing.

As described hereinabove, the combinatorial use of adaptors and Rnase H gave enhanced silencing of a reporter plasmid. To determine whether enhanced activity could be extended to silencing of the endogenous C-raf-1 gene, the above transfections in Example VII were repeated, but now the levels of the endogenous C-raf-1 protein and mRNA were measured. The results in FIG. 16 show enhanced silencing of C-raf-1 both at the protein and mRNA levels.

Example IX

Introduction

Use of RNAi to silence specific vertebrate genes has rapidly become a standard method for gene function analysis and has garnered much attention as a promising new molecular therapy (Hannon et al. (2004) Nature 431:371-8; Kim et al. (2007) Nat. Rev. Genet., 8:173-84). RNAi silences gene expression by degrading the target mRNA in the cytoplasm and typically employs synthetic siRNA duplexes (Elbashir et al. (2001) Nature 411:494-8) or engineered vectors (plasmid or viral) that express longer precursor RNAs (e.g., short hairpin shRNAs). An alternative gene silencing method called U1i (U1 small nuclear RNA-U1 snRNA-interference) that uses a plasmid vector to express an engineered U1 snRNA (called a U1i snRNA) in which a 10 nucleotide (nt) sequence complementary to the target gene's terminal exon replaces the natural U1 targeting domain was previously published (Beckley et al. (2001) Mol. Cell Biol., 21:2815-25; Fortes et al. (2003) Proc. Natl. Acad. Sci. USA 100: 8264-8269). The U1i snRNA assembles into a U1 snRNP complex that basepairs to the target gene's pre-mRNA and inhibits polyA tail addition, an obligatory RNA processing step for nearly all eukaryotic mRNA (Fortes et al. (2003) Proc. Natl. Acad. Sci. USA 100: 8264-8269; Liu et al. (2004) Nucleic Acids Res., 32:1512-7). Without polyadenylation, the pre-mRNA fails to mature and is degraded in the nucleus, thereby reducing levels of cytoplasmic mRNA of the target gene. The mammalian U1 snRNP consists of 10 proteins bound to the 164 nt U1 snRNA and functions early in splicing via a base pairing interaction between U1 snRNA and the 5' splice site sequence (Will et al. (1997) Curr. Opin. Cell Biol., 9:320-8). Separate from its role in splicing, U1 snRNP can also be a potent inhibitor of gene expression when it is bound near the polyA signal of the pre-mRNA. This was first shown in papillomaviruses (Furth et al. (1994) Mol. Cell. Biol., 14:5278-5289) and more recently in certain mammalian genes (Guan et al. (2007) RNA J., 13:2129-2140) and it is this property of U1 snRNP that forms the basis of the U1i silencing method. The inhibitory mechanism involves the U1-70K subunit of U1 snRNP binding to and inhibiting the activity of polyA polymerase (Gunderson et al. (1998) Mol. Cell, 1:255-264).

Although U1i is effective in reducing mRNA levels, it has not been widely adopted as a gene silencing technology due to the inconvenience of preparing custom U1i targeting plasmids and concerns over specificity. U1i binds the target mRNA using a 10 nt domain engineered onto the 5'-end of the U1 snRNA. Lengthening this 10 nt domain paradoxically results in weaker silencing. Furthermore, the U1i snRNA must be expressed off a plasmid or viral vector and attempts to shorten its length while maintaining activity, so as to be amenable to chemical synthesis, have not been successful.

These problems are circumvented herein by employing a synthetic oligonucleotide, a U1 Adaptor, to recruit endogenous U1 snRNP to the target site. The U1 Adaptor has two domains: a "Target Domain" designed to base pair to the target gene's pre-mRNA in the 3' terminal exon, and a "U1 Domain" that tethers U1 snRNP to the target. Bringing the U1 snRNP in contact with the target pre-mRNA inhibits proper 3'-end formation and eventually leads to RNA degradation. Using optimized U1 Adaptor design and chemical modifications to improve binding affinity, very high potency is seen and subnanomolar $IC_{50}$ (the concentration needed to inhibit gene expression by 50%) can be achieved. Interestingly, targeting the same gene either with multiple U1 Adaptors or by co-transfection of U1 Adaptors with siRNAs gives synergistic higher levels of inhibition, the latter probably because U1 Adaptors and siRNAs utilize distinct mechanisms and act in distinct cellular compartments. U1 Adaptors add a new dimension to the gene silencing tool kit and can be used either as a stand-alone method or in combination with RNAi.

Materials and Methods

Method for Transfection and Luciferase Assays

Cell culture and transfections were done as previously described (Goraczniak et al. (2008) J. Biol. Chem., 283:2286-96). For luciferase assays, the cells were harvested after 24-48 hours and luciferase measured using the Promega dual luciferase kit (Promega, Madison, Wis.) measured on a Turner BioSystems Luminometer (Turner BioSystems, Sunnyvale, Calif.). For inhibition of endogenous genes, cells were harvested after 24-48 hours and either lysed in SDS buffer for Western blotting or total RNA was extracted using the RNeasy kit (Qiagen, Valencia, Calif.). Nuclear and cytoplasmic RNA preparations were performed as described (Goraczniak et al. (2008) J. Biol. Chem., 283:2286-96). The anti-Renilla siRNA and was purchased from ABI/Ambion (Austin, Tex.). All of the U1 Adaptors and the anti-PCSK9 siRNA and anti-RAF1 siRNA were manufactured by Integrated DNA Technologies (IDT, Coralville, Iowa). A list of sequences for all the U1 Adaptors and siRNAs is provided in FIGS. 34 and 35.

ECL Western Blots

ECL Western blotting was done as previously described (Gunderson et al. (1998) Mol. Cell 1:255-264) using a 1:10000 dilution of an anti-GAPDH antibody (Chemicon division of Millipore, Billerica, Mass.), a 1:1000 dilution of an anti-RAF1 antibody (R1912 from BD Biosciences, San Jose, Calif.), or a 1:1000 dilution of an anti-PARP antibody (Ab-2 from Oncogene, Cambridge, Mass.). The secondary anti-mouse and anti-rabbit antibodies were used at a 1:5000 dilution (Amersham Biosciences, Piscataway, N.J.). The membrane used was Immobilon-P (Millipore) and was treated as per manufacturer's instructions.

General Method for Quantitative Real-Time PCR (qPCR)

RNA from transfected cells was isolated using the RNeasy kit (Qiagen). Complementary DNA (cDNA) was synthesized using 1 µg of RNA, random hexamers and MMLV reverse transcriptase as suggested by the manufacturer (Promega). 50 ng of cDNA was analyzed using qPCR run on a Rotorgene 3000 (Corbett Research, Sydney, Australia) and the QuantiTech SYBR Green PCR kit (Qiagen). Results from test genes were normalized using GAPDH as an internal control. Primer sequences are provided herein. The comparative cycle threshold (Ct) method was used (Pfaffl, M. W. (2001) Nucleic Acid Res., 29:2002-2007) to analyze the data where the relative values of the amount of target cDNA equal $2-\Delta\Delta Ct$, where $\Delta Ct$=difference between the threshold cycles of the target (RAF1) and an endogenous reference (GAPDH), and $-\Delta\Delta Ct$=difference between $\Delta Ct$ of the target sample and a control (cells treated with M13 oligo).

Preparation and Analysis of RNA

RPA and the uniformly $^{32}P$-labelled RNA probes were made by in vitro transcription with T7 or SP6 RNA polymerase in the presence of 32P-UTP as described (Goraczniak et al. (2008) J. Biol. Chem., 283:2286-96). The qPCR conditions were: 95° C. melting temperature, 55° C. annealing temperature and 72° C. extension temperature each for 15 seconds. The sequences of the oligonucleotides used to measure GAPDH and cRAF by qPCR are given below (from top to bottom: SEQ ID NOs: 8-11, 66, 67).

```
C-raf-1 forward primer = 5'-TGTTTCCAGGATGCCTGTT

C-raf-1 reverse primer = 5'-GGACATTAGGTGTGGATGTCG

GAPDH forward primer = 5'-AGCCACATCGCTCAGACAC

GAPDH reverse primer = 5'-GCCCAATACGACCAAATCC

PCSK9 forward primer = 5'-ATGTCGACTACATCGAGGAGGACT

PCSK9 reverse primer = 5'-TGGTCACTCTGTATGCTGGTGTCT
```

The sequences of the oligonucleotides used for RT-PCR are given below (from top to bottom: SEQ ID NOs: 68-75).

```
Cdc25B forward primer = 5'-CCATCAGACGCTTCCAGTCT

Cdc25B reverse primer = 5'-GTCTCTGGGCAAAGGCTTC

Cdc25C forward primer = 5'-TGGCTCAGGACCCAGTTTTA

Cdc25C reverse primer = 5'-TCTTCTGCCTGGTCTTCTCC

Grb2 forward primer =
5'-CGCGAAGCTTGTTTTGAACGAAGAATGTGATCAG

Grb2 reverse primer =
5'-GAGAGGTACCCTGTGGCACCTGTTCTATGTCCCGCAGGAATATC

Fibronectin forward primer =
5'-TGCGGTACCGGCCTGGAGTACAATGTCA

Fibronectin reverse primer =
5'-TGCGGTACCGAGGTGACACGCATGGTGTC
```

Western Blotting

The anti-PARP antibody employed was Ab-2 from Oncogene (La Jolla, Calif.). The secondary anti-mouse and anti-rabbit antibodies were used at a 1:5000 dilution (Amersham, Piscataway, N.J.) as was the chemiluminescent reagent. The membrane used was Immobilon-P (Millipore, Bedford, Mass.) and was treated as per the manufacturer's instructions.
EMSA U1 snRNP was purified as previously described (Abad et al. (2008) Nucleic Acids Res., 36:2338-52; Gunderson et al. (1998) Molecular Cell, 1: 255-264). For FIG. 18, gel purified, $^{32}$P-radiolabeled RNA probe was incubated with purified U1 snRNP and U1 Adaptor as indicated in binding buffer (BB) (BB=20 mM HEPES-KOH (pH 7.9), 100 mM KCl, 1.5 mM MgCl2, 5 mM dithiothreitol, 5% glycerol, 15 μg tRNA) in a total volume of 15 μl at room temperature for 15 min. The protein-RNA complexes were then loaded on a 6% polyacrylamide gel with 1×TBE and 5% glycerol and electrophoresed for 2.5 hours at 20V/cm. Gels were dried and used first for autoradiography followed by phosphoimagery analysis to quantitate the complexes as described (Abad et al. (2008) Nucleic Acids Res., 36:2338-52). For FIG. 20, the U1 snRNP was first bound to unlabeled U1 Adaptor and, after 15 minutes, the radiolabeled RNA probe was added and 10 minutes later PAGE was performed as in FIG. 18.

Microarray Analysis

Microarray analysis and data interpretation were performed at the Cancer Institute of New Jersey (CINJ) Microarray facility that offers complete Affymetrix GeneChip technology including data analysis. For each gene, dividing the anti-PCSK9 DsiRNA by the M13 control is a measure of the -fold change of that gene due to the anti-PCSK9 DsiRNA. Likewise dividing the anti-PCSK9 UA31d4+UA31e Adaptors by the M13 control is a measure of the -fold change of that gene due to the anti-PCSK9 Adaptors. The data were filtered by excluding out both "Absent" genes (due to very-low-expression) as well as genes where the p values were >0.05 or that had "zeros" in the change call (i.e. those genes that did not significantly change). Out of 54,000 human transcripts represented on the chip, about 4000 had changes ≧2-fold (that is R2/R1 and R3:R1 were ≧2-fold). These 4000 were ranked according to genes with the largest decrease and it was found that PCSK9 ranked seventh highest for the anti-PCSK9 Adaptors and first for the anti-PCSK9 DsiRNA consistent with it being the target for silencing.

Results

U1 Adaptor Oligonucleotides Reduce Gene Expression

Figure 17:
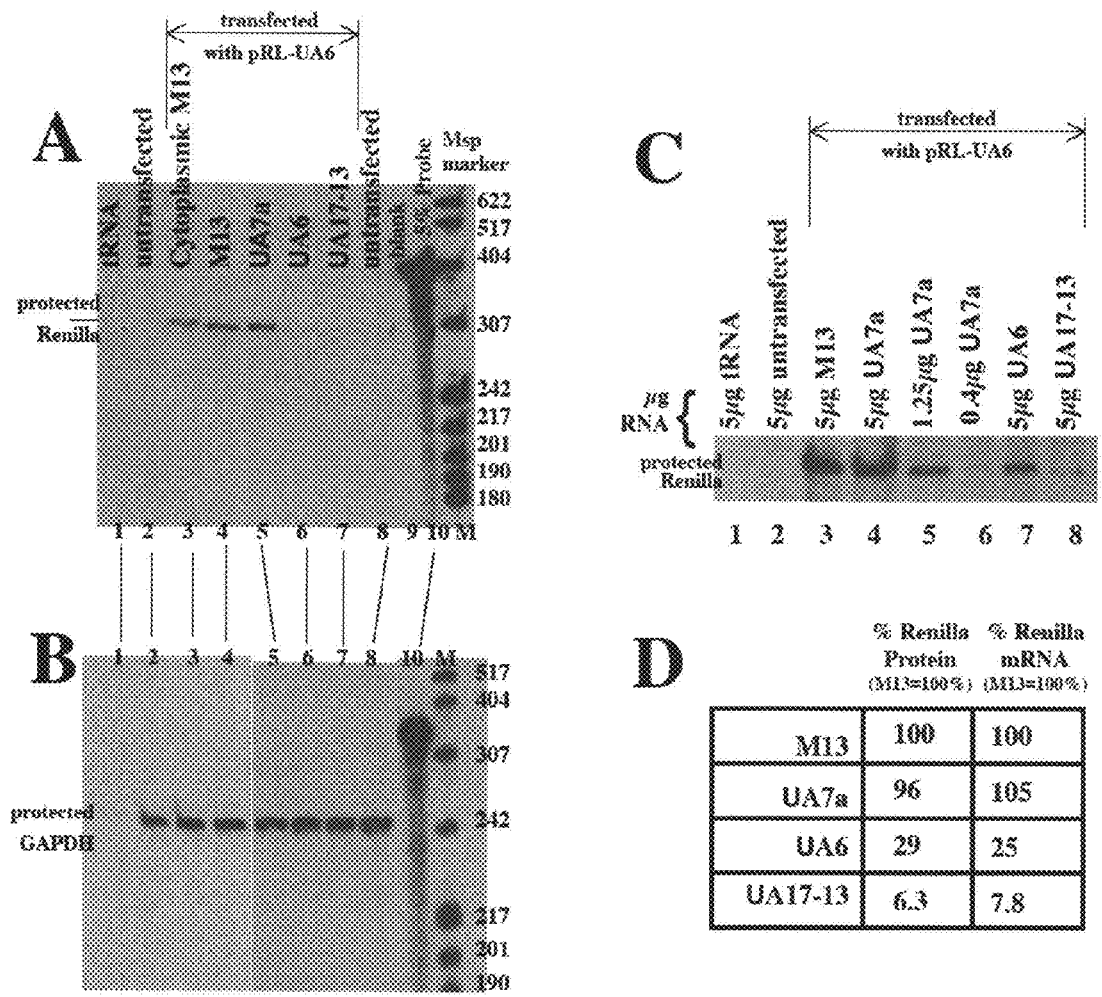
Figure 18:
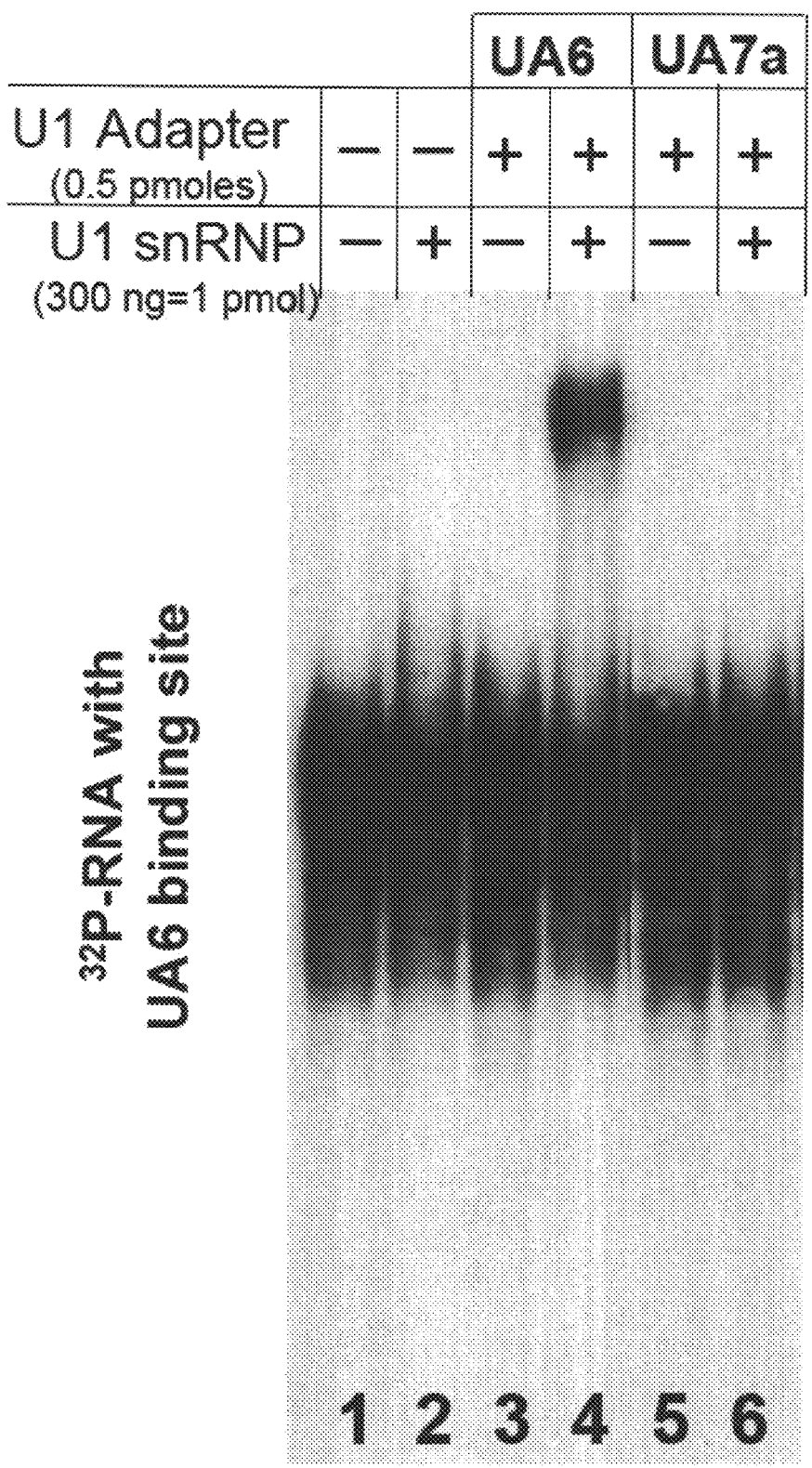

To facilitate rapid analysis, the dual luciferase reporter system was used where *Renilla luciferase* mRNA was targeted for inhibition by U1 Adaptors and a co-transfected Firefly luciferase reporter served as an internal normalization control. The first target studied was MARK1 (NM_018650), which contains a single natural U1 snRNP binding site (U1 site) in its 3'-UTR that downregulates MARK1 expression in the wildtype (wt) gene (Guan et al. (2007) RNA J., 13:2129-2140). The reporter pRL-MARK1 wt was made from a standard pRL-SV40 Renilla expression plasmid by replacing the SV40-derived 3'UTR and polyA signal sequences with the human MARK1 3'UTR and polyA signal region, including 146 nt past the polyA site. The pRLMARK1mt reporter matches pRL-MARK1 wt except for a four base change in the natural U1 site. Each MARK1 reporter was transfected into HeLa cells along with a control Firefly reporter. It was observed that the pRL-MARK1mt plasmid has a 17-fold increase in *Renilla* luciferase expression as compared to the pRL-MARK1 wt plasmid indicating that the natural U1 site causes a 17-fold level of inhibition in the wt reporter (see hereinabove). The fact that the wt MARK1 3'UTR can be inhibited by a U1 snRNP-mediated mechanism indicated that this sequence context would be a good first test for the U1 Adaptor method. A 25 nt U1 Adaptor oligonucleotide called UA6 for U1 Adaptor 6, was designed with a 10 nt U1 Domain complementary to the 5'-end of the U1 snRNA and a 15 nt Target Domain complementary to MARK1 sequence immediately 3' to the mutated U1 binding site in pRL-MARK1mt. UA6 has ten locked nucleic acid (LNA) nucleotides with the other positions being DNA nucleotides. Co-transfection of the UA6 Adaptor with the pRL-MARK1mt plasmid and the control Firefly reporter into HeLa cells resulted in a 90% inhibition of *Renilla luciferase* expression at 62 nM concentration with an $IC_{50}$ of 6.6 nM (see hereinabove). A Ribonuclease Protection Analysis (RPA) with a Renilla mRNA-specific probe (Goraczniak et al. (2008) J. Biol. Chem., 283: 2286-96) demonstrated reduction in both total and cytoplasmic Renilla mRNA levels, indicating that inhibition occurs at the RNA level with no apparent nuclear accumulation of the Renilla mRNA (FIG. 17). To demonstrate UA6 inhibition requires complementarity with U1 snRNA, a mismatch control Adaptor, UA7a, that has a 4 nucleotide mutation in the U1 Domain, was synthesized and tested. A 4 out of 10 base mismatch in this domain reduces complementarity with U1 snRNA so that it no longer binds U1 snRNP. Pre-mRNAs containing this same 4 nt mutation are unable to bind U1 snRNP as compared to a matching pre-mRNA with a wild type U1 Domain sequence using an electrophoretic mobility shift assay (EMSA) and purified U1 snRNP (Gunderson et al. (1998) Mol. Cell 1:255-264; Abad et al. (2008) Nucleic Acids Res.; 36:2338-52). A similar EMSA was used to directly demonstrate that the UA6 Adaptor can tether the U1 snRNP complex to the target RNA (FIG. 18). Co-transfection of the mutant UA7a Adaptor with pRL-MARK1mt plasmid resulted in no inhibition (see hereinabove), demonstrating the importance of the U1 Domain.

The chemical composition and design of the U1 Adaptors is crucial for function. All "first generation" U1 Adaptors were LNA/DNA mixmers. LNA nucleotides contain a carbon linkage between the 2'-oxygen and the 4' carbon of the ribose sugar ring thereby "locking" the nucleotide in an "endo-sugar pucker" position leading to higher duplex stability and relative resistance to nuclease degradation (Kauppinen et al. (2005) Drug Discovery Today Technol., 2:287-290). LNA nucleotides were included in the U1 Adaptor to increase binding affinity of the short functional domains present in the 25 nt oligonucleotide. Placement of LNA nucleotides in this pattern also avoids activation of an RNase H-dependent "antisense" silencing mechanism. 2'-modification of the ribose, such as 2'-O-methyl (2'OMe), LNA, or 2'-Fluoro, blocks RNase H activity. RNase H activation requires at least 4 contiguous DNA residues and does not reach full potency until 7-8 DNAs are present (Kurreck et al. (2002) Nucleic Acids Res., 30:1911-8; Grünweller et al. (2003) Nucleic Acids Res., 31:3185-93). The fact that all of the active U1 Adaptors in this report have ≦4 continuous DNA nucleotides argues against a role for RNase H in U1 Adaptor activity. U1 Adaptor configurations that support both RNase H activity and U1 snRNP binding in the same molecule may increase potency by exploiting two different mechanisms of action.

It is possible that MARK1 sequences flanking the UA6 binding site contribute to the observed suppression. To rule out this possibility, the 15 nt UA6 binding site was tested outside of the context of the MARK1 3'UTR by construction of a reporter called pRL-UA6 that has one UA6 binding site inserted into the 3'UTR and polyA signal sequence derived from SV40 (see hereinabove). Co-transfection of pRL-UA6 with increasing amounts of the UA6 Adaptor suppressed expression of *Renilla luciferase* with an $IC_{50}$ value of 7.4 nM, which is nearly identical to the $IC_{50}$ of 6.6 nM seen for the UA6 Adaptor against the pRL-MARK1mt reporter. As shown hereinabove, the mutated UA7a Adaptor did not show any inhibitory activity. Thus the 15 nt UA6 binding site is necessary and sufficient to quantitatively direct inhibition by the UA6 Adaptor oligonucleotide. It has been previously demonstrated that multiple U1 snRNP binding sites in the terminal exon show additive levels of inhibition (Beckley et al. (2001) Mol. Cell Biol., 21:2815-25; Fortes et al. (2003) Proc. Natl. Acad. Sci. USA, 100:8264-8269; Liu et al. (2004) Nucleic Acids Res., 32:1512-7). A new version of the pRL-UA6 reporter was made that had two tandem UA6 binding sites, called pRL-(UA6)$_2$. As shown hereinabove, the pRL-(UA6)$_2$ reporter with the UA6 Adaptor showed improved knockdown (IC$_{50}$ of 2.2 nM) compared with the pRL-UA6 reporter (IC$_{50}$ of 7.4 nM), demonstrating the U1 Adaptor method shows additive suppression if multiple binding sites exist on the same target. In contrast, multiple siRNAs against the same mRNA do not result in additive inhibition and instead show suppression at the level expected for the single most-potent siRNA in the pool (Hannon et al. (2004) Nature 431:371-8; Elbashir et al. (2001) Nature 411:494-8; Novina et al. (2004) Nature 430:161-4).

Optimization of U1 Adaptor Design

Figure 19:
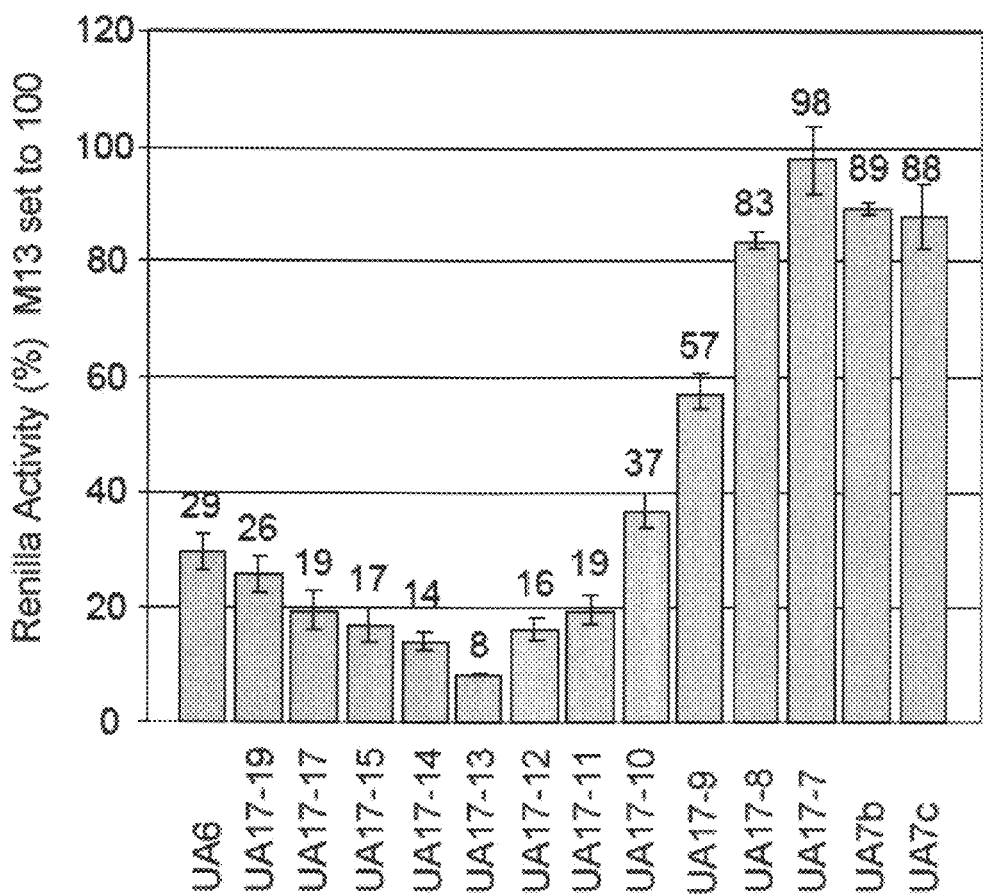
Figure 20:
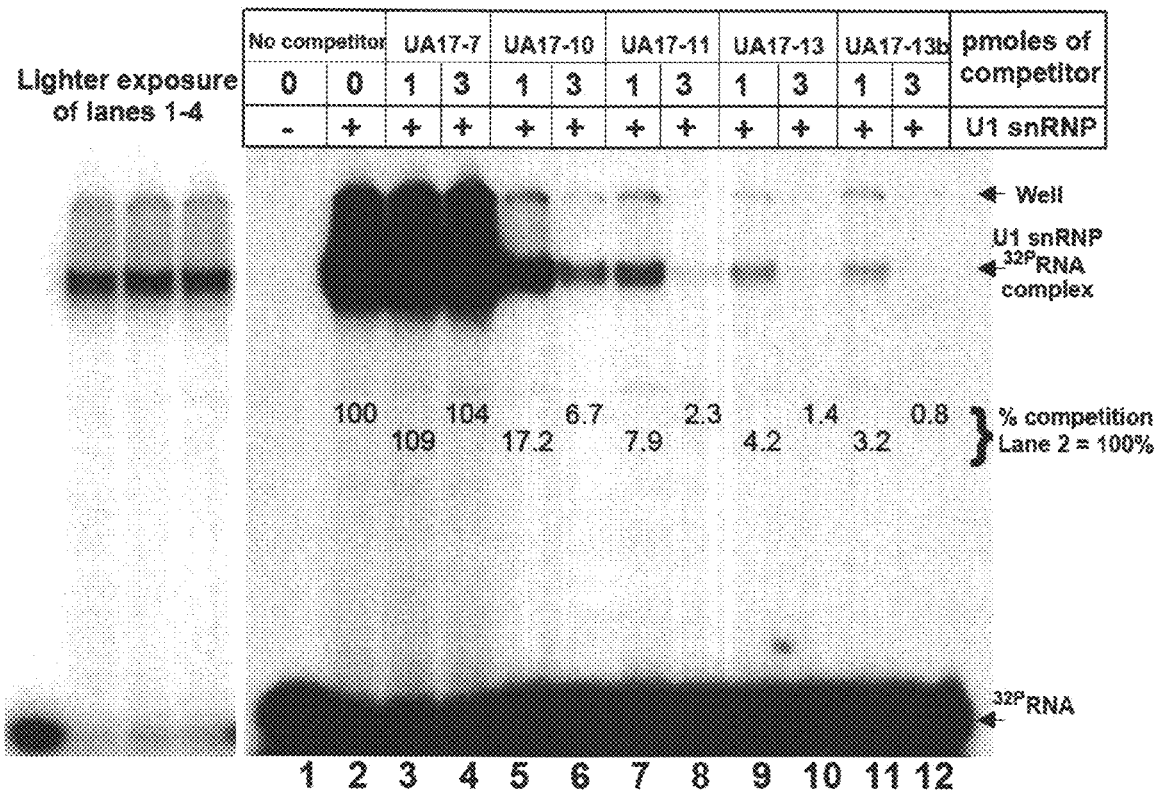

The UA6 Adaptor is a 25 nt LNA-DNA mixmer having 10 nt complementary to the U1 snRNA and 15 nt complementary to the target. The hybridization domains in this U1 Adaptor are short yet function well due to the high LNA content of this oligonucleotide (15/25 bases are LNA). However, having a high LNA content increases the self-dimer and hairpin potential of a sequence (which is further increased by the high stability of LNA:LNA base pair events), complicating the design of U1 Adaptors when applied to other sites. Ways to decrease the relative LNA content were examined by comparing function of different chemistries and the lengths of each domain using the UA6 Adaptor as a model system. First, an all 2'OMe RNA version of the UA6 Adaptor was tested which showed reduced activity (see hereinabove). However, the 10 nt U1 Domain could be substituted with 2'OMe RNA with only a slight loss of activity (UA17-10, see hereinabove and FIG. 19). Continuing to use the 2'OMe RNA chemistry, a series of U1 Adaptors were synthesized varying the length of the U1 Domain from 7 to 19 nt (see hereinabove and FIG. 19). As length of the U1 Domain decreased below 10 nt, activity was gradually lost. As length of the U1 Domain increased, activity increased and peaked at a length of 13 nts. As length further increased, activity decreased. The UA17-13 Adaptor having a 13 nt 2'OMe U1 Domain was 3-fold more potent than the original UA6 Adaptor having a 10 nt DNA/LNA mixmer composition. Although it is not clear why U1 Domains longer than 13 nts show less activity, it may be hypothesized that these longer sequences disrupt the folding structure of the U1 snRNA and may lead to decreased association with the U1-70K protein, the U1 snRNP subunit that inhibits polyA site activity (Gunderson et al. (1998) Mol. Cell 1:255-264). Similar results were observed with a U1 Adaptor specific for a different, target sequence, demonstrating that a peak in activity for 13 nt U1 Domains is not peculiar to UA6. In designing the UA17 series, it was assumed that the inhibitory activities of the UA17 Adaptors could be increased by increasing their relative affinities to U1 snRNP. This was shown to be the case by employing an EMSA competition assay (FIG. 20).

Figure 21:
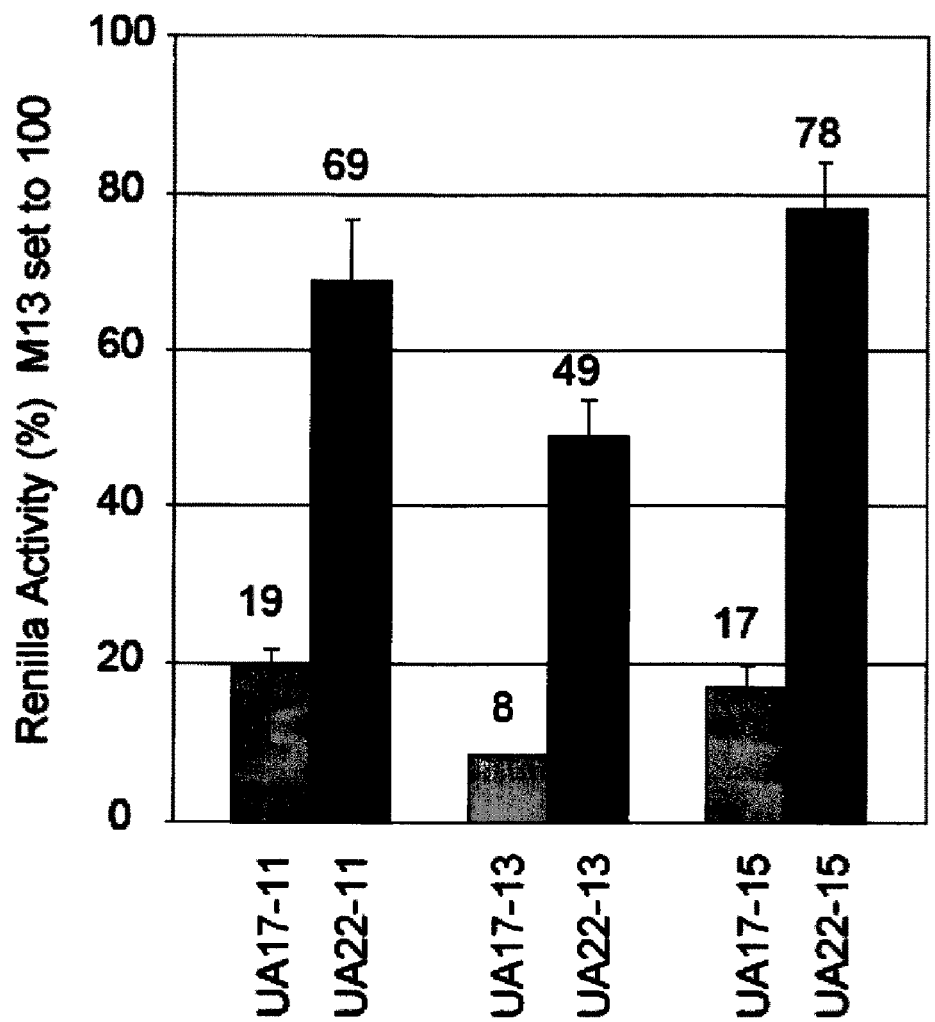
Figure 22:
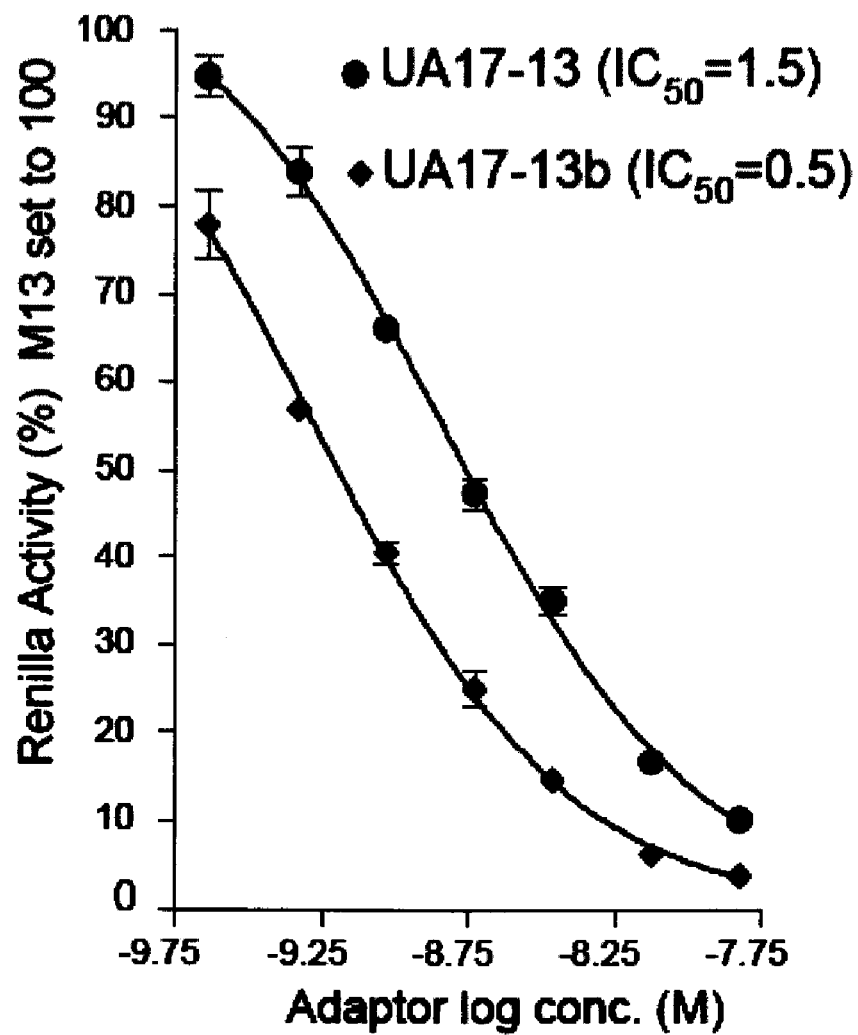

All of the U1 Adaptor sequences studied thus far had the Target Domain at the 5'-end and the U1 Domain at the 3'-end. Switching domain order was tested and it was found that U1 Adaptors having the U1 Domain at the 5'-end were less effective than the original design (FIG. 21). Increasing the length of the U1 Domain to 13 nts did not improve potency of the U1 Adaptor as much when using this configuration. A 2'OMe/LNA mixmer should have higher binding affinity than a uniform 2'OMe RNA or DNA/LNA mixmer sequence when hybridizing to an RNA target. Therefore, use of a mixed 2'OMe RNA and LNA sequence for the U1 Domain was tested, using the optimal 13 nt length. A variant of UA17-13 (the most potent Adaptor identified in FIG. 21 with an IC$_{50}$ of 1.5 nM) having five LNA nucleotides improved potency 3-fold and had an IC$_{50}$ of only 0.5 nM (UA17-13b, FIG. 22). These design improvements have therefore increased potency of the original UA6 Adaptor by over 10-fold.

Figure 24:
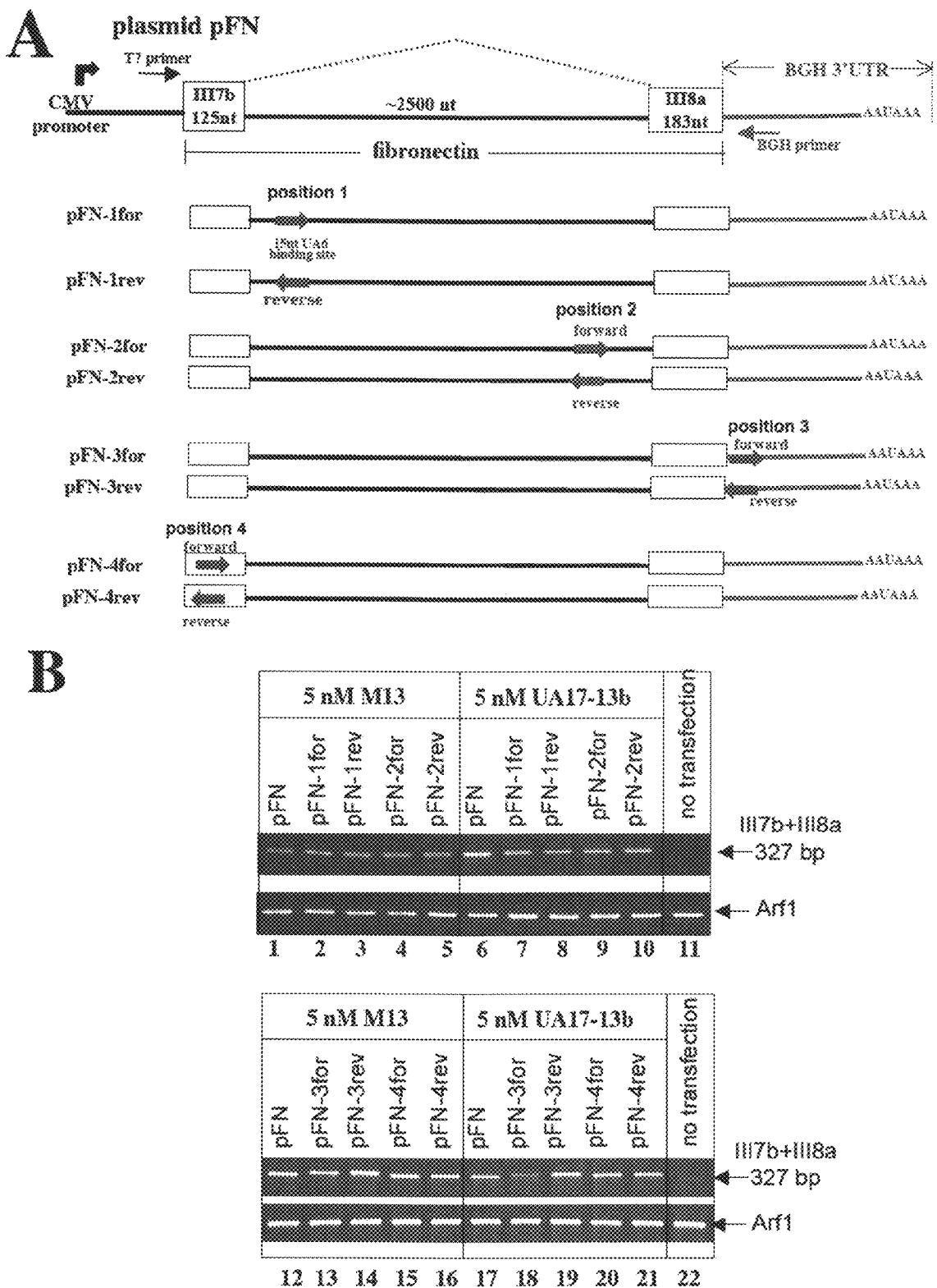

Insights into design optimization of the U1 Domain described above should apply to all U1 Adaptor oligonucleotides. Additional optimization was done examining similar design variation in the Target Domain. However, it is important to note that the optimal length, number and position/configuration of modified nucleotides may vary for different target sequences and so each new target gene and its target sequence may require optimization of the U1 Adaptor's Target Domain. Versions of the UA6 Adaptor sequence having a 100%-2'OMe RNA Target Domain had reduced activity (see hereinabove), whereas a 100%-LNA Target Domain slightly increased activity (see hereinabove). Sequences which are fully LNA modified cannot activate RNase H, so these results rule out the possibility that an RNase H antisense mechanism of action might contribute to the observed gene suppression. Assuming that higher binding affinity is helpful, the length of the 100%-2'OMe RNA Target Domain was increased incrementally from 15 nts to 25 and 35 nts and a loss of activity was observed. Although longer Target Domains might work at other sites, there does appear to be benefit from employing a short, high affinity sequence, which is most easily achieved using the LNA modification. This may relate in part to target secondary structure, and similar findings have been reported for RNase H active antisense oligonucleotides (ASOs); short, high affinity compounds are generally more potent than long, low affinity compounds) (De Paula et al. (2007) RNA 13:431-56; Lennox et al. (2006) Oligonucleotides 16:26-42). Importantly, U1 Adaptors with a phosphorothioate (PS) backbone showed high potency (see hereinabove), a valuable feature as nuclease resistance will likely be more important for function when U1 Adaptors are tested in vivo. The ability of U1 Adaptors to inhibit target RNAs with less-than-perfect complementarity was assessed by testing variants of UA17-13b having 1, 2 and 3 nt changes in the Target Domain against a wt reporter and a mutated reporter having a compensatory 3 nt base change in the target RNA. The results, shown in FIG. 23, demonstrate a graded response with a 3 nt mismatch having no activity and a 1 nt mismatch having around half the activity of the wt U1 Adaptor. Thus, in terms of base mismatch discrimination, U1 Adaptors behave similarly to high affinity ASOs. Although ASOs can show single base discrimination when using low affinity (low Tm) modifications, like methylphosphonates, this level of specificity is usually not achieved when using high affinity (high Tm) modifications like LNAs (Lennox et al. (2006) Oligonucleotides, 16:26-42; Giles et al. (1995) Nucleic Acids Res. 23:954-61). Adaptors are unlike ASOs however, in that they should only suppress expression when tethering U1 snRNP to the 3' terminal exon. Terminal exon restriction is a well-established property of U1 snRNP-mediated inhibition of polyA sites (Beckley et al. (2001) Mol. Cell Biol. 21:2815-25; Fortes et al. (2003) Proc. Natl. Acad. Sci. USA, 100:8264-8269; Liu et al. (2004) Nucleic Acids Res., 32:1512-7.). As shown in FIG. 24, it was confirmed that U1 Adaptors have this same terminal exon restriction by inserting U1 Adaptor binding sites in a variety of positions within a 3-exon/2-intron splicing reporter. Thus, any unintended cross-hybridization of U1 Adaptors to upstream exons and introns is likely to have no effect on expression of that gene.

Inhibiting the Endogenous RAF1 Gene with U1 Adaptors

To assess the ability of U1 Adaptors to suppress expression of endogenous genes, the UA25 Adaptor was designed to the human C-raf-1 (RAF1) gene (NM_002880). RAF1 was selected because it is an oncogene with potential therapeutic utility (Sridhar et al. (2005) Mol. Cancer Ther., 4:677-85). siRNAs are part of the RNA induced silencing complex (RISC) that includes RNA helicases thought to assist in silencing by unwinding target sequences that are hidden within secondary structures. In contrast, U1 snRNP intrinsically lacks RNA helicase activity and presumably the Adaptor:U1 snRNP complex is unlikely to be capable of recruiting helicases, therefore target site accessibility will be important for optimal performance. Since ASOs have the same requirement for target site accessibility, it seems likely that good antisense sites might also be good U1 Adaptor sites. The first RAF1 target site studied was therefore designed at a known potent antisense site in the terminal RAF1 exon previously identified (Monia et al. (1996) Nat. Med., 2:668-75). The UA25 Adaptor employs an 11 nt U1 Domain without LNA nucleotides (see hereinabove and FIG. 25) because longer U1 Domains (12 and 13 nts) with LNA residues resulted in a predicted high potential for self dimer and hairpin structures at this precise site.

Figure 25:
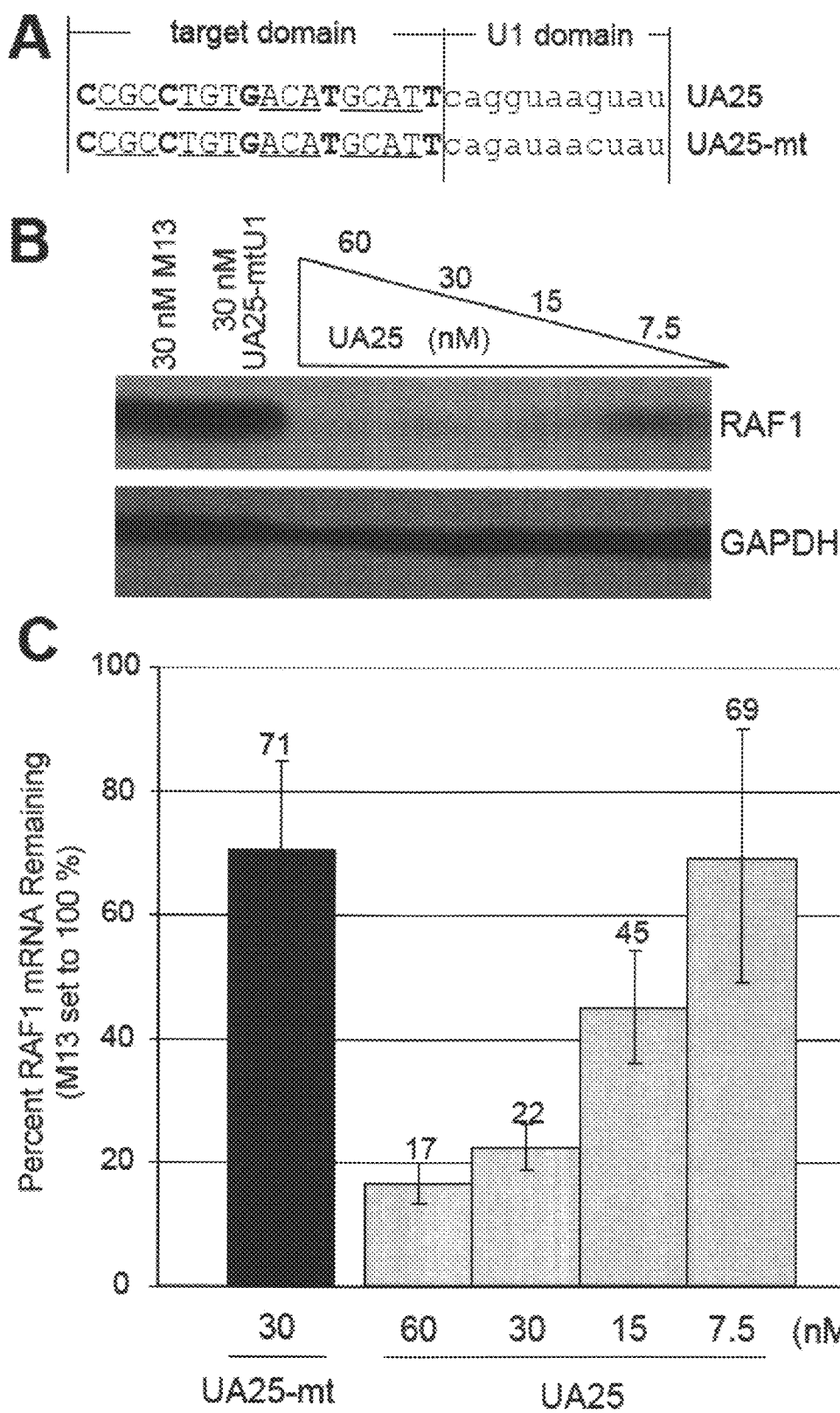

HeLa cells were transfected with the UA25 Adaptor and cell extracts were analyzed by Western blotting for RAF1 expression (FIG. 25). RAF1 protein levels were specifically reduced by UA25 Adaptor in a dose-dependent manner. The control Adaptor UA25-mt, which has a 2 nucleotide mutation in the U1 Domain, was inactive. It has been reported that silencing of RAF1 leads to cleavage of PolyA Ribopolymerase (PARP) as part of induction of apoptosis (Lau et al. (1998) Oncogene 16:1899-902). Re-probing the Western blot in FIG. 25 with an anti-PARP antibody demonstrated that suppressing RAF1 using the UA25 Adaptor induces PARP cleavage (see hereinabove). Quantitative real-time PCR (qPCR) demonstrated that the observed reduction in RAF1 protein levels correlated with similar reductions at the mRNA level and based on this an $IC_{50}$ of 8 nM was calculated (see hereinabove and FIG. 25). In comparison, out of 34 ASOs analyzed in the Monia et al. study, the best sequence, "ISIS5132", had an $IC_{50}$ of 50 nM (Monia et al. (1996) Nat. Med., 2:668-75).

Figure 26:
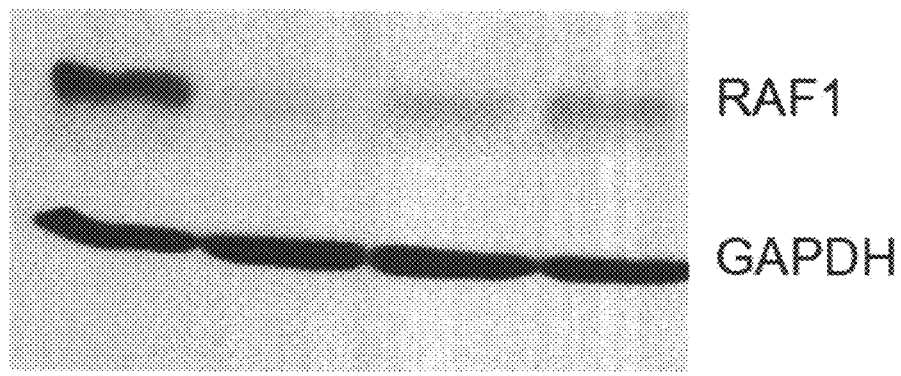
Figure 27:
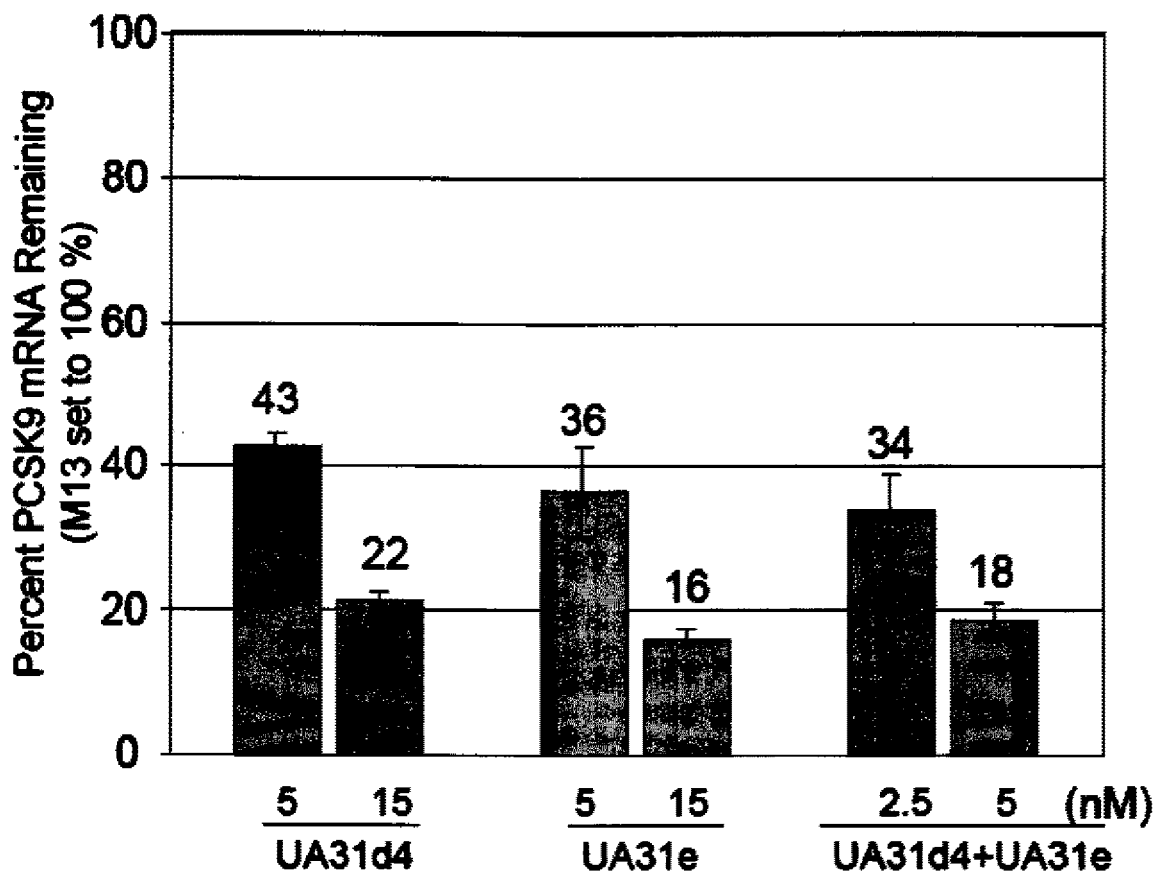

Three more anti-RAF1 U1 Adaptors were designed that targeted sites in the terminal exon of RAF1 which were predicted to be uninvolved in unstructured areas of the mRNA and fit general antisense design criteria (McQuisten et al. (2007) BMC Bioinformatics, 8:184.). All three inhibited RAF1 expression and were about 2-fold less active than UA25 (FIG. 26). As functional data becomes available for a greater number of U1 Adaptors, it may be possible to develop algorithms which predict effective target sites. To support the generality of the U1 Adaptor method, a second human gene, PCSK9, was targeted (FIG. 27). As shown, two anti-PCSK9 U1 Adaptors each silenced the target with an $IC_{50}$ in the 4-5 nM range. Importantly, simultaneous targeting of PCSK9 with both anti-PCSK9 U1 Adaptors gave enhanced inhibition, similar to what was previously observed for the Renilla reporter (see hereinabove). U1 Adaptors by definition have two domains, however none of the experiments so far have demonstrated the domains must be linked. To examine this, "half" Adaptors were tested that have either an isolated U1 Domain or an isolated Target Domain. As shown in FIG. 28, transfection of half Adaptors either alone or together failed to inhibit the target gene demonstrating that the Target and U1 Domains must be linked for inhibition to occur. The requirement for an intact bifunctional oligonucleotide to trigger suppression further argues against involvement of any traditional antisense mechanism of action.

Combining U1 Adaptors with siRNAs Gives Enhanced Silencing

Figure 29:
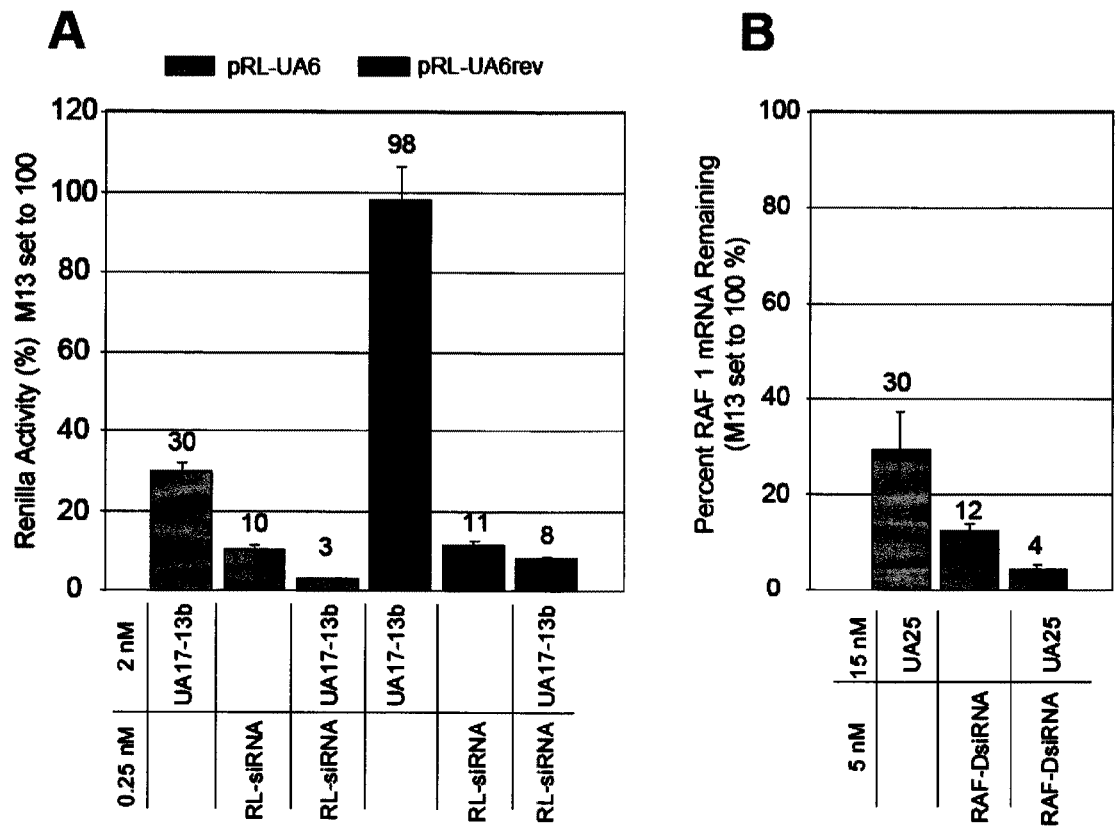
Figure 30:
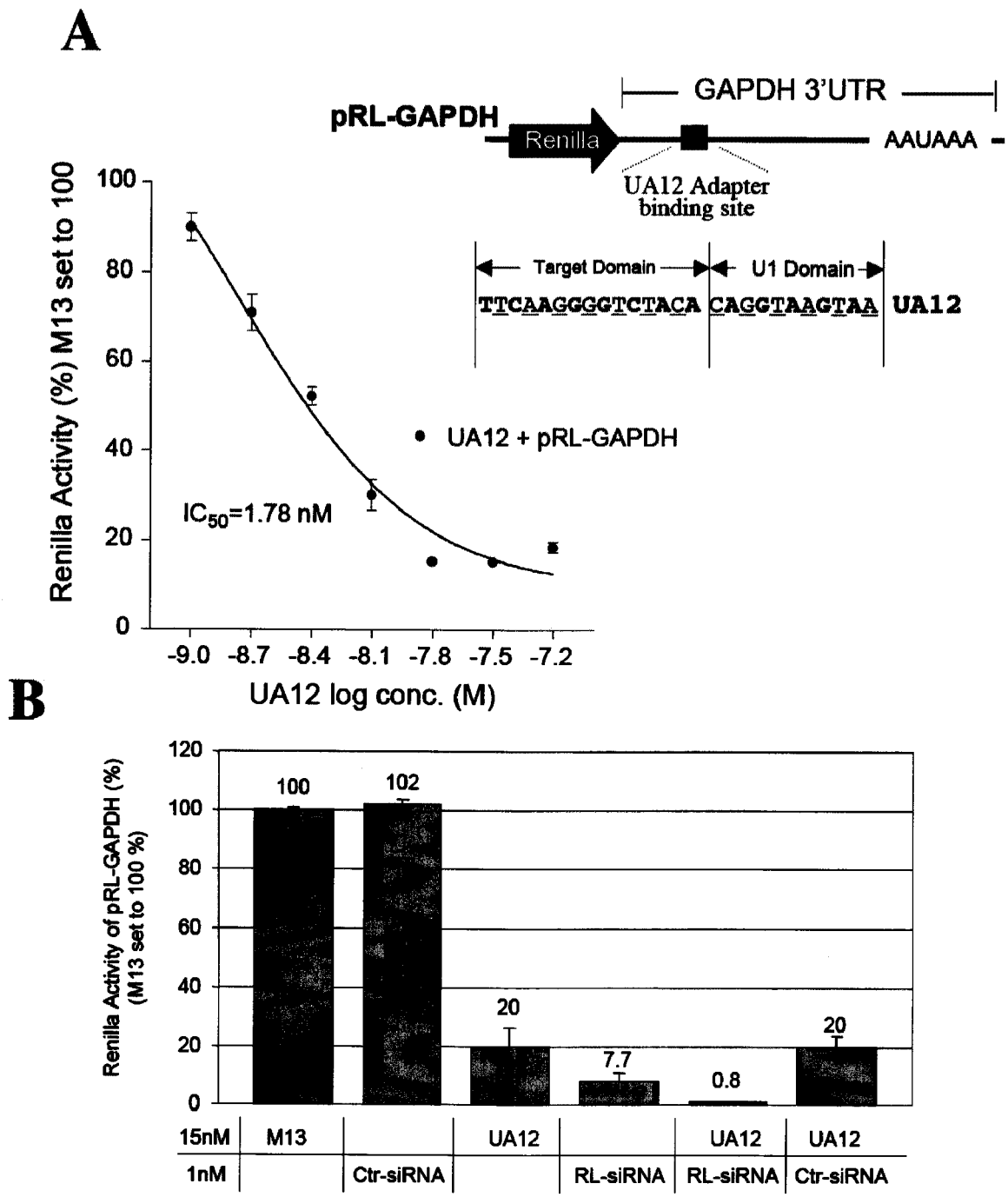

U1 Adaptors and siRNAs utilize distinct mechanisms of action that occur in different compartments of the cell (nucleus versus cytoplasm). Thus their combined use to target a single gene would be predicted to give additive inhibition; additive inhibition has already been reported for the combination of ASOs and siRNAs (Hemmings-Mieszczak et al. (2003) Nucleic Acids Res., 31:2117-26). To test this, the pRL-UA6 Renilla reporter plasmid was targeted with an anti-Renilla siRNA (RL-siRNA) and the UA17-13b Adaptor (FIG. 29). Co-transfection of RL-siRNA with UA17-13b improved inhibition as compared to use of the siRNA or U1 Adaptor alone. Negative control oligonucleotides (Control siRNA and the mutated UA7a Adaptor) did not reduce Luciferase expression. The specificity of this additive inhibition is shown by use of the pRLUA6rev reporter that has the 15 nt UA6 binding site in reverse orientation. As expected, the RLsiRNA decreased expression of pRL-UA6rev, however the UA17-13b Adaptor had no effect on pRL-UA6rev expression either when used alone or in combination with RL-siRNA. Lack of inhibition when the target site is in the inverted orientation, as with the UA6 Adaptor on pRLUA6rev, argues against repression being at the transcriptional level or being mediated by the UA6 Adaptor binding to its target site in the dsDNA plasmid. Finally, analysis of additional U1 Adaptors unrelated to UA6 demonstrated that they also function synergistically with siRNA (FIG. 30).

Figure 31:
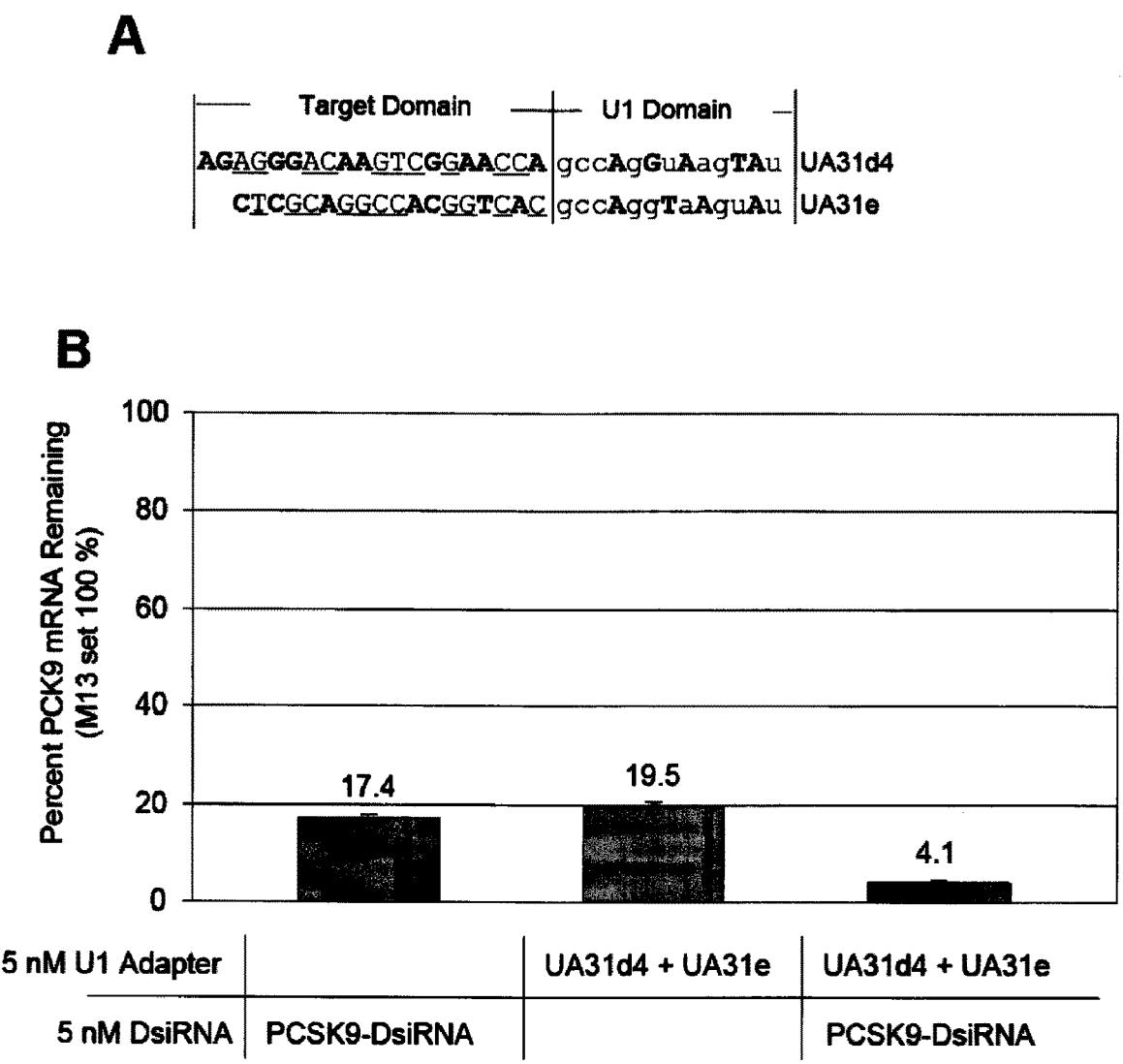

To determine whether combining siRNAs and U1 Adaptors can similarly enhance silencing of an endogenous gene, RAF1 was targeted by transfecting UA25 and an anti-RAF1 Dicer-substrate siRNA (DsiRNA) (Rose et al. (2005) Nucleic Acids Res., 33:4140-4156; Kim et al. (2005) Nature Biotechnology, 23:222-226) either alone or together. Measurement of RAF1 mRNA by qPCR demonstrated that the combined use of the U1 Adaptor and siRNA resulted in enhanced silencing (FIG. 29). Western blots confirmed that RAF1 protein levels were similarly reduced. Further, a similar degree of synergistic inhibition was observed when a siRNA and U1 Adaptors were used to silence PCSK9 (FIG. 31). Thus, it can be concluded that synergistic suppression is a general property when U1 Adaptors and siRNAs are combined to target the same gene.

Figure 32:
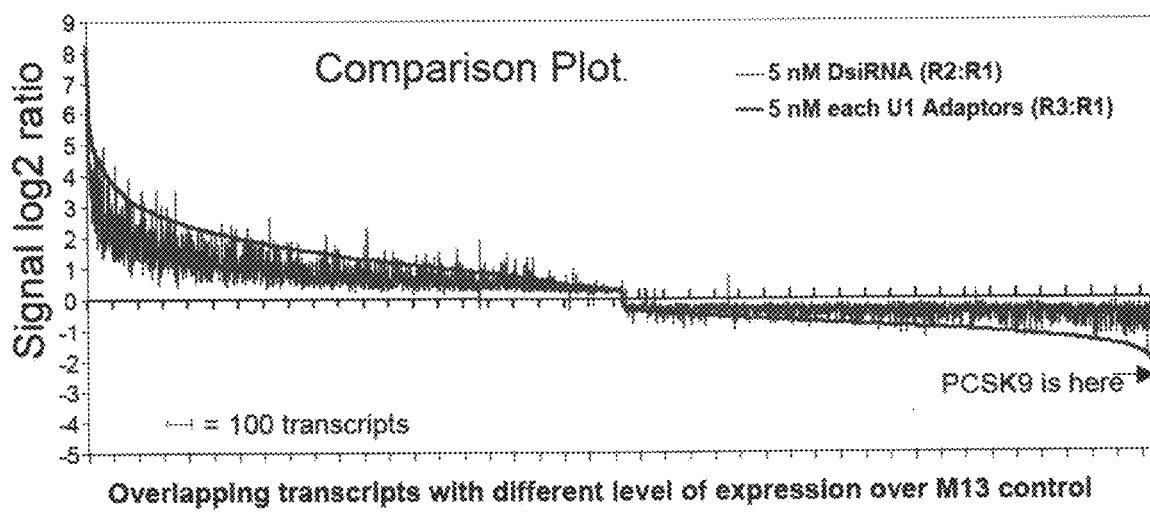
Figure 33:
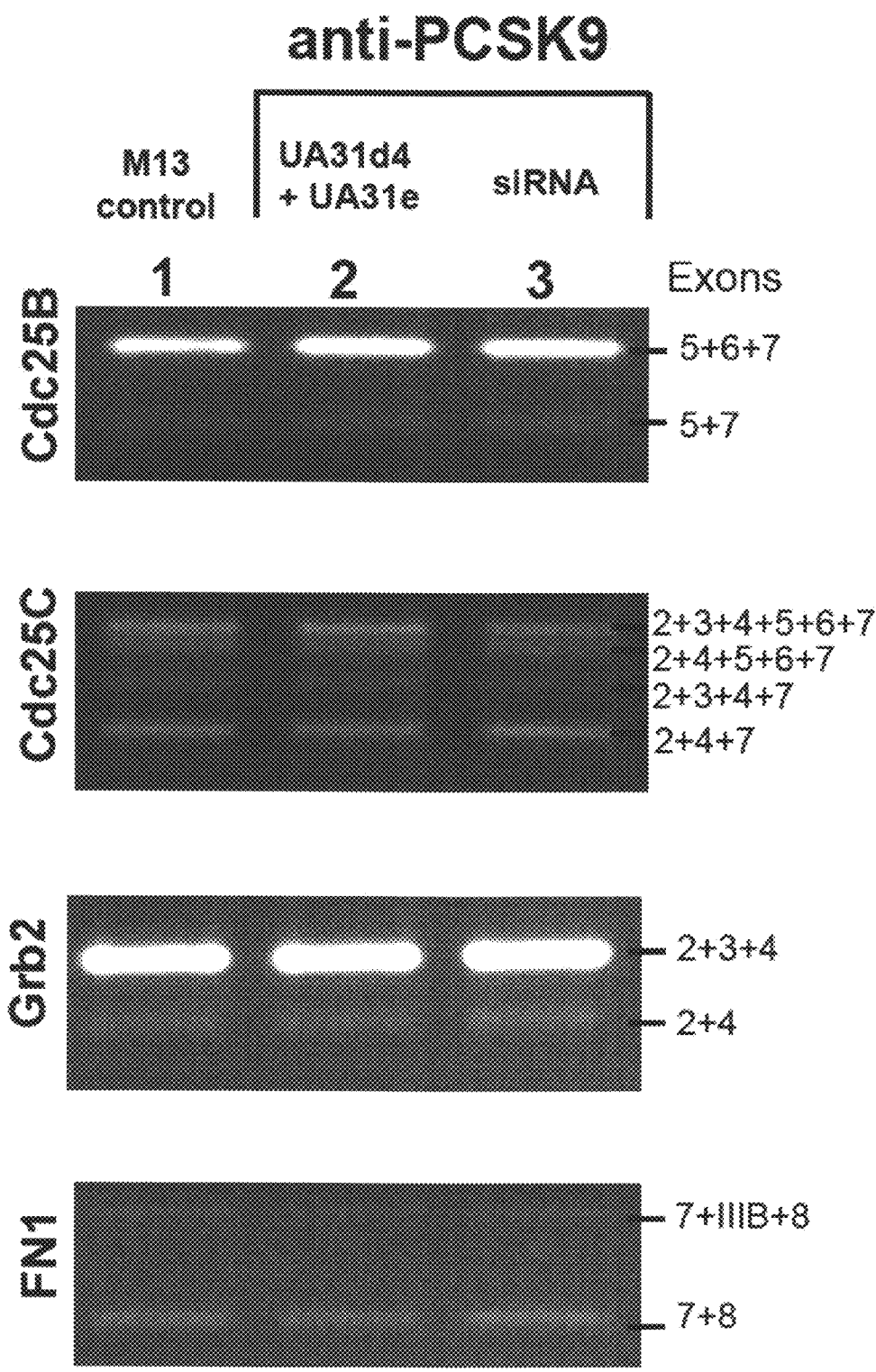

The potential for global off-target effects of the anti-PCSK9 U1 Adaptors was assessed by microarray profiling, comparing them head-to-head with an anti-PCSK9 siRNA. The results, shown in FIG. 32, indicate the two methods of gene knockdown have a very high degree of overlap (Pearson correlation of 0.93) suggesting the anti-PCSK9 U1 Adaptors do not have any new off-target effect profile when compared with the anti-PCSK9 siRNA. The U1 snRNP complex is involved in splicing to produce mature mRNA. It is possible that binding of some U1 snRNP complexes with the U1 Adaptors might adversely affect splicing within the cell. The relative splicing patterns was examined of four endogenous genes known to undergo alternative splicing and observed that the anti-PCSK9 U1 Adaptors had no discernable effect on the ratio of alternatively spliced products for these four genes, at least within HeLa cells (FIG. 33). U1 Adaptors are therefore unlikely to have a global effect on splicing, and this conclusion is further supported by the data shown earlier using the splicing reporter constructs. The determination of Adaptor specificity may be further studied with multiple U1 Adaptors and multiple gene targets using global expression profiling techniques. The above improvements to U1 Adaptor potency and design parameters reduce the potential for off-target effects, something already seen with siRNAs and ASOs.

U1 Adaptor Inhibition is at the mRNA Level

As a rigorous method to quantitate mRNA levels from Adaptor transfected cells, a Ribonuclease Protection Assay (RPA) was used to measure Renilla mRNA levels and normalized it to endogenous GAPDH mRNA levels. As described previously (Goraczniak et al. (2008) J. Biol. Chem., 283:2286-96), a Renilla RPA probe containing 100 nts of unrelated vector sequence and 295 nts that span the Renilla coding region was used that gave a 295 nt protected fragment (see FIG. 17). The *Renilla*-specific protected probe was normalized to endogenous GAPDH mRNA detected using a probe derived from a commercially available plasmid that gives a 307 nt protected product (see FIG. 17). For each transfection as well as for untransfected cells, the cells were split into two pellets, one to measure luciferase as was done in the main text and the other to make total RNA for RPA. The "5% Probe" lane is undigested probe at 5% the amount added to other lanes to show that the assay is in probe excess. To aid in quantitation and demonstrate that the assay is in the linear range, the Renilla-specific RPA was repeated with varying amounts of total RNA as shown in FIG. 17. The RPA signals were quantified by phosphoimagery and normalized to the GAPDH RPA signal. The results as given in FIG. 17D indicate Renilla mRNA levels closely correlate with Renilla activity. Using a method to fractionate cytoplasmic and nuclear RNA (Goraczniak et al. (2008) J. Biol. Chem., 283: 2286-96), cytoplasmic *Renilla* mRNA levels was found varied in the same way as in total RNA preparations. Thus the reduction in *Renilla luciferase* enzyme activity is primarily, if not completely, due to a reduction in mRNA levels.

U1 Adaptors Tether U1 snRNP to the Target mRNA

An Electrophoretic Mobility Shift Assay (EMSA) was used to demonstrate that U1 Adaptors can tether U1 snRNP specifically to a target RNA. As shown in FIG. 18, a $^{32}$P-uniformly labeled RNA (~300 nt) called UA6-RNA derived from pRL-UA6 containing the UA6 binding site was mixed with highly purified HeLa cell U1 snRNP and either the UA6 Adaptor or the UA7a negative control Adaptor and the resulting complexes resolved by native PAGE. The purification of HeLa U1 snRNP and its use in EMSA is as described (Abad et al. (2008) Nucleic Acids Res., 36:2338-52; Gunderson et al. (1998) Molecular Cell 1: 255-264) wherein U1 snRNP specifically binds to RNA containing the sequence 5'-CAG-GUAAGUA-3' (a 10 nt U1 Domain; SEQ ID NO: 1) but not to a mutated sequence 5'-CAacUcAcUA-3' (mutations in lowercase; SEQ ID NO: 76), the same mutation as found in UA7a (Abad et al. (2008) Nucleic Acids Res., 36:2338-52; Gunderson et al. (1998) Molecular Cell 1: 255-264). EMSA was done to confirm that U1 snRNP specifically binds a radiolabeled UA6 Adaptor but not UA7a. As shown in FIG. 18 lane 2, U1 snRNP did not bind direct to the $^{32}$P-UA6-RNA but was able to bind when the unlabeled UA6 Adaptor was present (lane 4). This binding depended on the U1 Domain of UA6 as no complex was observed when the UA7a Adaptor having a mutated U1 Domain was used in place of UA6 (lane 6). Thus the UA6 Adaptor specifically tethers U1 snRNP to the UA6-RNA containing the UA6 binding site. Note that under these EMSA conditions, the Adaptor-$^{32}$P-UA6-RNA complex is not readily visible as it co-migrates with the free 32P-UA6-RNA because the MW of Adaptors (<10 kDa) is far less than that of the 32P-UA6 RNA (~100 kDa).

U1 Adaptors May Have Reduced Activity when the Target Domain is Made Entirely of 2'-O-Methyl RNA (2'OMe)

It was analyzed whether U1 Adaptors with a 100%-2'OMe Target Domain maintain potency. The UA6 and UA17-10 Adaptors were included as controls and their comparison with UA-OMe1 indicates a 100%-2'OMe RNA U1 Domain maintains potency whereas a 100%-2'OMe RNA Target Domain results in reduced activity. Lengthening UA-OMe1's Target Domain to 25 nts and 35 nts failed to regain full activity. Thus, a Target Domain having either an LNA-DNA or LNA-RNA composition may be important for full U1 Adaptor activity.

U1 Adaptor Activity Correlates with their Affinity to U1 snRNP

The UA17 series of Adaptors shown herein all have various inhibitory activities that are presumably due to different affinities to U1 snRNP. To directly test their relative U1 snRNP affinities, a competition assay between various unlabeled UA17 Adaptors and a $^{32}$P-labelled RNA called U1D-RNA having an 11 nt U1 Domain (U1D) was performed as shown in FIG. 20. For all lanes, the amount of the U1 snRNP: 32P-labelled U1D-RNA complex was quantitated by phosphoimagery and is a measure of the ability of the unlabeled UA17 Adaptor to compete for U1 snRNP binding with the absence of competitor (lane 2) being set to 100%. The UA17-7 Adaptor could not compete for binding to U1 snRNP consistent with it having no inhibitory activity in cells. The increasing ability of the other UA17 Adaptors to compete, tightly correlates with their increasing inhibitory activity (see hereinabove). Thus the simplest explanation for the various activities of the UA17 series is their different relative affinities to U1 snRNP.

U1 Adaptors with a 100% LNA Target Domain are Active

It was also determined whether U1 Adaptors with an all LNA Target Domain maintain potency. To this end the UA24-12 and UA24-15 Adaptors that match UA17-10 except they have a 12 nt or 15 nt all LNA Target Domain, respectively, were analyzed (see hereinabove). As shown these U1 Adaptors were active on pRL-UA6 but not pRL-UA6rev indicating specific activity is maintained when the Target Domain is comprised entirely of LNA nucleotides. As complete conversion to LNA modified nucleotides inhibit RNase H activity, it can be concluded that the mechanism of these Adaptors does not involve RNase H.

U1 Adaptors with a Phosphorothioate (PS) Backbone are Active

Nucleotides with a PS backbone are commonly included in antisense oligonucleotides (ASOs) as they increase half life in vivo by increasing nuclease resistance. The U1 Adaptors will likely have some improved nuclease stability compared with DNA due to incorporation of LNA residues, however further stabilization of the U1 Adaptors with PS internucleoside modifications would be predicted to improve function in vivo, especially if intravenous administration is considered. Widespread inclusion of PS bonds in siRNA decreases activity for this class of gene-knockdown reagent; recent studies have shown, however, that limited PS modification is compatible with active siRNAs (reviewed in Giles et al. (1995) Nucleic Acids Res., 23:954-61; Dahlgren et al. (2008) Nucleic Acids Res., 36:e53). As the U1 Adaptor method does not require compatibility with any enzymatic activity, it was expected that extensive PS modifications would not impair activity. To test this hypothesis, a set of U1 Adaptors that were fully PS-modified were tested as shown hereinabove. The results show that the PS backbone does not significantly impair U1 Adaptor activity.

Specificity Assessed by a Mutation/Compensatory Mutation Analysis

U1 Adaptor specificity is based on the Target Domain having perfect complementarity to a sequence within the target mRNA's terminal exon. However, it is unknown what level of inhibition would occur for mRNAs with varying degrees of less-than-perfect complementarity to the U1 Adaptor. To assess specificity, three versions of UA17-13b were tested having 1, 2 and 3 nt changes in the Target Domain and observed increasingly reduced activity (FIG. 23). A single base mutation cause around a 50% reduction in inhibition and the 3 base mutation was inactive. A reporter called pRL-UA6-m3 was also made and tested that has a 3 nt compensatory mutation that fully restores complementarity to the UA17-m3 Adaptor and found a full restoration of inhibitory activity. This cross validation analysis was continued by testing the activity of UA17-ml and UA17-m2 on pRLUA6-m3 and it was found intermediate levels of inhibition. In all cases a 3 nt mismatch abrogated inhibition, whereas a 1 nt mismatch had partial to nearly full inhibition depending on which U1 Adaptor was paired with which reporter, and 2 nt mismatches had intermediate inhibition ranging between the inhibition seen for 1 and 3 nt mismatches. Thus U1 Adaptors exhibit partial activity on less-than-perfect target sequences, a fact that is commonly observed for both ASO-based silencing and for certain siRNAs. ASOs typically rely primarily upon nucleic acid hybridization for specificity and there is a trade-off between "high affinity, high potency, lower specificity" reagents and "lower affinity, lower potency, higher specificity" reagents (Giles et al. (1995) Nucleic Acids Res., 23:954-61; Lennox et al. (2006) Oligonucleotides 16:26-42). Specificity for siRNAs is influenced by poorly understood interactions between the siRNA guide strand, the mRNA target and Ago2 in RISC. Depending on the position of the base mismatch, siRNAs can show single base specificity or can show full activity even in the face of several adjacent mutations (Dahlgren et al. (2008) Nucleic Acids Res., 36:e53; Schwarz et al. (2006) PLoS Genet., 2:e140; Du et al. (2005) Nucleic Acids Res., 33:1671-7).

U1 Adaptors do not Effect Splicing of a Reporter Gene

As U1 Adaptors tether U1 snRNP, it is possible that unintended cross-hybridization to non-terminal exon regions within a pre-mRNA could affect splicing. As shown in FIG. 24, It was directly tested whether U1 Adaptors can affect pre-mRNA splicing of a transcript that they are designed to basepair with. First, a splicing reporter plasmid (pFN) was constructed that contains a 3000 bp segment of the human Fibronectin gene. The 15 nt UA6 binding site, that was sufficient to fully confer U1 Adaptor inhibition to the pRLUA6 Renilla reporter, was inserted into four distinct positions within pFN (FIG. 24A) including intronic positions and the first and last exons. In all cases the reverse orientations were also included to test whether an affect would be mediated at the DNA level. A long intron was selected as this would allow for more time for annealing of the U1 Adaptor to the pre-mRNA so as to increase the likelihood of observing a U1 Adaptor mediated affect. The UA17-13b Adaptor was chosen as this is the most potent U1 Adaptor to the UA6 binding site. Note that this segment of Fibronectin contains a 273 nt alternatively spliced exon (Exon IIIB) that is included about 10% of the time in HeLa cells (see FIG. 33 for endogenous Fibronectin splice isoforms). Exon IIIB inclusion could not be reliably detected when performing RT-PCR analysis of HeLa cells transfected with pFN, even when 40 PCR cycles were used. In contrast, the major spliced product that joins Exon III7b direct to Exon III8a could be readily detected (FIG. 24), thus it could be determined whether the UA17-13b Adaptor would affect splicing. Each of the nine pFN-related plasmids were transfected either with the M13 control or with 5 nM of the UA17-13b Adaptor and after 24 hours the cells were harvested and analyzed by RT-PCR. Given that the pRN-3for plasmid has the U1 Adaptor binding site in the terminal exon in the forward orientation, its splicing was expected to be inhibited. As shown in FIG. 24B, lane 18 this was the case. In contrast, none of the other pFN plasmids exhibited a change in their splicing pattern or efficiency when 5 nM UA17-13b was co-transfected. The primers were demonstrated to be specific for the pFN plasmid as no RT-PCR product was observed in the non-transfected cells (lanes 11 and 22). For all samples, uniform RT-PCR bands were obtained for the Arf1 housekeeping gene demonstrating the RNA samples and the RT-PCR were of similar quality. Note that 5 nM UA17-13b Adaptor gives a 9.5-fold inhibition of the pRL-UA6 reporter that has the binding site in the terminal exon. Thus it can be concluded that any affect it may have is minor when not targeting the terminal exon. Finally, it should be noted that these results are consistent with the prior work that mis-targeting U1 snRNP does not affect expression levels unless U1 snRNP is targeting the 3' terminal exon (Fortes et al. (2003) Proc. Natl. Acad. Sci. USA, 100:8264-8269; Beckley et al. (2001) Mol. Cell Biol., 21:2815-25).

PARP Cleavage when RAF1 is Silenced

It is demonstrated herein that RAF1-specific silencing with the anti-RAF1 UA25 Adaptor. It has been shown that silencing of RAF1 leads to induction of PolyA RiboPolymerase (PARP) cleavage as part of induction of an apoptotic pathway (Lau et al. (1998) Oncogene 16:1899-902). To demonstrate that the anti-RAF1 UA25 Adaptor had the same property, Western blotting was performed to visualize PARP. The results shown hereinabove demonstrate that the anti-RAF1 UA25 Adaptor induces cleavage of PARP. Other Western blotting showed that PARP cleavage is dependent on the dosage of UA25 Adaptor used and closely parallels the degree of silencing of RAF1 protein.

Additional Anti-RAF1 U1 Adaptors can Also Silence RAF1

To demonstrate silencing of RAF1 was not unique to the UA25 Adaptor, three more anti-RAF1 Adaptors called UA27, UA28 and UA29 were designed and tested as shown in FIG. 26. As was done previously, each Adaptor was transfected into HeLa cells and cells were harvested after 24 hours and analyzed by Western blot. The results demonstrate that the UA27, UA28 and UA29 Adaptors can each silence RAF1 expression. Dose dependence analysis indicted these three Adaptors have an activity level about 2-fold less than UA25.

"Half" Adaptors with Either Just the U1 or Target Domain are Inactive

Although it is likely that U1 Adaptors inhibit by tethering U1 snRNP to gene-specific pre-mRNA, the data presented do not formally rule out the possibility that the separate actions of each domain of the U1 Adaptor causes inhibition of the target RNA. For example, the U1 Domain might titrate out some U1 snRNP and affect processing of the pre-mRNA, possibly "sensitizing" the mRNA to annealing of the Target Domain. In addition, the Target Domain "half" might trigger an antisense response and lead to reduction of mRNA levels independent of the presence of U1 snRNP. If this were the case, then unlinking the two domains to create "half" Adaptors should still result in gene specific inhibition. In FIG. 28 the inhibitory activity of "half" Adaptors having either the Target Domain or the U1 Domain were determined against the pRL-UA6 reporter (FIG. 28A) and against the PCSK9 endogenous gene (FIG. 28B). In neither case were the half Adaptors capable of inhibition either when transfected alone or together. Thus, U1 Adaptor activity requires that the Target and U1 Domains be covalently linked. To determine whether inclusion of spacer sequences between the U1 and Target Domains would affect function, a set of U1 Adaptors with spacer nucleotides ranging in length from 2-6 nts was tested. In all cases such spacers did not have a significant impact on activity. Given these results, it may be expected that non-nucleotide spacers will also support U1 Adaptor activity.

Enhanced Silencing of *Renilla* is Seen when Using a Different U1 Adaptor and an Anti-*Renilla* siRNA Together to Target a *Renilla* Reporter Hereinabove, it was shown that the combined use of siRNA and the UA17-13b Adaptor gave enhanced silencing of a *Renilla luciferase* reporter. To demonstrate that this is not unique to the UA17-13b Adaptor and target site, these experiments were repeated in a different sequence context using the UA12 Adaptor that targets a site in the human GAPDH 3'UTR. As shown in FIG. 30A, the UA12 Adaptor specifically inhibits expression of a *Renilla* reporter containing the GAPDH 3'UTR (called pRLGAPDH) with an $IC_{50}$ of 1.8 nM. As shown in panel B, the combined use of an anti-Renilla siRNA and UA12 gave enhanced silencing of pRL-GAPDH, far better than when the siRNA and UA12 Adaptor were used alone.

Combining siRNAs and U1 Adaptors Gives Enhanced Silencing of an Endogenous PCSK9 Gene To demonstrate enhanced silencing when the U1 Adaptor method is combined with siRNAs is also applicable to endogenous genes, human PCSK9 was targeted using both U1 Adaptors and siRNAs. As shown in FIG. 31, the combined use of anti-PCSK9 siRNA and an anti-PCSK9 U1 Adaptor resulted in enhanced levels of silencing when compared with silencing when each method was used alone. Enhanced silencing is seen in other contexts when both methods are used together. Thus, the above supports the conclusion that enhanced levels of silencing are seen when U1 Adaptors and siRNAs are employed together targeting the same gene.

Global Expression Analysis Comparing U1 Adaptors to siRNAs

The data presented so far show U1 Adaptors specifically silence a target reporter plasmid as compared to a control reporter plasmid and silence a target endogenous gene as compared to GAPDH. Such experiments do not address whether and to what degree U1 Adaptors affect the abundance of non-targeted mRNAs. Such off-target affects can arise from the U1 Adaptor mistargeting either the polyA site regions of other genes or upstream exons or introns that would result in changes in the splicing pattern. As a first test to assess the global specificity of U1 Adaptors, the anti-PCSK9 U1 Adaptors were compared head-to-head with the anti-PCSK9 siRNA by microarray profiling. The total RNA preparations used in FIG. 31, namely the M13 control, the anti-PCSK9 DsiRNA and the anti-PCSK9 UA31d4+UA31e, were subjected to microarray analysis with the Affymetrix human U133 chip that detects ~54,000 human mRNAs. A scrambled siRNA control or a mutated control U1 Adaptor were not included as the overall number of genes being effected by each method was assessed without normalization to a control. In order to do a global comparison of the two methods, it was important that they have the same fold reduction in PCSK9. As shown in FIG. 32A, this was the case as qRT-PCR analysis gave a 5.7-fold knock down for the anti-DsiRNA and a 5.1 fold knock down for the anti-PCSK9 U1 Adaptors. Importantly both the microarray and qRT-PCR knockdown values were in good agreement validating the quality of the microarray data. If the anti-PCSK9 U1 Adaptors and siRNA were perfectly specific, then in principle their global expression profiles should be perfectly correlated. Panel B is a comparison plot of all the genes that showed ≧2-fold change for either the U1 Adaptors or the DsiRNA. The line represents the ≧2-fold-affected genes from the U1 Adaptor transfection that are sorted from the largest increase to the largest decrease. The vertical lines indicate the corresponding genes from the DsiRNA transfection. If both the U1 Adaptor and siRNA methods were perfectly specific then one would expect the curve and the vertical lines to perfectly overlap. A lack of correlation would be, for example, when a U1 Adaptor gene is strongly up-regulated while the DsiRNA gene is unaffected or downregulated. A visual inspection shows that there is a high degree of correlation between the U1 Adaptor- and DsiRNA-affected genes suggesting that the U1 Adaptor method does not result in any larger degree of off-target effects than resulting from using RNAi. Plotting the data as the log 2 ratio of PCSK9-U1 Adaptor against the log 2 ratio of PCSK9-siRNA gives a Pearson correlation of 0.93.

U1 Adaptors Have No Apparent Effect on Alternative Splicing Pattern of Certain Genes Although microarray data gives a snapshot of the global mRNA expression levels it is less reliable at detecting changes in alternative splicing patterns, especially if such changes affect minor spliced isoforms of a gene. U1 Adaptors could affect splicing either by mis-annealing to a non-targeted pre-mRNA or by titrating out sufficient amounts of U1 snRNP so as to affect splicing in general. To address the latter four genes were examined that are alternatively spliced in HeLa cells as such splicing involves suboptimal splice signals that should in principle be more sensitive to reduced spliceosome activity caused by titrating out U1 snRNP by U1 Adaptors. It has recently been shown that the splicing patterns of the alternatively spliced isoforms of the human Cdc25B and Cdc25C genes are sensitive to changes in the levels of the canonical U2AF35 splicing factor (Pacheco et al. (2006) Mol. Cell Biol., 21:8183-90). If the anti-PCSK9 U1 Adaptors were titrating out U1 snRNP then this might lead to limitations in spliceosome complex formation that would mimic a depletion in U2AF35 levels. As shown in the upper two panels of FIG. 33, RT-PCR analysis of these genes showed no discernable change in their splicing patterns. Two additional genes namely Grb2, a signal transduction gene, and Fibronectin, were analyzed where both genes have a minor isoform (Grb2's is exon 3-skipped and Fibronectin's is Exon IIIB included) that increases in abundance during stress and this increase is due to changes in splicing efficiency (Li et al., J. Biol. Chem., 275:30925-33; Kornblihtt et al. (1996) FASEB J., 10:248-57). As shown in FIG. 33, RT-PCR analysis demonstrated that the anti-PCSK9 U1 Adaptors had no discernable effect on the splicing pattern of either Grb2 or Fibronectin as compared to either the M13 control or the anti-PCSK9 siRNA. Thus it can be concluded that the anti-PCSK9 U1 Adaptors are unlikely to have a global affect on splicing, a conclusion qualified by the fact that a concerted effort to measure all spliced isoforms in U1 Adaptor transfected HeLa cells could be done to more fully address this issue.

Comparison of Features Between U1 Adaptor, siRNA and ASO Methods

FIGS. 34 and 35 list the U1 Adaptor and siRNA sequences used in this report. FIG. 36 briefly summarizes what is known about the U1 Adaptor method and compares it with siRNA and ASO gene silencing methods.

Discussion

A novel oligonucleotide-based gene silencing method called U1 Adaptor Technology is described herein that reduces gene expression by tethering the U1 snRNP splicing factor to the target pre-mRNA. Successful inhibition was demonstrated at both mRNA and protein levels and was studied for both a reporter gene and two endogenous human genes. Potent inhibition was observed with an $IC_{50}$ as low as 0.5 nM seen in the data presented here. Potency in the sub-nanomolar range can routinely be achieved using this method. Within the limited set of U1 Adaptors studied so far, a success rate of approximately 50% was observed in obtaining U1 Adaptors with ≦5 nM $IC_{50}$ potency by applying antisense oligonucleotide selection criteria to the target genes.

There are several considerations which support the prospect of using. U1 Adaptors in vivo and potentially for therapeutic indications. First, in vivo administration of synthetic oligonucleotides such as U1 Adaptors can employ the same delivery technologies already pioneered for use with siRNA and antisense methods (Meister et al. (2004) Nature 431:343-9; Judge at al. (2006) Mol. Ther., 13:494-505; Soutschek et al. (2004) Nature 432:173-8; Morrissey et al. (2005) Nat. Biotechnol., 23:1002-7). Second, U1 Adaptors can include extensive modified nucleotides which result in molecules that are likely to have a high degree of nuclease stability, especially when phosphorothioate modified. Further, no enzymatic activity is involved in their function; this permits use of a wider range of modifications in U1 Adaptors than are compatible with siRNAs or traditional antisense oligonucleotides, which require direct interaction with cellular enzymes (Ago2, Dicer, RNase H, etc.) (Meister et al. (2004) Nature 431:343-9; Manoharan, M. (2004) Curr. Opin. Chem. Biol., 8:570-9; Crooke, S. T. (2004) Curr. Mol. Med., 4:465-87). Third, the synergistic activity of several U1 Adaptors used together or in combination with siRNAs allows for use of lower doses of each individual oligonucleotide, reducing the potential for toxic side effects and lowering cost of administration. Importantly, the most active U1 Adaptors described here were made entirely of 2'OMe RNA and LNA residues; this chemical composition does not contain motifs that are known to trigger the innate immune system. FIG. 36 summarizes a comparison of the U1 Adaptor method with antisense and RNAi methods.

Besides U1 snRNP, there are other RNA processing factors that are known to inhibit polyA site activity and hence gene expression (Zhao et al. (1999) Microbial. Mol. Biol. Rev., 63:405-45; Danckwardt et al. (2008) EMBO J., 27:482-98). Novel Adaptors could be designed to similarly recruit these other factors, either individually or in combination. However, there are several features unique to U1 snRNP. First, U1 snRNP is highly abundant with about 1 million copies present in a typical mammalian nucleus (~0.5 µM U1 snRNP in a HeLa cell, far higher in the nucleus) and is in ~10-fold stoichiometric excess over the spliceosome (Will et al. (1997) Curr. Opin. Cell Biol., 9:320-8). Thus, without being bound by theory, it is plausible that sequestering a small fraction of U1 snRNP by interaction with low nM amounts of U1 Adaptors will have little effect on the overall splicing machinery and will not deplete the pool of U1 snRNP available. Second, the functional in vivo concentration of U1 snRNP, defined by the degree of inhibition observed when inserting a U1 snRNP binding site near a reporter gene's polyA signal, is much higher when compared to these other RNA processing factors (Fortes et al. (2003) Proc. Natl. Acad. Sci. USA, 100:8264-8269; Ko et al. (2002) J. Mol. Biol., 318:1189-206). Third, it is rather straight-forward to increase U1 snRNP's affinity with the U1 Adaptor as evidenced by the data herein. Nevertheless, new Adaptor designs can be identified that inhibit gene expression by interaction with other RNA processing factors.

Example X

The ability to silence a single target gene while minimizing toxicity and off-target effects (OTEs) would offer the medical community a new, broadly-applicable tool to combat a wide variety of diseases both prophylactically and therapeutically. A variety of hybridization-based technologies have been tested that utilize synthetic nucleic acid oligonucleotides to suppress expression of a specific target gene. These technologies are, broadly speaking, based on a gene being targeted either by a small interfering (si) RNA as part of the RNAi mechanism (Kim et al. (2007) Nat. Rev. Genet., 8:173-84; Castanotto et al. (2009) Nature 457:426-33; Krueger et al. (2007) Oligonucleotides 17:237-50) or by an antisense oligonucleotide (ASO) (Kurreck, J. (2003) Eur. J. Biochem., 270:1628-44) that can encompass a variety of mechanisms, but most typically involve RNase H-mediated cleavage of RNA or steric hindrance of mRNA translation. ASOs and siRNAs have yet to produce a commercial therapeutic, in spite of initial hype and large-scale investment (Castanotto et al. (2009) Nature 457:426-33). Therapeutic ASO has struggled primarily because of modest potency and poor genome-wide specificity. Therapeutic siRNA although making tremendous progress since siRNAs were first described in 2001, suffers from immune activation (now largely solved), inherent poor stability and difficulty in delivery (still not solved), and general concern over adversely affecting the cell's natural microRNA pathway (not easy to solve).

The instant invention of U1 Adaptor gene silencing technology circumvents these problems, as it represents a far more chemically flexible oligonucleotide platform, enabling generation of stable, potent molecules with high specificity and ease of delivery. Unique features of the instant invention indicate that it will be far more potent than other oligonucleotide-based silencing methods when used in vivo including therapeutic silencing. As their inhibitory mechanism does not require enzymatic activity, the U1 Adaptor oligonucleotides of the instant invention can withstand up to 100% modification of their backbone and covalent attachment of delivery groups (e.g. peptides) enabling optimal stability and delivery capabilities. For example, the chemical composition of active U1 Adaptors can include 2'-O-Methyl (2'OMe) and phosphorothioate (PS) at every position as well 5' or 3' end modification with bulky chemical groups such as biotin or fluorescent groups (e.g., Cy3). This makes U1 Adaptors superior to siRNAs or traditional ASOs that become inactive when so heavily modified (Kim et al. (2007) Nat. Rev. Genet., 8:173-84; Castanotto et al. (2009) Nature 457:426-33; Kurreck, J. (2003) Eur. J. Biochem., 270:1628-44). Such a chemically flexible platform will allow the U1 Adaptor to be more highly stable and deliverable in vivo compared to siRNA or ASO. An additional feature is the ability to observe additive and striking synergistic inhibition when multiple U1 Adaptors are used to simultaneously target a single gene or when a U1 Adaptor and siRNA target a single gene, consistent with the fact that these two methods utilize distinct mechanisms of action (blocking pre-mRNA maturation versus destabilizing mature mRNA) that occur in different compartments of the cell (nucleus versus cytoplasm). This type of multiplexing to target a single gene permits deeper silencing while using less inhibitory molecules.

Here, the in vivo use of U1 Adaptor is demonstrated by targeting two human proteins that have been proposed to be important in melanoma in a human melanoma cell xenograft mouse model. The human B-cell lymphoma 2 (BCL2) gene has long been a target for oligonucleotide-based therapeutics (Danial et al. (2004) Cell 116:205-219; Miller et al. (2006) N. Engl. J. Med., 355:51-65; McGill et al. (2002) Cell 109:707-718; Zhao et al. (2007) J. Control Release 119:143-52; Loriot et al. (2010) Anticancer Res., 30:3869-78; Jansen et al. (2000) Lancet 356:1728-33) whereas, the human metabolotropic Glutamate Receptor 1 (Grm1) gene has more recently been established as a key player in melanoma as well as other cancers including the finding that ectopic expression of Grm1 in melanocytes is sufficient to induce melanocytic cell transformation in vitro and spontaneous melanoma development in vivo (Pollock et al. (2003) Nat. Genet., 34:108-12; Shin et al. (2008) Pigment Cell Melanoma Res., 21:368-78). A novel tumor-specific targeting vehicle suitable for U1 Adaptor use in vivo is also provided. Unprecedented potency is demonstrated herein with as little as 5.1 µg anti-BCL2 Adaptor needed to observe 85% suppression of tumor volume in a xenograft mouse model of melanoma with little apparent organ toxicity. These results demonstrate that U1 Adaptor is a highly-potent gene-silencing therapeutic that exhibits a tumor suppression potency far greater than other oligonucleotide-based therapeutics.

Materials and Methods

Xenografts in immunodeficient nude mice. All animal studies were approved by the Institutional Review Board (IRB) for the Animal Care and Facilities Committee of Rutgers University. Male nude mice (5 weeks old) were purchased from Taconic (Hudson, N.Y.). Human melanoma cells, C8161 or UACC903, were injected into the dorsal area at $10^6$ cells per site. Tumors were measured once a week with a vernier caliper and tumor volume (V; cubed centimeters) was calculated by using the equation $V=d^2 \times D/2$, where d (squared centimeters) and D (centimeters) are the smallest and largest perpendicular diameters. Once tumors reached 10 mm$^3$, the animals were divided randomly into treatment groups so that the mean difference in tumor size between each group was <10%. Mice were sacrificed after approximately 3 weeks (for C8161) or 5 weeks (for UACC903) corresponding to when the tumor volume in the vehicle-treated group had reached the maximum size permitted by the IRB. The tumor xenografts were excised for further histological and molecular analyses.

Immunohistochemistry. The Tissue Analytical Services at the Cancer Institute of New Jersey performed all the immunohistochemical staining of excised tumor xenografts to detect changes in apoptosis and proliferation using well-known activated Caspase 3 and Ki-67 markers, respectively.

Statistics. The number of mice used for each experiment was determined with the help from the Biometrics Facility Core at the Cancer Institute of New Jersey. P-values were determined using unpaired Student's two-tailed t-test. A p-value of <0.05 was considered significant.

Results

The human BCL2 gene is a well-validated example of therapeutic targeting by ASO- and siRNA-based approaches (Waite et al. (2009) Bioconjug. Chem., 20:1908-16; Taratula et al. (2009) J. Control Release, 140:284-93; Yip et al. (2008) Oncogene 27, 6398-6406; Namkoong et al. (2006) Front. Biosci., 11:2081-92; Okamoto et al. (2007) J. Cell Mol. Med., 11:349-61; Hwa et al. (2010) Pigment Cell Melanoma Res., 21:415-428; Gross et al. (1999) Genes Dev., 13:1899-911; Jansen et al. (1998) Nat. Med., 4:232-234). The human GRM1 gene in contrast has little or no published examples of targeting by ASO and siRNA oligonucleotides while at the same time showing promise as a therapeutic silencing target in that shRNA-based silencing of GRM1 leads to inhibition of tumor growth both in vitro and in vivo (Pollock et al. (2003) Nat. Genet., 34:108-12; Shin et al. (2008) Pigment Cell Melanoma Res., 21:368-78). Furthermore, both BCL2 and GRM1 have demonstrated potential for treating melanoma in that they extraordinary resistance of melanoma to apoptotic cell death commonly induced by anticancer drugs is mediated in part by elevated levels of BCL2 (Danial et al. (2004) Cell 116:205-219; Miller et al. (2006) N. Engl. J. Med., 355:51-65; McGill et al. (2002) Cell 109:707-718), while GRM1's role in cancer was originally established in melanoma and is now being therapeutically targeted by small molecule inhibitors of GRM1. For xenograft mouse studies, the human C8161 cell line was used as a model of an aggressive melanoma.

Choice of an RGD-Dendrimer Delivery Agent

Figure 37:
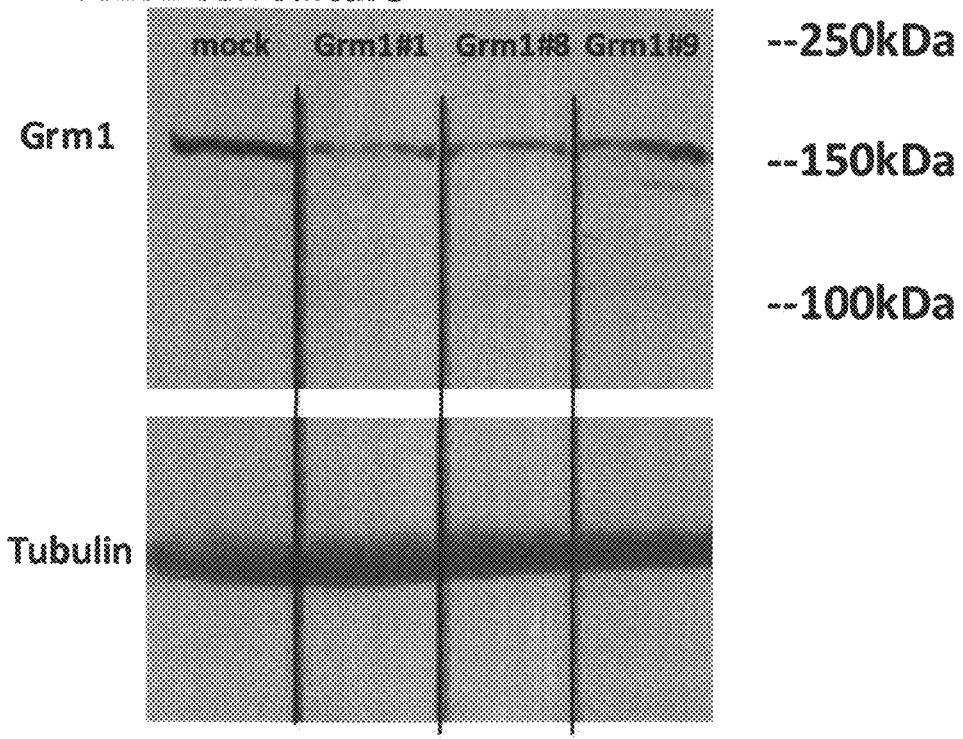

To deliver the U1 Adaptors to the tumor, the cyclic RGD pentapeptide (RGD) was used. The RGD peptide has a well-validated cancer cell-specific targeting activity both in animal models and in humans. The RGD peptide targets a specific isoform (alpha-5 beta-3) of an integrin cell surface receptor (arising from alternative splicing) that is up-regulated in a wide variety of cancer types including melanomas such as C8161 cells and is being used in several clinical trials as a tumor-specific targeting moiety for MRI-visualization of tumors (Phase I/II Study of SPC2996, an RNA Antagonist of Bcl-2, in Patients with Advanced Chronic Lymphocytic Leukaemia (CLL); Wacheck et al. (2002) Antisense Nucleic Acid Drug Dev., 12:359-67). As a delivery backbone, a polypropyleneimine (PPI) generation 5 (G5) dendrimer was used for its simplicity in the coupling of targeting moieties and that has been successfully used in xenograft mouse models of human tumors (Cheng et al. (2008) Front. Biosci., 13:1447-71; Dufès et al. (2005) Adv. Drug Delivery. Rev., 57:2177-2202; Myc et al. (2010) Anticancer Drugs 21:186-92). FIG. 37C is a schematic of the tumor-targeting delivery vehicle wherein RGD was coupled to PPIG5 at a 2:1 stoichiometric ratio to make RGD-PPIG5 by use of a bi-functional SM(PEG)$_{12}$NHS linker (Pierce, Rockford, Ill.). For simplicity, unmodified PPIG5 is referred to as "Vehicle" and RGD-PPIG5 as "RGD-Vehicle".

Anti-GRM1 Adaptors Silence GRM1 and Suppress Tumor Growth.

Screening a series of anti-human U1 Adaptors in C8161 cell culture identified three Adaptors, GRM1#1, GRM1#8 and GRM1#9 (FIG. 37A), as having superior potency to reduce GRM1 protein levels as compared to the proteins of two housekeeping genes, tubulin and GAPDH (used to demonstrate equal protein loading) as shown in the Western blot in FIG. 37B. These transfections involved adding to the C8161 cells a complex comprised of the U1 Adaptor combined with unmodified PPIG5 and then 60 hours later lysing the cells in laemmli protein-gel loading buffer. Additional cultured cell studies established both strong nuclear localization of a Cy3-fluorescently labeled Adaptor and low cytoxicity when introducing into the recipient cells via transient transfection of up to 100 nM Adaptor with either unmodified PPIG5 or RGD-PPIG5.

To assess their in vivo therapeutic activity each anti-GRM1 Adaptor was tested in a xenograft mouse system as follows. One million C8161 human melanoma cells were inoculated into both dorsal flanks of each nu/nu mouse. Mice were untreated until the tumor cell xenografts reached about 10 mm$^3$ (about 7-10 days), after which the mice were divided into treatment groups 1-4 (TG1-TG4) such that each group had a similar mean tumor volume. Each TG mouse received an intravenous (iv) injection of either the RGD-Vehicle only (the TG1 control group) or the RGD-Vehicle in complex with a specific anti-GRM1 Adaptor (TG2-TG4). Mice received treatments twice weekly for 3 weeks until they were sacrificed when the TG1 tumor volumes reached the IACUC-allowed maximum size.

Tumor volumes were measured weekly and the results as graphed in FIG. 37D demonstrate mice in the TG2, TG3 and TG4 treatment groups had significantly smaller tumors as compared to the vehicle-only TG1 mice. To establish GRM1 is silenced in tumors treated with anti-GRM1 Adaptors, tumors were analyzed by Western blotting (FIG. 37D) and as the results demonstrate, GRM1 protein levels were significantly reduced in TG2, TG3 and TG4 mice relative to TG1 control mice using GAPDH and tubulin as normalization for equal protein loading. Notably, having three validated anti-GRM1 Adaptors allows for their combining to achieve additive or synergistic tumor suppression. As discussed hereinabove, multiple U1 Adaptors targeting a single gene result in deeper silencing activity (curiously, such activity is not observed with multiple siRNAs targeting a single gene). Having such potential in vivo will provide a means of significantly lowering therapeutic doses.

Anti-BCL2 Adaptors Suppress Tumor Growth.

Having established the tumor suppression activities of the anti-GRM1 Adaptors, an analysis of the human BCL2 gene was performed. BCL2 has been implicated in a number of cancers, including melanoma, brain, breast, and lung carcinomas (Yip et al. (2008) Oncogene 27:6398-6406; Namkoong et al. (2006) Front Biosci., 11:2081-92; Okamoto et al. (2007) J. Cell Mol. Med., 11:349-61; Hwa et al. (2010) Pigment Cell Melanoma Res. 21:415-428; Gross et al. (1999) Genes Dev., 13:1899-911). Screening anti-human-BCL2 Adaptors in cultured cells (including HeLa and C8161) identified the BCL2#11 and BCL2#12 Adaptors (see FIG. 38A) as having superior potency ($IC_{50} \leq 10$ nM) to reduce human BCL2 mRNA as measured by qPCR normalized to two different housekeeping genes: HPRT1 and RPLPO.

The therapeutic activity of BCL2#11 in xenograft C8161 mice was assessed by i.v. injection that included varying the dosing amounts and times as summarized in FIG. 38B. TG5 was the control "vehicle-only" group, where each mouse was injected twice/week (Days 1, 5, 9, 12, 15) I.V. with 50 μl of 1×PBS containing 2.3 μg RGD-Vehicle over a 2.5 week period giving a total of 5 injections. Each TG6 and TG7 mouse was injected I.V. on Day 1 with 3.4 μg BCL2#11 Adaptor in complex with 4.6 μg RGD-Vehicle in 50 μl 1×PBS. Then on Day 5, each TG6 and TG7 mouse was injected again with 1.7 μg BCL2 #11 Adaptor in complex with 2.3 μg RGD-Vehicle in 50 μl 1×PBS. TG6 mice received no further treatments. In contrast, each TG7 mouse received three additional injections on Days 9, 12 and 15 day with each injection comprised of 1.7 μg BCL2 #11 Adaptor in complex with 2.3 μg RGD-Vehicle in 50 μl 1×PBS. All mice were sacrificed on Day 19 when the TG5 tumor volumes reached the IACUC-allowed maximum size.

Mice in both TG6 and TG7 had significantly smaller tumors as compared to the vehicle-only TG5 mice with TG7 having higher efficacy in suppressing xenograft tumor progression. TG6 mice only received 2 injections with a cumulative dose of 5.1 μg Adaptor/mouse (~204 μg/kg), while TG7 mice received 5 injections with a cumulative dose of 10.2 μg Adaptor/mouse (~408 μg/kg). The potency of tumor suppression by the anti-BCL2#11 Adaptor is impressive as the most potent anti-BCL2 siRNA in the literature involved i.v. injection of 200 μg siRNA daily into each mouse over 24 days giving a cumulative dose of 4800 μg anti-BCL2 siRNA/mouse (Okamoto et al. (2007) J. Cell Mol. Med., 11:349-61). In spite of such high amounts of anti-BCL2 siRNA, tumor suppression was a modest 30% as compared to the 80-90% observed in FIG. 38B. The most potent anti-BCL2 ASOs were even of lower potency involving cumulative dosing in xenograft mice in excess of 5 mg/mouse (Zhao et al. (2006) J. Control Release 119:143-52; Loriot et al. (2010) Anticancer Res., 30:3869-78). Based on these results, subsequent studies were performed with I.V. injection of a given compound twice a week until the end of the experiments.

The experiments were repeated with additional controls to further establish that tumor suppression was through a U1 Adaptor mechanism. FIG. 38C repeats the FIG. 38B experiment but simplifies the dosing regimen so all mice receive the same amount (1.7 μg) of anti-BCL2 adaptor at the same frequency (2×/week). As can be seen, this simpler and lower amount of dosing was sufficient to give tumor suppression in TG9 as compared to the TG8 RGD-Vehicle only mice. As compared to other gene silencing methods, U1 Adaptors use a novel mechanism of action that includes a unique two-domain design in the oligonucleotide. Prior work in cell culture established design criteria for several control U1 Adaptors that validate gene silencing is via a U1 Adaptor mechanism rather than via a traditional antisense mechanism. To this end, TG10 animals were treated with a control BCL2#11 Adaptor containing a mutated Target Domain (still anneals to the U1 snRNP inhibitor but not to the BCL2 pre-mRNA), while TG11 animals used a control BCL2#11 Adaptor with a mutated U1 Domain (still anneals to the BCL2 pre-mRNA but not to the U1 snRNP inhibitor). In both TG10 and TG11, tumor suppression activity was lost, showing that tumor suppression is via a U1 Adaptor mechanism.

To demonstrate tumor suppression activity requires RGD targeting, TG12 animals were treated the same as TG9 animals except the vehicle lacked the RGD targeting group. As can clearly be seen, TG12 animals exhibited no tumor suppression demonstrating tumor suppression depends on the RGD peptide. TG13 mice were treated the same as TG9 except a 5-fold lower dose of U1 Adaptor:RGD-Vehicle complex was used. The observation that TG13 exhibited no tumor suppression indicates the minimal effective dose for this xenograft system is $\leq 1.7$ μg/dose and $>0.34$ μg/dose.

Therapeutic silencing of BCL2 by either antisense or siRNA established an increased rate of apoptosis as being part of the therapeutic mechanism (McGill et al. (2002) Cell 109: 707-718 (2002); Zhao et al. (2006) J. Control Release 119: 143-52; Loriot et al. (2010) Anticancer Res., 30:3869-78; Okamoto et al. (2007) J. Cell Mol. Med., 11:349-61) as assessed by immunohistochemical staining to visualize apoptotic markers. To establish whether the anti-BCL2 Adaptors elicited the same pattern, the tumors from TG8-TG11 mice (FIG. 38C) were analyzed by Ki67 and caspase 3 staining with representative images shown in FIG. 39A and quantitation of the staining shown in the FIG. 39B graph. Comparison of TG9 with the TG8 control mice identified elevated apoptotic activity (increased caspase 3 staining as seen in FIG. 39B) and reduced proliferation (lower Ki67 staining) consistent with the reduced tumor volumes of the TG9 mice. The elevated apoptosis and lower proliferation indices were not found with the control Adaptor treated mice (TG10 and TG11) indicating they depend on simultaneous base pairing to BCL2 and U1 snRNP. Thus U1 Adaptor targeting of BCL2 but not control U1 Adaptors elevates apoptosis, a result consistent with other silencing technologies that target BCL2.

A general concern in the oligonucleotide therapeutics field has been whether such treatments are toxic to organs or tissues. Indeed it has been reported that use of milligram amounts of therapeutic oligonucleotides in mice can lead to organ toxicity. Given the far lower U1 Adaptor dosing levels used here, toxicity would likely not be apparent. Both visual and histopathological inspection of the livers and other organ systems (kidneys, spleen, heart, brain, lungs) from the TG8-TG13 mice indicated no overt toxicity. Furthermore, none of the mice exhibited overt signs of toxicity such as lethargy, not eating or drinking, loss of body weight or ulceration of the transplanted tumor.

Targeting BCL2 with a Second U1 Adaptor.

Figure 40:
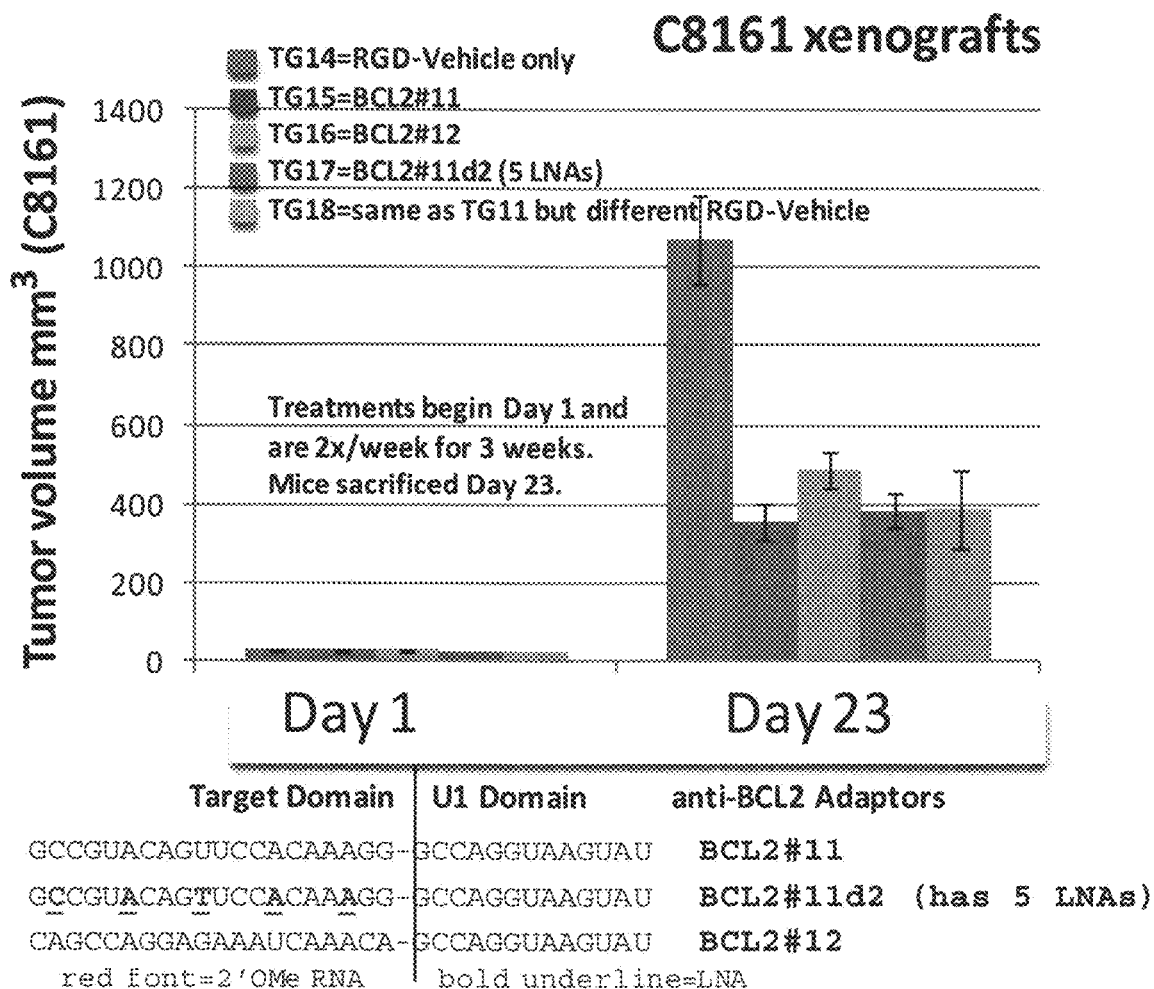
FIG. 40 shows the tumor suppression observed in mouse C8161 xenografts with BCL2#12 Adaptor compared to the BCL2#11 Adaptor. Also includes are variants of the BCL2#11 Adaptor that contains five locked nucleic acid (LNA)-modified nucleotides (top to bottom: SEQ ID NOs: 80, 83, and 84).

To further confirm tumor suppression was through silencing of the intended BCL2 gene target and not some unrecognized off-target effect of the BCL2#11 oligonucleotide, a second anti-BCL2 Adaptor (BCL2#12) was tested that targets a different region of the BCL2 gene. As shown in FIG. 40, TG16 animals receiving BCL2#12 exhibited tumor suppression with nearly the same potency as BCL2#11 (TG15) consistent with the observation in cultured cell studies where BCL2#11 is slightly more potent than BCL2#12. Having such potency, when targeting a second site in BCL2, indicates that tumor suppression is indeed acting through the BCL2 gene.

A simple method to increase oligonucleotide potency is to introduce chemical modifications that increase stability and affinity to the intended target gene's pre-mRNA. Locked nucleic acid (LNA) is one such modification that increases affinity and to this end a series of second generation variants of BCL2#11 containing LNAs in various positions were screened in cultured cells and all demonstrated to have higher potency than the original unmodified version of BCL2#11. The most effective of these (5-fold more potent than BCL2#11) was BCL2#11d2 that was then tested in TG17 mice (FIG. 40). Although BCL2#11d2 was active in tumor suppression its efficacy was matched only to that of the original BCL2#11.

To assess whether the linker itself was contributing to tumor suppression we replaced the 53.4 angstrom (predicted length) linker with a different linker, LC-SPDP (Pierce) that is far shorter (predicted 15.6 angstroms) and of a different chemical composition and tested for tumor suppression activity in the TG18 mice. As can be seen the TG18 mice exhibited a similar tumor suppression as the matching TG15 mice when both are compared to the vehicle control TG14 mice indicating the type of linker is not directly dictating tumor suppression activity.

Figure 41:
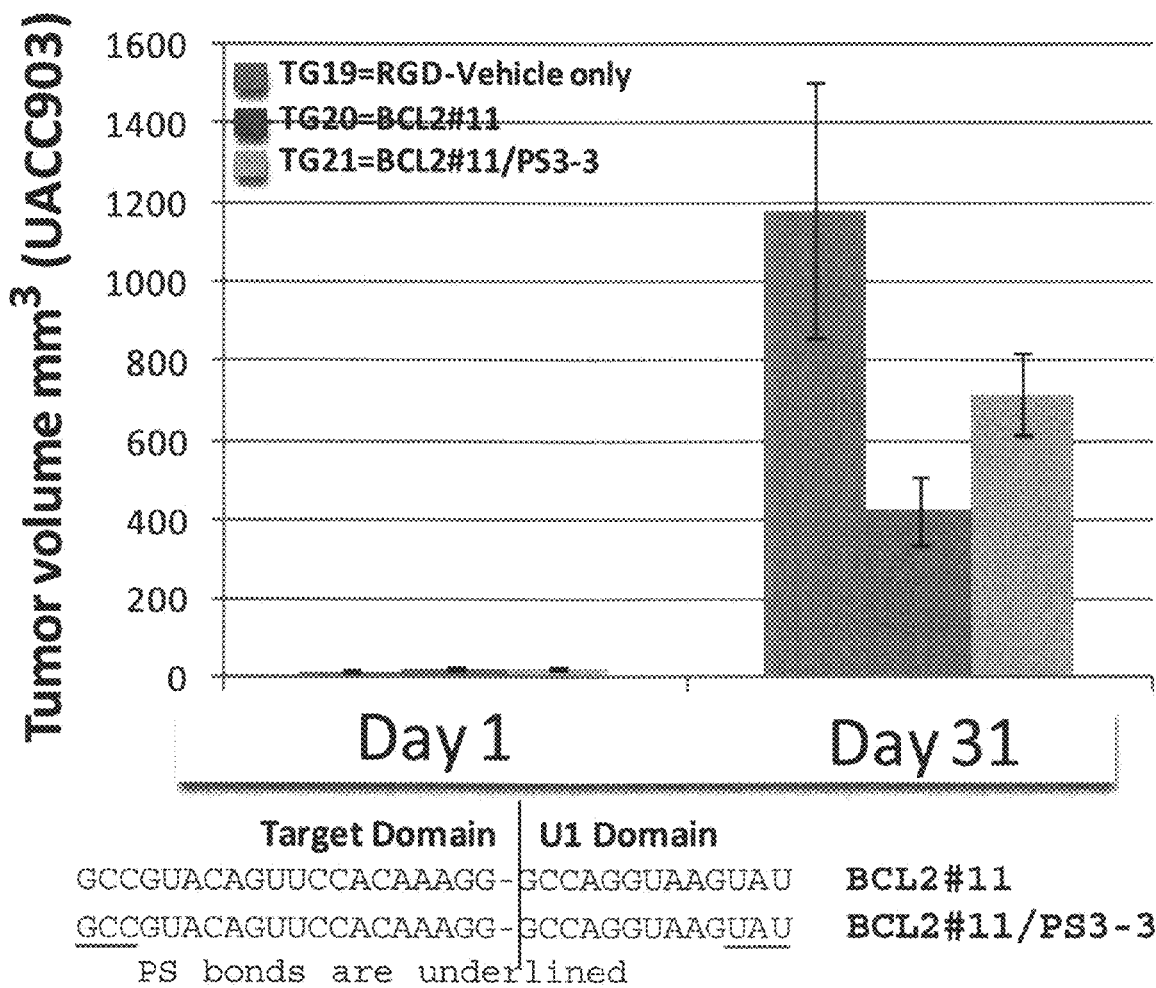
FIG. 41 shows the tumor suppression observed in mouse UACC903 xenografts with the BCL2#11 Adaptor and a PS-modified variant of BCL2#11 (top to bottom: SEQ ID NOs: 80 and 85). UACC903-derived tumors typically grow more slowly than C8161 hence the treatments were of a longer duration.

To demonstrate tumor suppression is not limited to a single human melanoma cell line, that is C8161-derived tumors, a second human melanoma cell line was analyzed which harbors the most common B-RAF mutation (V600E) in melanoma, a mutation detected in about 70% of superficial spreading and nodular cutaneous melanomas and is also often found in benign, dysplastic nevi (Pollock et al. (2003) Nature Genetics, 33:19-20; Davies et al. (2002) Nature 417:949-954). B-RAF$^{V600E}$-containing melanomas are also refractory to therapy as the mutation constitutively activates B-RAF's protein kinase activity producing a sustained activation of the MAPK signaling cascade that in turn promotes cellular proliferation and survival (Wellbrock et al. (2004) Cancer Res., 64:2338-2342; Mercer et al. (2003) Biochim. Biophys. Acta., 1653:25-40). BCL2#11 suppressed UACC903 tumor xenografts growth in vivo with similar efficacy as detected for C8161 with wild type B-RAF (FIG. 41). These results indicate that Adaptor mediated silencing of BCL2 has broad application to many types of melanoma independent of the genotypes at B-RAF.

To assess the effect of phosphorothioate (PS) modified nucleotides on U1 Adaptors, TG21 mice used a PS-modified version of BCL2#11 (called BLC2#11 PS3-3) that matches BCL2#11 but has 3 PS-modified bases at each end of the oligonucleotide. As can be seen in FIG. 41, TG21 mice gave tumor suppression activity.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

Several publications and patent documents are cited in the foregoing specification in order to more fully describe the state of the art to which this invention pertains. The disclosure of each of these citations is incorporated by reference herein.

What is claimed is:

1. A method of treating cancer in a subject, said method comprising administering at least one composition comprising at least one U1 adaptor for inhibiting the expression of at least one oncogene and at least one pharmaceutically acceptable carrier,
   wherein said U1 adaptor is a nucleic acid molecule comprising an annealing domain operably linked to at least one effector domain, wherein said annealing domain hybridizes to the pre-mRNA of said oncogene, and wherein said effector domain hybridizes to the U1 snRNA of U1 snRNP.

2. The method of claim 1, wherein said annealing domain is about 10 to about 30 nucleotides in length.

3. The method of claim 1, wherein said effector domain is about 8 to about 20 nucleotides in length.

4. The method of claim 1, wherein said effector domain and annealing domain are linked by a bond.

5. The method of claim 1, wherein said effector domain and annealing domain are linked by a linker domain of about 1 to about 10 nucleotides.

6. The method of claim 1, wherein said effector domain comprises the sequence 5'-CAGGUAAGUA-3' (SEQ ID NO: 1).

7. The method of claim 1, wherein said effector domain comprises the sequence 5'-CAGGUAAGUAU-3' (SEQ ID NO: 32).

8. The method of claim 1, wherein said effector domain comprises the sequence 5'-GCCAGGUAAGUAU-3' (SEQ ID NO: 33).

9. The method of claim 1, wherein said U1 adaptor comprises at least one nucleotide analog.

10. The method molecule of claim 9, wherein said nucleotide analog is 2'-O-methylnucleotides.

11. The method of claim 9, wherein said nucleotide analog is a phosphorothioate.

12. The method of claim 1, wherein said annealing domain hybridizes with a target sequence in the 3' terminal exon of the gene of interest.

13. The method of claim 1, wherein the effector domain is operably linked to the 3' end of the annealing domain, the 5' end of the annealing domain, or both the 5' and 3' end of the annealing domain.

14. The method of claim 1, further comprising the administration of at least chemotherapeutic agent or radiation therapy.

15. The method of claim 1, comprising the administration of more than one U1 adaptor, wherein a first U1 adaptor comprises an annealing domain which hybridizes to the pre-mRNA of a first oncogene and a second U1 adaptor comprises an annealing domain which hybridizes to the pre-mRNA of a second oncogene.

16. The method of claim 1, comprising the administration of more than one U1 adaptor, wherein a first and a second U1 adaptor comprise annealing domains which hybridize to the pre-mRNA of said oncogene.

17. The method of claim 1, further comprising the administration of at least one siRNA or antisense oligonucleotide directed against said oncogene.

18. The method of claim 1, further comprising the administration of at least one siRNA or antisense oligonucleotide directed against a second oncogene.

19. The method of claim 1, wherein said nucleic acid molecule is contained within a delivery vehicle.

20. The method of claim 19, wherein said delivery vehicle is selected from the group consisting of liposomes, nanoparticles, and polymeric composition.

21. The method of claim 20, wherein said delivery vehicle is a dendrimer.

22. The method of claim 19, wherein said delivery vehicle is linked to at least one targeting moiety, wherein said targeting moiety preferentially binds cells of the cancer being treated.

23. The method of claim 22, wherein said targeting moiety comprises an Arginine-Glycine-Aspartic Acid (RGD) peptide or an analog thereof.

24. The method of claim 1, wherein said oncogene is a member of the B-cell lymphoma 2 (bcl-2) family or glutamate receptor 1 (grm1).

25. The method of claim 24, wherein said member of the bcl-2 family is selected from the group consisting of bcl-2, bcl-XL, bcl-w, mcl-1, bfl1/A-1, and bcl-B.

* * * * *

SEQUENCE LISTING

<160> NUMBER OF SEQ ID NOS: 85

<210> SEQ ID NO 1
<211> LENGTH: 10
<212> TYPE: RNA
<213> ORGANISM: Artificial Sequence
<220> FEATURE:
<223> OTHER INFORMATION: Synthetic Sequence

<400> SEQUENCE: 1
cagguaagua                                                          10

<210> SEQ ID NO 2
<211> LENGTH: 10
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (4)...(5)
<223> OTHER INFORMATION: n = pseudouridine

<400> SEQUENCE: 2 uacnnaccug                                                          10

<210> SEQ ID NO 3

```
<211> LENGTH: 10
<212> TYPE: RNA
<213> ORGANISM: Artificial Sequence
<220> FEATURE:
<223> OTHER INFORMATION: Synthetic Sequence

<400> SEQUENCE: 3
gagguaagua                                                                  10

<210> SEQ ID NO 4
<211> LENGTH: 10
<212> TYPE: RNA
<213> ORGANISM: Artificial Sequence
<220> FEATURE:
<223> OTHER INFORMATION: Synthetic Sequence

<400> SEQUENCE: 4
cacucgagua                                                                  10

<210> SEQ ID NO 5
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 5
ctcgagagua uauuguguau uucug                                                 25

<210> SEQ ID NO 6
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5-7, 9, 11-13, 15, 17, 19, 21, 23, 25
<223> OTHER INFORMATION: locked nucleic acids

<400> SEQUENCE: 6
cagaaataca caatacaggt aagta                                                 25

<210> SEQ ID NO 7
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5-7, 9, 11-13, 15, 17, 19, 21, 23, 25
<223> OTHER INFORMATION: locked nucleic acids

<400> SEQUENCE: 7
cagaaataca caatacaact cacta                                                 25

<210> SEQ ID NO 8
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 8
tgtttccagg atgcctgtt                                                        19

<210> SEQ ID NO 9
```

```
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 9
ggacattagg tgtggatgtc g                                              21

<210> SEQ ID NO 10
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 10
agccacatcg ctcagacac                                                 19

<210> SEQ ID NO 11
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 11
gcccaatacg accaaatcc                                                 19

<210> SEQ ID NO 12
<211> LENGTH: 28
<212> TYPE: RNA
<213> ORGANISM: Artificial Sequence
<220> FEATURE:
<223> OTHER INFORMATION: Synthetic Sequence

<400> SEQUENCE: 12
cuucuggagg aaugcauguc acaggcgg                                       28

<210> SEQ ID NO 13
<211> LENGTH: 28
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 5, 9, 13, 18, 20, 23, 27
<223> OTHER INFORMATION: locked nucleic acids

<400> SEQUENCE: 13
ccgcctgtga catgcattca ggtaagta                                       28

<210> SEQ ID NO 14
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (16)...(25)
<223> OTHER INFORMATION: 2'-O-methyl RNA
<220> FEATURE:
<221> NAME/KEY: misc_feature
<222> LOCATION: 1, 3, 5-7, 9, 11-13, 15
<223> OTHER INFORMATION: locked nucleic acids

<400> SEQUENCE: 14
```

-continued cagaaataca caatacaggu aagua                                    25

<210> SEQ ID NO 15
<211> LENGTH: 25
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)...(25)
<223> OTHER INFORMATION: 2'-O-methyl RNA

<400> SEQUENCE: 15
cagaaauaca caauacaggu aagua                                    25

<210> SEQ ID NO 16
<211> LENGTH: 35
<212> TYPE: RNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)...(35)
<223> OTHER INFORMATION: 2'-O-methyl RNA
<220> FEATURE:
<221> NAME/KEY: misc_feature
<222> LOCATION: (1)...(35)
<223> OTHER INFORMATION: phosphorothioate bonds

<400> SEQUENCE: 16
agaaaaugaa cagaaauaca caauacaggu aagua                         35

<210> SEQ ID NO 17
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (16)...(25)
<223> OTHER INFORMATION: 2'-O-methyl RNA
<220> FEATURE:
<221> NAME/KEY: misc_feature
<222> LOCATION: 1, 3, 5-7, 9, 11-13, 15
<223> OTHER INFORMATION: locked nucleic acids
<220> FEATURE:
<221> NAME/KEY: misc_feature
<222> LOCATION: (1)...(25)
<223> OTHER INFORMATION: phosphorothioate bonds

<400> SEQUENCE: 17
cagaaataca caatacaggu aagua                                    25

<210> SEQ ID NO 18
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)...(10)
<223> OTHER INFORMATION: 2'-O-methyl RNA
<220> FEATURE:
<221> NAME/KEY: misc_feature
<222> LOCATION: 11, 13, 15-17, 19, 21-23, 25
<223> OTHER INFORMATION: locked nucleic acids
<220> FEATURE:
<221> NAME/KEY: misc_feature
<222> LOCATION: (1)...(25)

```
<223> OTHER INFORMATION: phosphorothioate bonds

<400> SEQUENCE: 18
cagguaagua cagaaataca caata                                              25

<210> SEQ ID NO 19
<211> LENGTH: 35
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: 1-10, 26-35
<223> OTHER INFORMATION: 2'-O-methyl RNA
<220> FEATURE:
<221> NAME/KEY: misc_feature
<222> LOCATION: 11, 13, 15-17, 19, 21-23, 25
<223> OTHER INFORMATION: locked nucleic acids
<220> FEATURE:
<221> NAME/KEY: misc_feature
<222> LOCATION: (1)...(35)
<223> OTHER INFORMATION: phosphorothioate bonds

<400> SEQUENCE: 19
cagguaagua cagaaataca caatacaggu aagua                                   35

<210> SEQ ID NO 20
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)...(15)
<223> OTHER INFORMATION: locked nucleic acids
<220> FEATURE:
<221> NAME/KEY: modified_base
<222> LOCATION: (16)...(25)
<223> OTHER INFORMATION: 2'-O-methyl RNA

<400> SEQUENCE: 20
cagaaataca caatacaggu aagua                                              25

<210> SEQ ID NO 21
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)...(12)
<223> OTHER INFORMATION: locked nucleic acids
<220> FEATURE:
<221> NAME/KEY: modified_base
<222> LOCATION: (13)...(22)
<223> OTHER INFORMATION: 2'-O-methyl RNA

<400> SEQUENCE: 21
aaatacacaa tacagguaag ua                                                 22

<210> SEQ ID NO 22
<211> LENGTH: 29
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (19)...(29)
```

```
<223> OTHER INFORMATION: 2'-O-methyl RNA
<220> FEATURE:
<221> NAME/KEY: misc_feature
<222> LOCATION: 1, 5, 9, 13, 18
<223> OTHER INFORMATION: locked nucleic acids

<400> SEQUENCE: 22
ccgcctgtga catgcattca gguaaguau                                            29

<210> SEQ ID NO 23
<211> LENGTH: 28
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5-7, 9, 11-13, 15
<223> OTHER INFORMATION: locked nucleic acids
<220> FEATURE:
<221> NAME/KEY: modified_base
<222> LOCATION: (16)...(28)
<223> OTHER INFORMATION: 2'-O-methyl-RNA

<400> SEQUENCE: 23
cagaaataca caatagccag guaaguau                                             28

<210> SEQ ID NO 24
<211> LENGTH: 27
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5-7, 9, 11-13, 15
<223> OTHER INFORMATION: locked nucleic acids
<220> FEATURE:
<221> NAME/KEY: modified_base
<222> LOCATION: (16)...(27)
<223> OTHER INFORMATION: 2'-O-methyl RNA

<400> SEQUENCE: 24
cagaaataca caataccagg uaaguau                                              27

<210> SEQ ID NO 25
<211> LENGTH: 26
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5-7, 9, 11-13, 15
<223> OTHER INFORMATION: locked nucleic acids
<220> FEATURE:
<221> NAME/KEY: modified_base
<222> LOCATION: (16)...(26)
<223> OTHER INFORMATION: 2'-O-methyl RNA

<400> SEQUENCE: 25
cagaaataca caatacaggu aaguau                                               26

<210> SEQ ID NO 26
<211> LENGTH: 24
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5-7, 9, 11-13, 15
```

-continued

<223> OTHER INFORMATION: locked nucleic acids
<220> FEATURE:
<221> NAME/KEY: modified_base
<222> LOCATION: (16)...(24)
<223> OTHER INFORMATION: 2'-O-methyl RNA

<400> SEQUENCE: 26
cagaaataca caatacaggu aagu                                            24

<210> SEQ ID NO 27
<211> LENGTH: 23
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5-7, 9, 11-13, 15
<223> OTHER INFORMATION: locked nucleic acids
<220> FEATURE:
<221> NAME/KEY: modified_base
<222> LOCATION: (16)...(23)
<223> OTHER INFORMATION: 2'-O-methyl RNA

<400> SEQUENCE: 27
cagaaataca caatacaggu aag                                             23

<210> SEQ ID NO 28
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5-7, 9, 11-13, 15
<223> OTHER INFORMATION: locked nucleic acids
<220> FEATURE:
<221> NAME/KEY: modified_base
<222> LOCATION: (16)...(22)
<223> OTHER INFORMATION: 2'-O-methyl RNA

<400> SEQUENCE: 28
cagaaataca caatacaggu aa                                              22

<210> SEQ ID NO 29
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 29
ttcaaggggt ctacacaggt aagtaa                                          26

<210> SEQ ID NO 30
<211> LENGTH: 29
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (19)...(29)
<223> OTHER INFORMATION: 2'-O-methyl RNA
<220> FEATURE:
<221> NAME/KEY: misc_feature
<222> LOCATION: 1, 2, 5, 16-18
<223> OTHER INFORMATION: locked nucleic acids

<400> SEQUENCE: 30

-continued ccgcctgtga catgcattca gauaacuau                                29

<210> SEQ ID NO 31
<211> LENGTH: 29
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (19)...(29)
<223> OTHER INFORMATION: 2'-O-methyl RNA
<220> FEATURE:
<221> NAME/KEY: misc_feature
<222> LOCATION: 1, 2, 5, 16-18
<223> OTHER INFORMATION: locked nucleic acids

<400> SEQUENCE: 31
ccgcctgtga catgcattca gguaaguau                                29

<210> SEQ ID NO 32
<211> LENGTH: 11
<212> TYPE: RNA
<213> ORGANISM: Artificial Sequence
<220> FEATURE:
<223> OTHER INFORMATION: Synthetic Sequence

<400> SEQUENCE: 32
cagguaagua u                                                   11

<210> SEQ ID NO 33
<211> LENGTH: 13
<212> TYPE: RNA
<213> ORGANISM: Artificial Sequence
<220> FEATURE:
<223> OTHER INFORMATION: Synthetic Sequence

<400> SEQUENCE: 33
gccagguaag uau                                                 13

<210> SEQ ID NO 34
<211> LENGTH: 34
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (16)...(34)
<223> OTHER INFORMATION: 2'-O-methyl RNA
<220> FEATURE:
<221> NAME/KEY: misc_feature
<222> LOCATION: 1, 3, 5-7, 9, 11-13, 15
<223> OTHER INFORMATION: locked nucleic acids

<400> SEQUENCE: 34
cagaaataca caatuccccc ugccagguaa guau                          34

<210> SEQ ID NO 35
<211> LENGTH: 32
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (16)...(32)
<223> OTHER INFORMATION: 2'-O-methyl RNA
<220> FEATURE:
<221> NAME/KEY: misc_feature
<222> LOCATION: 1, 3, 5-7, 9, 11-13, 15

<223> OTHER INFORMATION: locked nucleic acids

<400> SEQUENCE: 35
cagaaataca caatacccug ccagguaagu au          32

<210> SEQ ID NO 36
<211> LENGTH: 30
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (16)...(30)
<223> OTHER INFORMATION: 2'-O-methyl RNA
<220> FEATURE:
<221> NAME/KEY: misc_feature
<222> LOCATION: 1, 3, 5-7, 9, 11-13, 15
<223> OTHER INFORMATION: locked nucleic acids

<400> SEQUENCE: 36
cagaaataca caatacugcc agguaaguau          30

<210> SEQ ID NO 37
<211> LENGTH: 29
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (16)...(29)
<223> OTHER INFORMATION: 2'-O-methyl RNA
<220> FEATURE:
<221> NAME/KEY: misc_feature
<222> LOCATION: 1, 3, 5-7, 9, 11-13, 15
<223> OTHER INFORMATION: locked nucleic acids

<400> SEQUENCE: 37
cagaaataca caataugcca gguaaguau          29

<210> SEQ ID NO 38
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (16)...(25)
<223> OTHER INFORMATION: 2'-O-methyl RNA
<220> FEATURE:
<221> NAME/KEY: misc_feature
<222> LOCATION: 1, 3, 5-7, 9, 11-13, 15
<223> OTHER INFORMATION: locked nucleic acids

<400> SEQUENCE: 38
cagaaataca caatacagcu aagua          25

<210> SEQ ID NO 39
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (16)...(25)
<223> OTHER INFORMATION: 2'-O-methyl RNA
<220> FEATURE:
<221> NAME/KEY: misc_feature
<222> LOCATION: 1, 3, 5-7, 9, 11-13, 15

-continued

<223> OTHER INFORMATION: locked nucleic acids

<400> SEQUENCE: 39
cagaaataca caatacagcu cagua                                               25

<210> SEQ ID NO 40
<211> LENGTH: 26
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)...(11)
<223> OTHER INFORMATION: 2'-O-methyl RNA
<220> FEATURE:
<221> NAME/KEY: misc_feature
<222> LOCATION: 12, 14, 16-18, 20, 22-25
<223> OTHER INFORMATION: locked nucleic acids

<400> SEQUENCE: 40
cagguaagua ucagaaatac acaata                                              26

<210> SEQ ID NO 41
<211> LENGTH: 28
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)...(13)
<223> OTHER INFORMATION: 2'-O-methyl RNA
<220> FEATURE:
<221> NAME/KEY: misc_feature
<222> LOCATION: 14, 16, 18-20, 22, 24-27
<223> OTHER INFORMATION: locked nucleic acids

<400> SEQUENCE: 41
gccagguaag uaucagaaat acacaata                                            28

<210> SEQ ID NO 42
<211> LENGTH: 30
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)...(15)
<223> OTHER INFORMATION: 2'-O-methyl RNA
<220> FEATURE:
<221> NAME/KEY: misc_feature
<222> LOCATION: 16, 18, 20-22, 24, 26-29
<223> OTHER INFORMATION: locked nucleic acids

<400> SEQUENCE: 42
cugccaggua aguaucagaa atacacaata                                          30

<210> SEQ ID NO 43
<211> LENGTH: 28
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5-7, 9, 11-13, 15, 17, 19, 21, 23, 25
<223> OTHER INFORMATION: locked nucleic acids
<220> FEATURE:
<221> NAME/KEY: modified_base
<222> LOCATION: 16, 18, 20, 22, 24, 26-28

```
<223> OTHER INFORMATION: 2'-O-methyl-RNA

<400> SEQUENCE: 43
cagaaataca caatagccag guaaguau                                          28

<210> SEQ ID NO 44
<211> LENGTH: 28
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1-4, 6, 7, 12, 15, 17, 19, 21, 23, 25
<223> OTHER INFORMATION: locked nucleic acids
<220> FEATURE:
<221> NAME/KEY: modified_base
<222> LOCATION: 16, 18, 20, 22, 24, 26-28
<223> OTHER INFORMATION: 2'-O-methyl-RNA

<400> SEQUENCE: 44
cagatataga cattagccag guaaguau                                          28

<210> SEQ ID NO 45
<211> LENGTH: 28
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1-4, 6, 7, 12, 13, 15, 17, 19, 21, 23, 25
<223> OTHER INFORMATION: locked nucleic acids
<220> FEATURE:
<221> NAME/KEY: modified_base
<222> LOCATION: 16, 18, 20, 22, 24, 26-28
<223> OTHER INFORMATION: 2'-O-methyl-RNA

<400> SEQUENCE: 45
cagatataga caatagccag guaaguau                                          28

<210> SEQ ID NO 46
<211> LENGTH: 28
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1-4, 6, 7, 12, 13, 15, 17, 19, 21, 23, 25
<223> OTHER INFORMATION: locked nucleic acids
<220> FEATURE:
<221> NAME/KEY: modified_base
<222> LOCATION: 16, 18, 20, 22, 24, 26-28
<223> OTHER INFORMATION: 2'-O-methyl-RNA

<400> SEQUENCE: 46
cagaaataga caatagccag guaaguau                                          28

<210> SEQ ID NO 47
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 47
tattgtgtat ttctg                                                        15

<210> SEQ ID NO 48
```

```
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 48
taatgtctat atctg                                                      15

<210> SEQ ID NO 49
<211> LENGTH: 29
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (19)...(29)
<223> OTHER INFORMATION: 2'-O-methyl RNA
<220> FEATURE:
<221> NAME/KEY: misc_feature
<222> LOCATION: 1, 5, 9, 13, 18
<223> OTHER INFORMATION: locked nucleic acids

<400> SEQUENCE: 49
ccgcctgtga catgcattca gauaacuau                                       29

<210> SEQ ID NO 50
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (16)...(25)
<223> OTHER INFORMATION: 2'-O-methyl RNA
<220> FEATURE:
<221> NAME/KEY: misc_feature
<222> LOCATION: 1, 5, 8, 10, 14
<223> OTHER INFORMATION: locked nucleic acids

<400> SEQUENCE: 50
tgtctccaca tcaggcaggu aagua                                           25

<210> SEQ ID NO 51
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (16)...(25)
<223> OTHER INFORMATION: 2'-O-methyl RNA
<220> FEATURE:
<221> NAME/KEY: misc_feature
<222> LOCATION: 1, 2, 5, 9, 13, 14
<223> OTHER INFORMATION: locked nucleic acids

<400> SEQUENCE: 51
agagagtgtt ggagccaggu aagua                                           25

<210> SEQ ID NO 52
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (16)...(25)
```

```
<223> OTHER INFORMATION: 2'-O-methyl RNA
<220> FEATURE:
<221> NAME/KEY: misc_feature
<222> LOCATION: 1, 4, 7, 11, 12, 15
<223> OTHER INFORMATION: locked nucleic acids

<400> SEQUENCE: 52
tattcctggc ttcctcaggu aagua                                              25

<210> SEQ ID NO 53
<211> LENGTH: 33
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: 21-23, 25, 27, 29, 30, 33
<223> OTHER INFORMATION: 2'-O-methyl RNA
<220> FEATURE:
<221> NAME/KEY: misc_feature
<222> LOCATION: 1, 2, 5, 6, 9, 10, 14, 16, 17, 20, 24, 26, 28, 31, 32
<223> OTHER INFORMATION: locked nucleic acids

<400> SEQUENCE: 53
agagggacaa gtcggaacca gccagguaag tau                                     33

<210> SEQ ID NO 54
<211> LENGTH: 31
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: 19-21, 23, 24, 26, 28, 29, 31
<223> OTHER INFORMATION: 2'-O-methyl RNA
<220> FEATURE:
<221> NAME/KEY: misc_feature
<222> LOCATION: 1, 3, 6, 11, 12, 15, 17, 22, 25, 27, 30
<223> OTHER INFORMATION: locked nucleic acids

<400> SEQUENCE: 54
ctcgcaggcc acggtcacgc cagguaagta u                                       31

<210> SEQ ID NO 55
<211> LENGTH: 15
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 5-7, 9, 11-13, 15
<223> OTHER INFORMATION: locked nucleic acids

<400> SEQUENCE: 55
cagaaataca caata                                                         15

<210> SEQ ID NO 56
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 4, 6, 8, 10
<223> OTHER INFORMATION: locked nucleic acids
<220> FEATURE:
<221> NAME/KEY: modified_base
<222> LOCATION: 1, 3, 5, 7, 9, 11-13
```

```
<223> OTHER INFORMATION: 2'-O-methyl-RNA

<400> SEQUENCE: 56
gccagguaag uau                                                          13

<210> SEQ ID NO 57
<211> LENGTH: 18
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 1, 3, 6, 11, 12, 15, 17
<223> OTHER INFORMATION: locked nucleic acids

<400> SEQUENCE: 57
ctcgcaggcc acggtcac                                                     18

<210> SEQ ID NO 58
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: 1-3, 5, 6, 8, 10, 11, 13
<223> OTHER INFORMATION: 2'-O-methyl RNA
<220> FEATURE:
<221> NAME/KEY: misc_feature
<222> LOCATION: 4, 7, 9, 12
<223> OTHER INFORMATION: locked nucleic acids

<400> SEQUENCE: 58
gccagguaag tau                                                          13

<210> SEQ ID NO 59
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)...(10)
<223> OTHER INFORMATION: 2'-O-methyl RNA
<220> FEATURE:
<221> NAME/KEY: misc_feature
<222> LOCATION: 11, 13, 15-17, 19, 21-23, 25
<223> OTHER INFORMATION: locked nucleic acids

<400> SEQUENCE: 59
cagguaagua cagaaatac acaata                                             25

<210> SEQ ID NO 60
<211> LENGTH: 35
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: 1-10, 27-36
<223> OTHER INFORMATION: 2'-O-methyl RNA
<220> FEATURE:
<221> NAME/KEY: misc_feature
<222> LOCATION: 11, 13, 15-17, 19, 21-23, 25
<223> OTHER INFORMATION: locked nucleic acids

<400> SEQUENCE: 60
```
cagguaagua cagaaauaca caauacaggu aagua                                    35

<210> SEQ ID NO 61
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 61
gtaaaacgac ggccagt                                                        17

<210> SEQ ID NO 62
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)...(23)
<223> OTHER INFORMATION: RNA

<400> SEQUENCE: 62
ccuagacacc agcauacaga gugac                                               25

<210> SEQ ID NO 63
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 63
gucacucugu augcuggugu cuaggag                                             27

<210> SEQ ID NO 64
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)...(23)
<223> OTHER INFORMATION: RNA

<400> SEQUENCE: 64
accucacgcc uucaccuuua acacc                                               25

<210> SEQ ID NO 65
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 65
gguguuaaag gugaaggcgu gaggugu                                             27

<210> SEQ ID NO 66
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 66

```
atgtcgacta catcgaggag gact                                          24

<210> SEQ ID NO 67
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 67
tggtcactct gtatgctggt gtct                                          24

<210> SEQ ID NO 68
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 68
ccatcagacg cttccagtct                                               20

<210> SEQ ID NO 69
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 69
gtctctgggc aaaggcttc                                                19

<210> SEQ ID NO 70
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 70
tggctcagga cccagtttta                                               20

<210> SEQ ID NO 71
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 71
tcttctgcct ggtcttctcc                                               20

<210> SEQ ID NO 72
<211> LENGTH: 34
<212> TYPE: DNA
<213> ORGANISM: Artificial Sequence
<220> FEATURE:
<223> OTHER INFORMATION: Synthetic Sequence

<400> SEQUENCE: 72
cgcgaagctt gttttgaacg aagaatgtga tcag                               34

<210> SEQ ID NO 73
<211> LENGTH: 44
<212> TYPE: DNA
<213> ORGANISM: Artificial Sequence
<220> FEATURE:
```

<223> OTHER INFORMATION: Synthetic Sequence

<400> SEQUENCE: 73
gagaggtacc ctgtggcacc tgttctatgt cccgcaggaa tatc            44

<210> SEQ ID NO 74
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 74
tgcggtaccg gcctggagta caatgtca            28

<210> SEQ ID NO 75
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 75
tgcggtaccg aggtgacacg catggtgtc            29

<210> SEQ ID NO 76
<211> LENGTH: 10
<212> TYPE: RNA
<213> ORGANISM: Artificial Sequence
<220> FEATURE:
<223> OTHER INFORMATION: Synthetic Sequence

<400> SEQUENCE: 76
caacucacua            10

<210> SEQ ID NO 77
<211> LENGTH: 33
<212> TYPE: RNA
<213> ORGANISM: Artificial Sequence
<220> FEATURE:
<223> OTHER INFORMATION: Synthetic Sequence

<400> SEQUENCE: 77
acguugggag gggugcagag gccagguaag uau            33

<210> SEQ ID NO 78
<211> LENGTH: 33
<212> TYPE: RNA
<213> ORGANISM: Artificial Sequence
<220> FEATURE:
<223> OTHER INFORMATION: Synthetic Sequence

<400> SEQUENCE: 78
uucccgcucg ugcucauaca gccagguaag uau            33

<210> SEQ ID NO 79
<211> LENGTH: 33
<212> TYPE: RNA
<213> ORGANISM: Artificial Sequence
<220> FEATURE:
<223> OTHER INFORMATION: Synthetic Sequence

<400> SEQUENCE: 79
uuuuagugag gggcuugaug gccagguaag uau            33

<210> SEQ ID NO 80

```
<211> LENGTH: 33
<212> TYPE: RNA
<213> ORGANISM: Artificial Sequence
<220> FEATURE:
<223> OTHER INFORMATION: Synthetic Sequence

<400> SEQUENCE: 80
gccguacagu uccacaaagg gccagguaag uau                                33

<210> SEQ ID NO 81
<211> LENGTH: 31
<212> TYPE: RNA
<213> ORGANISM: Artificial Sequence
<220> FEATURE:
<223> OTHER INFORMATION: Synthetic Sequence

<400> SEQUENCE: 81
cguucagguc caaaaacggc cagguaagua u                                  31

<210> SEQ ID NO 82
<211> LENGTH: 33
<212> TYPE: RNA
<213> ORGANISM: Artificial Sequence
<220> FEATURE:
<223> OTHER INFORMATION: Synthetic Sequence

<400> SEQUENCE: 82
gccguacagu uccacaaagg gccagcucag uau                                33

<210> SEQ ID NO 83
<211> LENGTH: 33
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 2, 6, 10, 14, 18
<223> OTHER INFORMATION: locked nucleic acids

<400> SEQUENCE: 83
gccguacagt uccacaaagg gccagguaag uau                                33

<210> SEQ ID NO 84
<211> LENGTH: 33
<212> TYPE: RNA
<213> ORGANISM: Artificial Sequence
<220> FEATURE:
<223> OTHER INFORMATION: Synthetic Sequence

<400> SEQUENCE: 84
cagccaggag aaaucaaaca gccagguaag uau                                33

<210> SEQ ID NO 85
<211> LENGTH: 33
<212> TYPE: RNA
<213> ORGANISM: Artificial Sequence
<220> FEATURE:
<223> OTHER INFORMATION: Synthetic Sequence

<400> SEQUENCE: 85
gccguacagu uccacaaagg gccagguaag uau                                33
```